(12) United States Patent
Hoornaert et al.

(10) Patent No.: US 7,923,554 B2
(45) Date of Patent: Apr. 12, 2011

(54) HIV INHIBITING 1,2,4-TRIAZIN-6-ONE DERIVATIVES

(75) Inventors: Georges Joseph Cornelius Hoornaert, Kessel-Lo (BE); Amuri Kilonda, Heverlee (BE); Jan Heeres, Vosselaar (BE); Paulus Joannes Lewi, Turnhout (BE); Marc René de Jonge, Tilburg (NL); Frederik Frans Desiré Daeyaert, Beerse (BE); Hendrik Maarten Vinkers, Antwerp (BE); Lucien Maria Henricus Koymans, Retie (BE); Paul Adriaan Jan Janssen, Vosselaar (BE); Frank Xavier Jozef Herwig Arts, legal representative, Brasschaat (BE)

(73) Assignee: Janssen Pharmaceutica N.V., Beerse (BE)

( * ) Notice: Subject to any disclaimer, the term of this patent is extended or adjusted under 35 U.S.C. 154(b) by 807 days.

(21) Appl. No.: 11/573,224

(22) PCT Filed: Aug. 10, 2005

(86) PCT No.: PCT/EP2005/053936
§ 371 (c)(1),
(2), (4) Date: Feb. 5, 2007

(87) PCT Pub. No.: WO2006/015985
PCT Pub. Date: Feb. 16, 2006

(65) Prior Publication Data
US 2009/0012092 A1   Jan. 8, 2009

(30) Foreign Application Priority Data
Aug. 10, 2004  (EP) .................................... 04103858

(51) Int. Cl.
C07D 253/07   (2006.01)
C07D 253/065  (2006.01)
A61K 31/53    (2006.01)
A61P 31/18    (2006.01)

(52) U.S. Cl. ........................................ 544/182; 514/242
(58) Field of Classification Search .................. 544/182; 514/242, 182
See application file for complete search history.

(56) References Cited

U.S. PATENT DOCUMENTS
3,459,731 A     8/1969  Gramera et al.
2010/0160310 A1 6/2010  Freyne et al.

FOREIGN PATENT DOCUMENTS
EP  0 834 507 A1    4/1998
EP  0834507 B1      5/2004
WO  WO 97/18839 A1  5/1997
WO  WO 99/50250 A1  10/1999
WO  WO 99/50256     10/1999
WO  WO 00/27825 A1  5/2000
WO  WO 00/27828 A2  5/2000
WO  WO 01/85700 A2  11/2001
WO  WO 02/078708 A1 10/2002
WO  WO 03/016306 A1 2/2003

OTHER PUBLICATIONS

Magden et al., Appl Microbiol Biotechnol (2005) 66: 612-621.*
International Search Report dated Nov. 16, 2005 for related International Application No. PCT/EP2005/053936.
Koyanagi, et al., "Selective Cytotoxicity of Aids Virus Infection Towards HTLV-I-Transformed Cell Lines", Int. J. Cancer, (1985), pp. 445-451, vol. 36(4), Alan R. Liss, Inc.
In the U.S. Patent and Trademark Office, Non-Final Office Action in re: U.S. Appl. No. 11/720,681 dated Sep. 14, 2010, 7 pages.

* cited by examiner

*Primary Examiner* — Venkataraman Balasubramanian
(74) *Attorney, Agent, or Firm* — Patton Boggs LLP

(57) ABSTRACT

The present invention relates to HIV replication inhibitors of formula

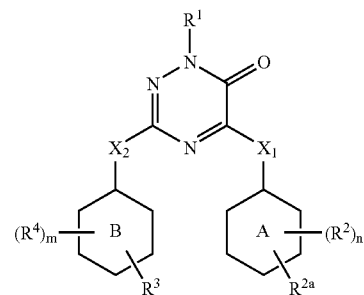

(I)

a N-oxide, a pharmaceutically acceptable addition salt, a quaternary amine or a stereochemically isomeric form thereof, wherein ring A and ring B represent phenyl, pyridyl, pyridazinyl, pyrimidinyl or pyrazinyl; n and m are 1 to 4; $R^1$ represents hydrogen; aryl; formyl; $C_{1-6}$alkylcarbonyl; $C_{1-6}$alkyloxycarbonyl; optionally substituted $C_{1-6}$alkyl; $C_{1-6}$alkyloxy$C_{1-6}$alkylcarbonyl substituted with $C_{1-6}$alkyloxycarbonyl; $R^2$ or $R^4$ represents hydrogen; hydroxy; halo; optionally substituted $C_{1-6}$alkyl; optionally substituted $C_{2-6}$alkenyl; optionally substituted $C_{2-6}$alkynyl; $C_{3-7}$cycloalkyl; $C_{1-6}$alkyloxy; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; —S(=O)$_p$R$^6$; —NH—S(=O)$_p$R$^6$; —C(=O)R$^6$; —NHC(=O)H; —C(=O)NHNH$_2$; NHC(=O)R$^6$; C(=NH)R$^6$; or R$^7$; R$^{2a}$ or R$^3$ represents cyano; aminocarbonyl; amino; halo; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; optionally substituted $C_{1-6}$alkyl; optionally substituted $C_{1-6}$alkyloxy; optionally substituted $C_{1-6}$alkyloxy$C_{1-6}$alkyl; optionally substituted $C_{2-6}$alkenyl; optionally substituted $C_{2-6}$alkynyl; —C(=N—O—R$^8$)—$C_{1-4}$alkyl; R$^7$ or —X$_3$—R$^9$; X$_1$ or X$_2$ represents —NR$^1$—; —NH—NH—; —N=N—; —O—; —C(=O)—; —C$_{1-4}$alkanediyl-; —CHOH—; —S—; —S(=O)$_p$—; —X$_4$—C$_{1-4}$alkanediyl-; —C$_{1-4}$alkanediyl-X$_4$—; or —C$_{1-4}$alkanediyl-X$_4$—C$_{1-4}$alkanediyl-; their use as a medicine, their use for the manufacture of a medicament for the treatment or the prevention of HIV infection; their processes for preparation and pharmaceutical compositions comprising them.

25 Claims, No Drawings

HIV INHIBITING 1,2,4-TRIAZIN-6-ONE DERIVATIVES

CROSS-REFERENCE TO RELATED APPLICATIONS

This application is a National Stage under 35 U.S.C. §371 of PCT Application No. PCT/EP2005/53936, filed Aug. 10, 2005, which claims priority from European Patent Application No. 04103858.9, filed Aug. 10, 2004, all of which are incorporated by reference in their entirety.

The present invention is concerned with 1,2,4-triazin-6-one derivatives having HIV (Human Immunodeficiency Virus) replication inhibiting properties. The invention further relates to methods for their preparation and pharmaceutical compositions comprising them. The invention also relates to the use of said compounds for the manufacture of a medicament for the treatment or the prevention of HIV infection.

EP 834,507, WO 99/50256, WO 00/27828 and WO 01/85700 disclose HIV inhibiting triazine derivatives.

WO 99/50250, WO 00/27825, WO 01/85700 and WO 03/016306 disclose HIV inhibiting pyrimidine derivatives.

WO 02/078708 discloses HIV inhibiting pyrazinone derivatives.

The compounds of the present invention differ from those of the prior art in structure, pharmacological activity or potency.

The compounds of the invention are highly active to inhibit the replication of Human Immunodeficiency Virus (HIV), and in particular they are highly active to inhibit the replication of mutant strains, in particular drug or multidrug resistant HIV strains, i.e. strains which have become resistant to one or more art-known NNRTI drug(s) (Non Nucleoside Reverse Transcriptase Inhibitor drugs).

The present invention concerns a compound of formula

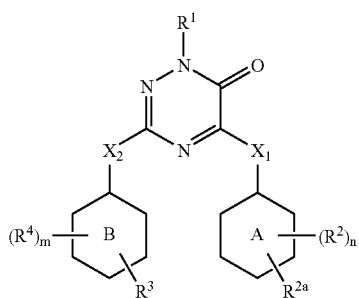

(I)

a N-oxide, a pharmaceutically acceptable addition salt, a quaternary amine or a stereochemically isomeric form thereof, wherein ring A represents phenyl, pyridyl, pyridazinyl, pyrimidinyl or pyrazinyl;

ring B represents phenyl, pyridyl, pyridazinyl, pyrimidinyl or pyrazinyl;

n is 1, 2, 3 and in case ring A represents phenyl, then n may also be 4;

m is 1, 2, 3 and in case ring B represents phenyl, then m may also be 4;

$R^1$ represents hydrogen; aryl; formyl; $C_{1-6}$alkylcarbonyl; $C_{1-6}$alkyloxycarbonyl; $C_{1-6}$alkyl optionally substituted with $R^5$; or $C_{1-6}$alkyloxy$C_{1-6}$alkylcarbonyl substituted with $C_{1-16}$alkyloxycarbonyl;

each $R^2$ independently represents hydrogen; hydroxy; halo; $C_{1-6}$alkyl optionally substituted with one or more substituents each independently selected from halo, cyano, hydroxy or —C(=O)$R^6$; $C_{2-6}$alkenyl optionally substituted with one or more substituents each independently selected from halo, cyano, hydroxy or —C(=O)$R^6$; $C_{2-6}$alkynyl optionally substituted with one or more substituents each independently selected from halo, cyano, hydroxy or —C(=O)$R^6$; $C_{3-7}$cycloalkyl; $C_{1-6}$alkyloxy; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; —S(=O)$_p$$R^6$; —NH—S(=O)$_p$$R^6$; —C(=O)$R^6$; —NHC(=O)H; —C(=O)NHNH$_2$; NHC(=O)$R^6$; C(=NH)$R^6$; or $R^7$;

$R^{2a}$ represents cyano; aminocarbonyl; amino; halo; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; $C_{1-6}$alkyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkynyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; —C(=N—O—R$^8$)—$C_{1-4}$alkyl; $R^7$ or —$X_3$—$R^7$;

$X_1$ represents —NR$^1$—; —NH—NH—; —N=N—; —O—; —C(=O)—; —$C_{1-4}$alkanediyl-; —CHOH—; —S—; —S(=O)$_p$—; —$X_4$—$C_{1-4}$alkanediyl-; —$C_{1-4}$alkanediyl-$X_4$—; or —$C_{1-4}$alkanediyl-$X_4$—$C_{1-4}$alkanediyl-;

$X_2$ represents —NR$^1$—; —NH—NH—; —N=N—; —O—; —C(=O)—; —$C_{1-4}$alkanediyl-; —CHOH—; —S—; —S(=O)$_p$—; —$X_4$—$C_{1-4}$alkanediyl-; —$C_{1-4}$alkanediyl-$X_4$—; or —$C_{1-4}$alkanediyl-$X_4$—$C_{1-4}$alkanediyl-;

$X_3$ represents —NR$^1$—; —NH—NH—; —N=N—; —O—; —C(=O)—; —S—; —S(=O)$_p$—; —$X_{4a}$—$C_{1-4}$alkanediyl-; —$C_{1-4}$alkanediyl-$X_{4b}$—; —$C_{1-4}$alkanediyl-$X_{4a}$—$C_{1-4}$alkanediyl-; or —C(=N—OR$^8$)—$C_{1-4}$alkanediyl-;

$X_4$ represents —NR$^1$—; —NH—NH—; —N=N—; —O—; —C(=O)—; —CHOH—; —S—; or —S(=O)$_p$—;

$X_{4a}$ represents —NR$^1$—; —NH—NH—; —N=N—; —C(=O)—; —S—; or —S(=O)$_p$—;

$X_{4b}$ represents —NH—NH—; —N=N—; —O—; —C(=O)—; —S—; or —S(=O)$_p$—;

$R^3$ represents cyano; aminocarbonyl; amino; halo; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; $C_{1-6}$alkyl optionally substituted with one or more substituents each independently selected from halo, cyano, hydroxy, NR$^9$R$^{10}$, —C(=O)—NR$^9$R$^{10}$, —C(=O)—C$_{1-6}$alkyl, —C(=O)—O—C$_{1-6}$alkyl, —C(=O)-polyhaloC$_{1-6}$alkyl, —C(=O)—O-polyhaloC$_{1-6}$alkyl or R$^7$; C$_{1-6}$alkyloxy optionally substituted with one or more substituents each independently selected from halo, cyano, hydroxy, NR$^9$R$^{10}$, —C(=O)—NR$^9$R$^{10}$, —C(=O)—C$_{1-6}$alkyl, —C(=O)—O—C$_{1-6}$alkyl, —C(=O)-polyhaloC$_{1-6}$alkyl, —C(=O)—O-polyhaloC$_{1-6}$alkyl or R$^7$; C$_{1-6}$alkyloxyC$_{1-6}$alkyl optionally substituted with one or more substituents each independently selected from halo, cyano, hydroxy, NR$^9$R$^{10}$, —C(=O)—NR$^9$R$^{10}$, —C(=O)—C$_{1-6}$alkyl, —C(=O)—O—C$_{1-6}$alkyl, —C(=O)-polyhaloC$_{1-6}$alkyl, —C(=O)—O-polyhaloC$_{1-6}$alkyl or R$^7$; C$_{2-6}$alkenyl optionally substituted with one or more substituents each independently selected from halo, cyano, hydroxy, NR$^9$R$^{10}$, —C(=O)—NR$^9$R$^{10}$, —C(=O)—C$_{1-6}$alkyl, —C(=O)—O—C$_{1-6}$alkyl, —C(=O)-polyhaloC$_{1-6}$alkyl, —C(=O)—O-polyhaloC$_{1-6}$alkyl or R$^7$; C$_{2-6}$alkynyl optionally substituted with one or more substituents each independently selected from halo, cyano, hydroxy, NR$^9$R$^{10}$, —C(=O)—NR$^9$R$^{10}$, —C(=O)—C$_{1-6}$alkyl, —C(=O)—O—C$_{1-6}$alkyl, —C(=O)-polyhaloC$_{1-6}$alkyl, —C(=O)—O-polyhaloC$_{1-6}$alkyl or R$^7$; —C(=N—O—R$^8$)—C$_{1-4}$alkyl; R$^7$ or —X$_3$—R$^7$;

each R$^4$ independently represents hydrogen; hydroxy; halo; C$_{1-6}$alkyl optionally substituted with one or more substituents each independently selected from halo, cyano, hydroxy or —C(=O)R$^6$; C$_{2-6}$alkenyl optionally substituted with one or more substituents each independently selected from halo, cyano, hydroxy or —C(=O)R$^6$; C$_{2-6}$alkynyl optionally substituted with one or more substituents each independently selected from halo, cyano, hydroxy or —C(=O)R$^6$; C$_{3-7}$cycloalkyl; C$_{1-6}$alkyloxy; C$_{1-6}$alkyloxycarbonyl; C$_{1-6}$alkylcarbonyloxy; carboxyl; cyano; nitro; amino; mono- or di(C$_{1-6}$alkyl)amino; polyhaloC$_{1-4}$alkyl; polyhaloC$_{1-4}$alkyloxy; polyhaloC$_{1-4}$alkylthio; —S(=O)$_p$R$^6$; —NH—S(=O)$_p$R$^6$; —C(=O)R$^6$; —NHC(=O)H; —C(=O)NHNH$_2$; NHC(=O)R$^6$; C(=NH)R$^6$; or R$^7$;

R$^5$ represents formyl, cyano, aminocarbonyl, mono- or di(C$_{1-4}$ alkyl)aminocarbonyl, hydroxy, C$_{1-16}$alkylcarbonyl, C$_{1-16}$alkyloxycarbonyl or C$_{1-16}$alkylcarbonyloxy;

R$^6$ represents C$_{1-4}$alkyl, amino, mono- or di(C$_{1-4}$alkyl)amino or polyhaloC$_{1-4}$alkyl;

R$^7$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may, whenever possible, optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$), R$^{7a}$, —X$_3$—R$^{7a}$ or R$^{7a}$—C$_{1-4}$alkanediyl-;

R$^{7a}$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$);

R$^8$ represents hydrogen, C$_{1-4}$alkyl optionally substituted with aryl, or aryl;

R$^9$ and R$^{10}$ each independently represent hydrogen; hydroxy; C$_{1-6}$alkyl; C$_{1-6}$alkyloxy; C$_{1-6}$alkylcarbonyl; C$_{1-6}$alkyloxycarbonyl; amino; mono- or di(C$_{1-6}$alkyl)amino; mono- or di(C$_{1-6}$alkyl)aminocarbonyl; —CH(=NR$^{11}$) or R$^7$, wherein each of the aforementioned C$_{1-6}$alkyl groups may optionally and each individually be substituted with one or two substituents each independently selected from hydroxy, C$_{1-6}$alkyloxy, hydroxyC$_{1-6}$alkyloxy, carboxyl, C$_{1-6}$alkyloxycarbonyl, cyano, amino, imino, mono- or di(C$_{1-4}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, or R$^7$; or R$^9$ and R$^{10}$ may be taken together to form a bivalent or trivalent radical of formula

 (d-1)

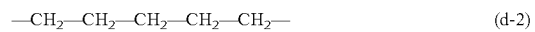 (d-2)

 (d-3)

 (d-4)

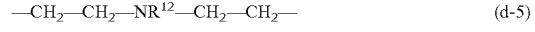 (d-5)

 (d-6)

 (d-7)

R$^{11}$ represents cyano; C$_{1-4}$alkyl optionally substituted with C$_{1-4}$alkyloxy, cyano, amino, mono- or di(C$_{1-4}$alkyl)amino or aminocarbonyl; C$_{1-4}$alkylcarbonyl; C$_{1-4}$alkyloxycarbonyl; aminocarbonyl; mono- or di(C$_{1-4}$alkyl)aminocarbonyl;

R$^{12}$ represents hydrogen or C$_{1-4}$alkyl;

R$^{13}$ and R$^{14}$ each independently represent C$_{1-6}$alkyl optionally substituted with cyano or aminocarbonyl or mono- or di(C$_{1-4}$alkyl)aminocarbonyl, C$_{2-6}$alkenyl optionally substituted with cyano or aminocarbonyl or mono- or di(C$_{1-4}$alkyl)aminocarbonyl, C$_{2-6}$alkynyl optionally substituted with cyano or aminocarbonyl or mono- or di(C$_{1-4}$alkyl)aminocarbonyl;

R$^{15}$ represents C$_{1-6}$alkyl optionally substituted with cyano or aminocarbonyl or mono- or di(C$_{1-4}$alkyl)aminocarbonyl;

R$^{16}$ represents C$_{1-6}$alkyl optionally substituted with cyano or aminocarbonyl or mono- or di(C$_{1-4}$alkyl)aminocarbonyl, or R$^7$;

p is 1 or 2;

aryl represents phenyl or phenyl substituted with one, two, three, four or five substituents each independently selected from halo, hydroxy, mercapto, C$_{1-6}$alkyl, hydroxyC$_{1-6}$alkyl, aminoC$_{1-16}$alkyl, mono or di(C$_{1-6}$alkyl)aminoC$_{1-6}$alkyl, C$_{1-6}$alkylcarbonyl, C$_{3-7}$cycloalkyl, C$_{1-16}$alkyloxy, C$_{1-16}$alkyloxycarbonyl, C$_{1-16}$alkylthio, cyano, nitro, polyhaloC$_{1-6}$alkyl, polyhaloC$_{1-6}$alkyloxy, aminocarbonyl, R$^7$ or —X$_3$—R$^7$.

The present invention also relates to the use of a compound of formula (I), a N-oxide, a pharmaceutically acceptable addition salt, a quaternary amine or a stereochemically isomeric form thereof, for the manufacture of a medicament for the treatment or prevention of HIV infection, in particular for the treatment of HIV infection.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like; $C_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; $C_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; $C_{2-6}$alkanediyl defines straight or branched chain saturated bivalent hydro-carbon radicals having from 2 to 6 carbon atoms such as 1,2-ethanediyl or 1,2-ethylidene, 1,3-propanediyl or 1,3-propylidene, 1,4-butanediyl or 1,4-butylidene, 1,5-pentanediyl or 1,5-pentylidene, 1,6-hexanediyl or 1,6-hexylidene and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; a monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hückel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, tetradecahydroanthracenyl and the like.

Particular examples of monocyclic, bicyclic or tricyclic partially saturated carbocycles are cyclopropenyl, cyclobutenyl, cyclopentenyl, cyclohexenyl, cycloheptenyl, cyclooctenyl, bicyclo[4,2,0]octenyl, cyclononenyl, cyclodecenyl, octahydronaphthalenyl, 1,2,3,4-tetrahydronaphthalenyl, 1,2,3,4,4a,9,9a,10-octahydro-anthracenyl and the like.

Particular examples of monocyclic, bicyclic or tricyclic aromatic carbocycles are phenyl, naphthalenyl, anthracenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydroquinolinyl, octahydroindolyl and the like.

Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like. Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example, the groups defined in halomethyl, 1,1-difluoro-ethyl and the like. In case more than one halogen atoms are attached to an alkyl group within the definition of polyhalomethyl, polyhaloC$_{1-4}$alkyl or polyhaloC$_{1-6}$alkyl, they may be the same or different.

The term heterocycle in the definition of R$^7$ or R$^{7a}$ is meant to include all the possible isomeric forms of the heterocycles, for instance, pyrrolyl comprises 1H-pyrrolyl and 2H-pyrrolyl.

The carbocycle or heterocycle in the definition of R$^7$ or R$^{7a}$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

When any variable (eg. R$^7$, R$^6$) occurs more than one time in any constituent, each definition is independent.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (J) are obviously intended to be embraced within the scope of this invention.

Some of the compounds of formula (I) may also exist in their tautomeric form. Such forms although not explicitly indicated in the above formula are intended to be included within the scope of the present invention. Thus, the present invention includes the following compounds

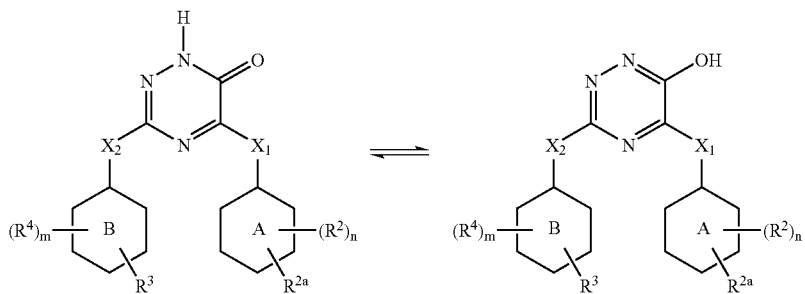

Whenever used hereinafter, the term "compounds of formula (I)" or any subgroup thereof, such as "the compounds of formula (I-1), (I-1-1), (I-1-2), (I-1-3), (I-2), (I-2-1), (I-2-2) or (I-2-3)", is meant to also include their N-oxide forms, their salts, their quaternary amines and their stereochemically isomeric forms. Of special interest are those compounds of formula (I) which are stereochemically pure.

Whenever used hereinbefore or hereinafter that substituents can be selected each independently out of a list of numerous definitions, such as for example for $R^9$ and $R^{10}$, all possible combinations are intended which are chemically possible or which lead to chemically stable molecules.

The present invention also concerns a compound of formula

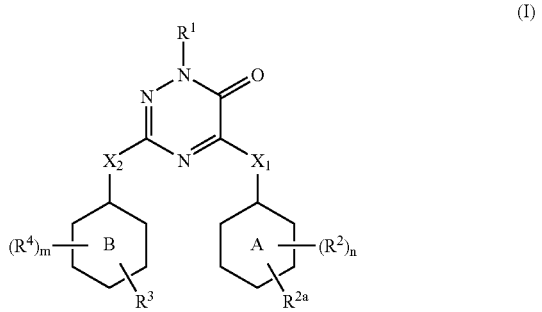

(I)

a N-oxide, a pharmaceutically acceptable addition salt, a quaternary amine or a stereochemically isomeric form thereof, wherein ring A represents phenyl, pyridyl, pyridazinyl, pyrimidinyl or pyrazinyl;

ring B represents phenyl, pyridyl, pyridazinyl, pyrimidinyl or pyrazinyl;

n is 1, 2, 3 and in case ring A represents phenyl, then n may also be 4;

m is 1, 2, 3 and in case ring B represents phenyl, then m may also be 4;

$R^1$ represents hydrogen; aryl; formyl; $C_{1-6}$alkylcarbonyl; $C_{1-6}$alkyloxycarbonyl; $C_{1-6}$alkyl optionally substituted with $R^5$; or $C_{1-6}$alkyloxy$C_{1-6}$alkylcarbonyl substituted with $C_{1-16}$alkyloxycarbonyl;

each $R^2$ independently represents hydrogen; hydroxy; halo; $C_{1-6}$alkyl optionally substituted with one or more substituents each independently selected from halo, cyano, hydroxy or —C(=O)$R^6$; $C_{2-6}$alkenyl optionally substituted with one or more substituents each independently selected from halo, cyano, hydroxy or —C(=O)$R^6$; $C_{2-6}$alkynyl optionally substituted with one or more substituents each independently selected from halo, cyano, hydroxy or —C(=O)$R^6$; $C_{3-7}$cycloalkyl; $C_{1-6}$alkyloxy; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; —S(=O)$_p$$R^6$; —NH—S(=O)$_p$$R^6$; —C(=O)$R^6$; —NHC(=O)H; —C(=O)NHNH$_2$; NHC(=O)$R^6$; C(=NH)$R^6$; or $R^7$;

$R^{2a}$ represents cyano; aminocarbonyl; amino; halo; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; $C_{1-6}$alkyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkynyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; —C(=N—O—R$^8$)—$C_{1-4}$alkyl; $R^7$ or —X$_3$—R$^7$;

$X_1$ represents —NR$^1$—; —NH—NH—; —N=N—; —O—; —C(=O)—; —$C_{1-4}$alkanediyl-; —CHOH—; —S—; —S(=O)$_p$—; —X$_4$—$C_{1-4}$alkanediyl-; —$C_{1-4}$alkanediyl-X$_4$—; or —$C_{1-4}$alkanediyl-X$_4$—$C_{1-4}$alkanediyl-;

$X_2$ represents —NR$^1$—; —NH—NH—; —N=N—; —O—; —C(=O)—; —$C_{1-4}$alkanediyl-; —CHOH—; —S—; —S(=O)$_p$—; —X$_4$—$C_{1-4}$alkanediyl-; —$C_{1-4}$alkanediyl-X$_4$—; or —$C_{1-4}$alkanediyl-X$_4$—$C_{1-4}$alkanediyl-;

$X_3$ represents —NR$^1$—; —NH—NH—; —N=N—; —O—; —C(=O)—; —S—; —S(=O)$_p$—; —X$_{4a}$—$C_{1-4}$alkanediyl-; —$C_{1-4}$alkanediyl-X$_{4b}$—; —$C_{1-4}$alkanediyl-X$_{4a}$—$C_{1-4}$alkanediyl-; or —C(=N—OR$^8$)—$C_{1-4}$alkanediyl-;

$X_4$ represents —NR$^1$—; —NH—NH—; —N=N—; —O—; —C(=O)—; —CHOH—; —S—; or —S(=O)$_p$—;

$X_{4a}$ represents $-NR^1-$; $-NH-NH-$; $-N=N-$; $-C(=O)-$; $-S-$; or $-S(=O)_p-$;

$X_{4b}$ represents $-NH-NH-$; $-N=N-$; $-O-$; $-C(=O)-$; $-S-$; or $-S(=O)_p-$;

$R^3$ represents cyano; aminocarbonyl; amino; halo; $NHR^{13}$; $NR^{13}R^{14}$; $-C(=O)-NHR^{13}$; $-C(=O)-NR^{13}R^{14}$; $-C(=O)-R^{15}$; $-CH=N-NH-C(=O)-R^{16}$; $C_{1-6}$alkyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $C_{1-6}$alkyloxy optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $C_{1-6}$alkyloxy$C_{1-6}$alkyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $C_{2-6}$alkenyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $C_{2-6}$alkynyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $-C(=N-O-R^5)-C_{1-4}$alkyl; $R^7$ or $-X_3-R^7$;

each $R^4$ independently represents hydrogen; hydroxy; halo; $C_{1-6}$alkyl optionally substituted with one or more substituents each independently selected from halo, cyano, hydroxy or $-C(=O)R^6$; $C_{2-6}$alkenyl optionally substituted with one or more substituents each independently selected from halo, cyano, hydroxy or $-C(=O)R^6$; $C_{2-6}$alkynyl optionally substituted with one or more substituents each independently selected from halo, cyano, hydroxy or $-C(=O)R^6$; $C_{3-7}$cycloalkyl; $C_{1-6}$alkyloxy; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; $-S(=O)_pR^6$; $-NH-S(=O)_pR^6$; $-C(=O)R^6$; $-NHC(=O)H$; $-C(=O)NHNH_2$; $NHC(=O)R^6$; $C(=NH)R^6$; or $R^7$;

$R^5$ represents formyl, cyano, aminocarbonyl, mono- or di($C_{1-4}$alkyl)aminocarbonyl, hydroxy, $C_{1-16}$alkylcarbonyl, $C_{1-16}$alkyloxycarbonyl or $C_{1-16}$alkylcarbonyloxy;

$R^6$ represents $C_{1-4}$alkyl, amino, mono- or di($C_{1-4}$alkyl)amino or polyhalo$C_{1-4}$alkyl;

$R^7$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may, whenever possible, optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $-CH(=N-O-R^8)$, $R^{7a}$, $-X_3-R^{7a}$ or $R^{7a}-C_{1-4}$alkanediyl-;

$R^{7a}$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $-CH(=N-O-R^8)$;

$R^8$ represents hydrogen, $C_{1-4}$alkyl optionally substituted with aryl, or aryl;

$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; $-CH(=NR^{11})$ or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$, or $R^7$; or $R^9$ and $R^{10}$ may be taken together to form a bivalent or trivalent radical of formula

| | |
|---|---|
| $-CH_2-CH_2-CH_2-CH_2-$ | (d-1) |
| $-CH_2-CH_2-CH_2-CH_2-CH_2-$ | (d-2) |
| $-CH_2-CH_2-O-CH_2-CH_2-$ | (d-3) |
| $-CH_2-CH_2-S-CH_2-CH_2-$ | (d-4) |
| $-CH_2-CH_2-NR^{12}-CH_2-CH_2-$ | (d-5) |
| $-CH_2-CH=CH-CH_2-$ | (d-6) |
| $=CH-CH=CH-CH=CH-$ | (d-7) |

$R^{11}$ represents cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

$R^{12}$ represents hydrogen or $C_{1-4}$alkyl;

$R^{13}$ and $R^{14}$ each independently represent $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;

$R^{15}$ represents $C_{1-6}$alkyl optionally substituted with cyano or aminocarbonyl;

$R^{16}$ represents $C_{1-6}$alkyl optionally substituted with cyano or aminocarbonyl, or $R^7$;

p is 1 or 2;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino $C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $R^7$ or —$X_3$—$R^7$.

A first interesting embodiment of the present invention are those compounds of formula (I) having the following formula

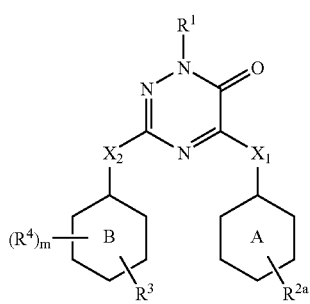
(I-1)

a N-oxide, a pharmaceutically acceptable addition salt, a quaternary amine or a stereochemically isomeric form thereof, wherein $R^1$, $R^{2a}$, $R^3$, $R^4$, m, $X_1$, $X_2$, ring A and ring B are as defined hereinabove.

A second interesting embodiment of the present invention are those compounds of formula (I) having the following formula

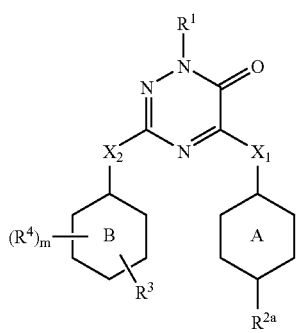
(I-1-1)

a N-oxide, a pharmaceutically acceptable addition salt, a quaternary amine or a stereochemically isomeric form thereof, wherein $R^1$, $R^{2a}$, $R^3$, $R^4$, m, $X_1$, $X_2$, ring A and ring B are as defined hereinabove.

A third interesting embodiment of the present invention are those compounds of formula (I) having the following formula

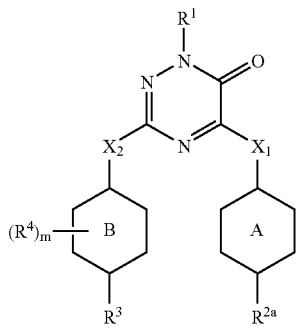
(I-1-2)

a N-oxide, a pharmaceutically acceptable addition salt, a quaternary amine or a stereochemically isomeric form thereof, wherein $R^1$, $R^{2a}$, $R^3$, $R^4$, m, $X_1$, $X_2$, ring A and ring B are as defined hereinabove.

A fourth interesting embodiment of the present invention are those compounds of formula (I) having the following formula

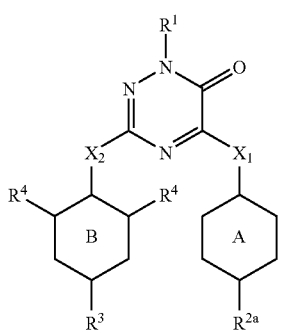
(I-1-3)

a N-oxide, a pharmaceutically acceptable addition salt, a quaternary amine or a stereochemically isomeric form thereof, wherein $R^1$, $R^{2a}$, $R^3$, $R^4$, $X_1$, $X_2$, ring A and ring B are as defined hereinabove with the proviso that $R^4$ is other than hydrogen.

A fifth interesting embodiment of the present invention are those compounds of formula (I) having the following formula

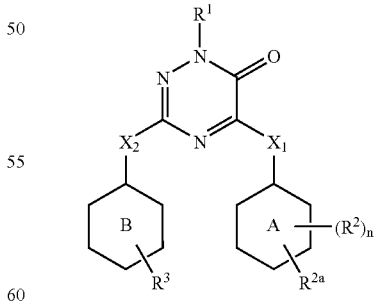
(I-2)

a N-oxide, a pharmaceutically acceptable addition salt, a quaternary amine or a stereochemically isomeric form thereof, wherein $R^1$, $R^{2a}$, $R^2$, $R^3$, $X_1$, $X_2$, n, ring A and ring B are as defined hereinabove.

A sixth interesting embodiment of the present invention are those compounds of formula (I) having the following formula

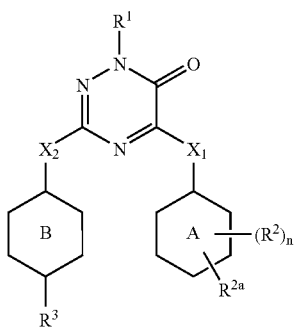

(I-2-1)

a N-oxide, a pharmaceutically acceptable addition salt, a quaternary amine or a stereochemically isomeric form thereof, wherein $R^1$, $R^{2a}$, $R^2$, $R^3$, $X_1$, $X_2$, n, ring A and ring B are as defined hereinabove.

A seventh interesting embodiment of the present invention are those compounds of formula (I) having the following formula

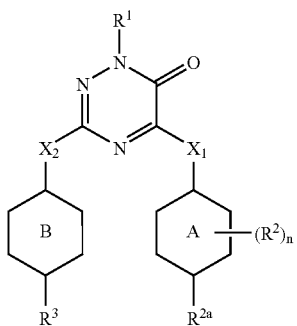

(I-2-2)

a N-oxide, a pharmaceutically acceptable addition salt, a quaternary amine or a stereochemically isomeric form thereof, wherein $R^1$, $R^2$, $R^{2a}$, $R^3$, $X_1$, $X_2$, n, ring A and ring B are as defined hereinabove.

An eighth interesting embodiment of the present invention are those compounds of formula (I) having the following formula

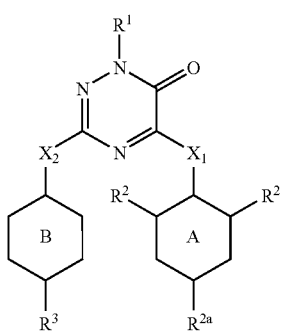

(I-2-3)

a N-oxide, a pharmaceutically acceptable addition salt, a quaternary amine or a stereochemically isomeric form thereof, wherein $R^1$, $R^{2a}$, $R^2$, $R^3$, $X_1$, $X_2$, ring A and ring B are as defined hereinabove with the proviso that $R^2$ is other than hydrogen.

A ninth interesting embodiment of the present invention are those compounds of formula (I), (I-1), (I-1-1), (I-1-2), (I-1-3), (I-2), (I-2-1), (I-2-2), (I-2-3) wherein ring A represents phenyl.

A tenth interesting embodiment of the present invention are those compounds of formula (I), (I-1), (I-1-1), (I-1-2), (I-1-3), (I-2), (I-2-1), (I-2-2), (I-2-3) wherein ring B represents phenyl.

An eleventh interesting embodiment of the present invention are those compounds of formula (I), (I-1), (I-1-1), (I-1-2), (I-1-3), (I-2), (I-2-1), (I-2-2), (I-2-3) wherein ring A and ring B represent phenyl.

A twelfth interesting embodiment of the present invention are those compounds of formula (I), (I-1), (I-1-1), (I-1-2), (I-1-3), (I-2), (I-2-1), (I-2-2), (I-2-3) wherein, whenever the substituents are present, ring A represents phenyl, pyridyl, pyridazinyl, pyrimidinyl or pyrazinyl;

ring B represents phenyl, pyridyl, pyridazinyl, pyrimidinyl or pyrazinyl;

n is 1, 2, 3 and in case ring A represents phenyl, then n may also be 4;

m is 1, 2, 3 and in case ring B represents phenyl, then m may also be 4;

$R^1$ represents hydrogen; aryl; formyl; $C_{1-6}$alkylcarbonyl; $C_{1-6}$alkyloxycarbonyl; $C_{1-6}$alkyl optionally substituted with $R^5$; or $C_{1-6}$alkyloxy$C_{1-6}$alkylcarbonyl substituted with $C_{1-6}$alkyloxycarbonyl;

each $R^2$ independently represents hydrogen; hydroxy; halo; $C_{1-6}$alkyl optionally substituted with one or more substituents each independently selected from halo, cyano, hydroxy or —C(=O)$R^6$; $C_{2-6}$alkenyl optionally substituted with one or more substituents each independently selected from halo, cyano, hydroxy or —C(=O)$R^6$; $C_{2-6}$alkynyl optionally substituted with one or more substituents each independently selected from halo, cyano, hydroxy or —C(=O)$R^6$; $C_{3-7}$cycloalkyl; $C_{1-6}$alkyloxy; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; —S(=O)$_p$$R^6$; —NH—S(=O)$_p$$R^6$; —C(=O)$R^6$; —NHC(=O)H; —C(=O)NHNH$_2$; NHC(=O)$R^6$; C(=NH)$R^6$;

$R^{2a}$ represents cyano; aminocarbonyl; amino; halo; NH$R^{13}$; N$R^{13}R^{14}$; —C(=O)—NH$R^{13}$; —C(=O)—N$R^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, N$R^9R^{10}$, —C(=O)—N$R^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy optionally substituted with one or more substituents each independently selected from halo, cyano, hydroxy, N$R^9R^{10}$, —C(=O)—N$R^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy$C_{1-6}$alkyl optionally substituted with one or more substituents each independently selected from halo, cyano, hydroxy, N$R^9R^{10}$, —C(=O)—N$R^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkenyl optionally substituted with one or more substituents each independently selected from halo, cyano, hydroxy, N$R^9R^{10}$, —C(=O)—N$R^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkynyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl or $-C(=O)-O$-polyhalo$C_{1-6}$alkyl; or $-C(=N-O-R^8)-C_{1-4}$alkyl;

$X_1$ represents $-NR^1-$; $-NH-NH-$; $-N=N-$; $-O-$; $-C(=O)-$; $-C_{1-4}$alkanediyl-; $-CHOH-$; $-S-$; $-S(=O)_p-$; $-X_4-C_{1-4}$alkanediyl-; $-C_{1-4}$alkanediyl-$X_4-$; or $-C_{1-4}$alkanediyl-$X_4-C_{1-4}$alkanediyl-;

$X_2$ represents $-NR^1-$; $-NH-NH-$; $-N=N-$; $-O-$; $-C(=O)-$; $-C_{1-4}$alkanediyl-; $-CHOH-$; $-S-$; $-S(=O)_p-$; $-X_4-C_{1-4}$alkanediyl-; $-C_{1-4}$alkanediyl-$X_4-$; or $-C_{1-4}$alkanediyl-$X_4-C_{1-4}$alkanediyl-;

$X_4$ represents $-NR^1-$; $-NH-NH-$; $-N=N-$; $-O-$; $-C(=O)-$; $-CHOH-$; $-S-$; or $-S(=O)_p-$;

$R^3$ represents cyano; aminocarbonyl; amino; halo; $NHR^{13}$; $NR^{13}R^{14}$; $-C(=O)-NHR^{13}$; $-C(=O)-NR^{13}R^{14}$; $-C(=O)-R^{15}$; $-CH=N-NH-C(=O)-R^{16}$; $C_{1-6}$alkyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl or $-C(=O)-O$-polyhalo$C_{1-6}$alkyl; $C_{1-6}$alkyloxy optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl or $-C(=O)-O$-polyhalo$C_{1-6}$alkyl; $C_{1-6}$alkyloxy$C_{1-6}$alkyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl or $-C(=O)-O$-polyhalo$C_{1-6}$alkyl; $C_{2-6}$alkenyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl or $-C(=O)-O$-polyhalo$C_{1-6}$alkyl; $C_{2-6}$alkynyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl or $-C(=O)-O$-polyhalo$C_{1-6}$alkyl; or $-C(=N-O-R^8)-C_{1-4}$alkyl;

each $R^4$ independently represents hydrogen; hydroxy; halo; $C_{1-6}$alkyl optionally substituted with one or more substituents each independently selected from halo, cyano, hydroxy or $-C(=O)R^6$; $C_{2-6}$alkenyl optionally substituted with one or more substituents each independently selected from halo, cyano, hydroxy or $-C(=O)R^6$; $C_{2-6}$alkynyl optionally substituted with one or more substituents each independently selected from halo, cyano, hydroxy or $-C(=O)R^6$; $C_{3-7}$cycloalkyl; $C_{1-6}$alkyloxy; $C_{1-16}$alkyloxycarbonyl; $C_{1-16}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; $-S(=O)_pR^6$; $-NH-S(=O)_pR^6$; $-C(=O)R^6$; $-NHC(=O)H$; $-C(=O)NHNH_2$; $NHC(=O)R^6$; $C(=NH)R^6$;

$R^5$ represents formyl, cyano, aminocarbonyl, mono- or di($C_{1-4}$ alkyl)aminocarbonyl, hydroxy, $C_{1-16}$alkylcarbonyl, $C_{1-16}$alkyloxycarbonyl or $C_{1-16}$alkylcarbonyloxy;

$R^6$ represents $C_{1-4}$alkyl, amino, mono- or di($C_{1-4}$alkyl)amino or polyhalo$C_{1-4}$alkyl;

$R^8$ represents hydrogen, $C_{1-4}$alkyl, aryl or aryl$C_{1-4}$alkyl;

$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; $-CH(=NR^{11})$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6-$, or $C(=NH)R^6$;

$R^{11}$ represents cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; mono- or di($C_{1-4}$alkyl)aminocarbonyl;

$R^{12}$ represents hydrogen or $C_{1-4}$alkyl;

$R^{13}$ and $R^{14}$ each independently represent $C_{1-6}$alkyl optionally substituted with cyano or aminocarbonyl or mono- or di($C_{1-4}$alkyl)aminocarbonyl, $C_{2-6}$alkenyl optionally substituted with cyano or aminocarbonyl or mono- or di($C_{1-4}$ alkyl)aminocarbonyl, $C_{2-6}$alkynyl optionally substituted with cyano or aminocarbonyl or mono- or di($C_{1-4}$alkyl) aminocarbonyl; in particular $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;

$R^{15}$ represents $C_{1-6}$alkyl optionally substituted with cyano or aminocarbonyl or mono- or di($C_{1-4}$alkyl)aminocarbonyl; in particular $C_{1-6}$alkyl optionally substituted with cyano or aminocarbonyl;

$R^{16}$ represents $C_{1-6}$alkyl optionally substituted with cyano or aminocarbonyl or mono- or di($C_{1-4}$alkyl)aminocarbonyl, or $R^7$; in particular $C_{1-6}$alkyl optionally substituted with cyano or aminocarbonyl, or $R^7$;

p is 1 or 2;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-16}$alkyl, mono or di($C_{1-6}$alkyl)amino$C_{1-6}$alkyl, $C_{1-6}$alkylcarbonyl, $C_{3-7}$cycloalkyl, $C_{1-16}$alkyloxy, $C_{1-16}$alkyloxycarbonyl, $C_{1-16}$alkylthio, cyano, nitro, polyhalo$C_{1-6}$alkyl, polyhalo$C_{1-6}$alkyloxy, aminocarbonyl.

A thirteenth interesting embodiment of the present invention are those compounds of formula (I), (I-1), (I-1-1), (I-1-2), (I-1-3), (I-2-1), (I-2-2), (I-2-3) wherein, whenever the substituents are present, ring A represents phenyl, pyridyl, pyridazinyl, pyrimidinyl or pyrazinyl; in particular phenyl;

ring B represents phenyl, pyridyl, pyridazinyl, pyrimidinyl or pyrazinyl; in particular phenyl;

n is 1, 2, 3 and in case ring A represents phenyl, then n may also be 4;

m is 1, 2, 3 and in case ring B represents phenyl, then m may also be 4;

$R^1$ represents hydrogen; formyl; $C_{1-6}$alkylcarbonyl; $C_{1-6}$alkyloxycarbonyl; or $C_{1-6}$alkyl optionally substituted with $R^5$;

each $R^2$ independently represents hydrogen; hydroxy; halo; $C_{1-6}$alkyl optionally substituted with one or more substituents each independently selected from halo, cyano, hydroxy or $-C(=O)R^6$; $C_{2-6}$alkenyl optionally substituted with one or more substituents each independently selected from halo, cyano, hydroxy or $-C(=O)R^6$; $C_{3-7}$cycloalkyl; $C_{1-16}$alkyloxy; $C_{1-16}$alkyloxycarbonyl; $C_{1-16}$alkylcarbonyloxy; carboxyl; cyano; nitro; amino;

mono- or di($C_{1-6}$alkyl)amino; polyhalo$C_{1-4}$alkyl; polyhalo$C_{1-4}$alkyloxy; polyhalo$C_{1-4}$alkylthio; or —C(=O)$R^6$;

$R^{2a}$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl;

$X_1$ represents —$NR^1$—; —NH—NH—; —N=N—; —O—; —C(=O)—; —$C_{1-4}$alkanediyl-; —CHOH—; —S—; —S(=O)$_p$—; —$X_4$—$C_{1-4}$alkanediyl-; —$C_{1-4}$alkanediyl-$X_4$—; or —$C_{1-4}$alkanediyl-$X_4$—$C_{1-4}$alkanediyl-;

$X_2$ represents —$NR^1$—; —NH—NH—; —N=N—; —O—; —C(=O)—; —$C_{1-4}$alkanediyl-; —CHOH—; —S—; —S(=O)$_p$—; —$X_4$—$C_{1-4}$alkanediyl-; —$C_{1-4}$alkanediyl-$X_4$—; or —$C_{1-4}$alkanediyl-$X_4$—$C_{1-4}$alkanediyl-;

$X_4$ represents —$NR^1$—; —NH—NH—; —N=N—; —O—; —C(=O)—; —CHOH—; —S—; —S(=O)$_p$—;

$R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl;

each $R^4$ independently represents hydrogen; hydroxy; halo; $C_{1-6}$alkyl optionally substituted with one or more substituents each independently selected from halo, cyano, hydroxy or —C(=O)$R^6$; $C_{2-6}$alkenyl optionally substituted with one or more substituents each independently selected from halo, cyano, hydroxy or —C(=O)$R^6$; $C_{3-7}$cycloalkyl; $C_{1-6}$alkyloxy; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; or —C(=O)$R^6$;

$R^5$ represents formyl, cyano, aminocarbonyl, mono- or di($C_{1-4}$alkyl)aminocarbonyl, hydroxy, $C_{1-16}$alkylcarbonyl, $C_{1-16}$alkyloxycarbonyl or $C_{1-16}$alkylcarbonyloxy;

$R^6$ represents $C_{1-4}$alkyl, amino, mono- or di($C_{1-4}$alkyl)amino or polyhalo$C_{1-4}$alkyl;

$R^8$ represents hydrogen or $C_{1-4}$alkyl;

$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; or —CH(=$NR^{11}$), wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio or —C(=O)$R^6$;

$R^{11}$ represents cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl; $C_{1-4}$alkyloxycarbonyl; aminocarbonyl; or mono- or di($C_{1-4}$alkyl)aminocarbonyl;

$R^{12}$ represents hydrogen or $C_{1-4}$alkyl;

$R^{13}$ and $R^{14}$ each independently represent $C_{1-6}$alkyl optionally substituted with cyano or aminocarbonyl, or $C_{2-6}$alkenyl optionally substituted with cyano or aminocarbonyl;

$R^{15}$ represents $C_{1-6}$alkyl optionally substituted with cyano or aminocarbonyl;

$R^{16}$ represents $C_{1-6}$alkyl optionally substituted with cyano or aminocarbonyl;

p is 1 or 2;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy or aminocarbonyl.

A fourteenth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein, whenever the substituents are present, $R^2$ represents hydrogen; and $R^{2a}$ represents cyano; aminocarbonyl; $C_{1-6}$alkyl substituted with cyano or aminocarbonyl; $C_{2-6}$alkenyl substituted with cyano or aminocarbonyl; or $C_{2-6}$alkynyl substituted with cyano or aminocarbonyl; in particular cyano; aminocarbonyl; $C_{1-6}$alkyl substituted with cyano or aminocarbonyl; $C_{2-6}$alkenyl substituted with cyano or aminocarbonyl.

A fifteenth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein, whenever the substituents are present, $R^4$ represents hydrogen; and $R^3$ represents cyano; aminocarbonyl; $C_{1-6}$alkyl substituted with cyano or aminocarbonyl; $C_{2-6}$alkenyl substituted with cyano or aminocarbonyl; or $C_{2-6}$alkynyl substituted with cyano or aminocarbonyl; in particular cyano; aminocarbonyl; $C_{1-6}$alkyl substituted with cyano or aminocarbonyl; $C_{2-6}$alkenyl substituted with cyano or aminocarbonyl.

A sixteenth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein, whenever the substituents are present,
n is 1 or 2;
$R^2$ represents halo; $C_{1-6}$alkyl; or $C_{1-6}$alkyloxy; and
$R^{2a}$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; in particular $R^{2a}$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^6$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; more in particular $R^{2a}$ represents cyano; aminocarbonyl; $C_{1-6}$alkyl substituted with cyano or aminocarbonyl; $C_{2-6}$alkenyl substituted with cyano or aminocarbonyl; or $C_{2-6}$alkynyl substituted with cyano or aminocarbonyl; even more in particular $R^{2a}$ represents cyano; aminocarbonyl; $C_{1-6}$alkyl substituted with cyano or aminocarbonyl; $C_{2-6}$alkenyl substituted with cyano or aminocarbonyl.

A seventeenth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein, whenever the substituents are present,
m is 1 or 2;
$R^4$ represents halo; $C_{1-6}$alkyl; $C_{1-6}$alkyloxy; and
$R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; in particular $R^8$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; more in particular $R^3$ represents cyano; aminocarbonyl; $C_{1-6}$alkyl substituted with cyano or aminocarbonyl; $C_{2-6}$alkenyl substituted with cyano or aminocarbonyl; or $C_{2-6}$alkynyl substituted with cyano or aminocarbonyl; even more in particular $R^3$ represents cyano; aminocarbonyl; $C_{1-6}$alkyl substituted with cyano or aminocarbonyl; $C_{2-6}$alkenyl substituted with cyano or aminocarbonyl.

An eighteenth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein, whenever the substituents are present, $R^2$ represents hydrogen;

$R^{2a}$ represents cyano; aminocarbonyl; $C_{1-6}$alkyl substituted with cyano or aminocarbonyl; $C_{2-6}$alkenyl substituted with cyano or aminocarbonyl; or $C_{2-6}$alkynyl substituted with cyano or aminocarbonyl; in particular cyano; aminocarbonyl; $C_{1-6}$alkyl substituted with cyano or aminocarbonyl; $C_{2-6}$alkenyl substituted with cyano or aminocarbonyl;

m is 1 or 2;

$R^4$ represents halo; $C_{1-6}$alkyl; $C_{1-6}$alkyloxy; and $R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; in particular $R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; more in particular $R^3$ represents cyano; aminocarbonyl; halo; $C_{1-6}$alkyl optionally substituted with cyano or aminocarbonyl; $C_{1-6}$alkyloxy; $C_{2-6}$alkenyl substituted with cyano or aminocarbonyl; or $C_{2-6}$alkynyl substituted with cyano or aminocarbonyl; even more in particular $R^3$ represents cyano; aminocarbonyl; $C_{1-6}$alkyl substituted with cyano or aminocarbonyl; $C_{2-6}$alkenyl substituted with cyano or aminocarbonyl; or $C_{2-6}$alkynyl substituted with cyano or aminocarbonyl; especially cyano; aminocarbonyl; $C_{1-6}$alkyl substituted with cyano or aminocarbonyl; $C_{2-6}$alkenyl substituted with cyano or aminocarbonyl.

A nineteenth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein, whenever the substituents are present, n is 1 or 2;

$R^2$ represents halo; $C_{1-6}$alkyl; or $C_{1-6}$alkyloxy; and $R^{2a}$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; in particular $R^{2a}$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl or —C(=O)—O-polyhalo$C_{1-6}$alkyl; $C_{1-6}$alkyloxy$C_{1-6}$alkyl optionally substituted with one or more substituents each independently selected from halo, cyano, hydroxy, NR$^9$R$^{10}$, —C(=O)—NR$^9$R$^{10}$, —C(=O)—C$_{1-6}$alkyl, —C(=O)—O—C$_{1-6}$alkyl, —C(=O)-polyhaloC$_{1-6}$alkyl or —C(=O)—O-polyhaloC$_{1-6}$alkyl; C$_{2-6}$alkenyl optionally substituted with one or more substituents each independently selected from halo, cyano, hydroxy, NR$^9$R$^{10}$, —C(=O)—NR$^9$R$^{10}$, —C(=O)—C$_{1-6}$alkyl, —C(=O)—O—C$_{1-6}$alkyl, —C(=O)-polyhaloC$_{1-6}$alkyl or —C(=O)—O-polyhaloC$_{1-6}$alkyl; C$_{2-6}$alkynyl optionally substituted with one or more substituents each independently selected from halo, cyano, hydroxy, NR$^9$R$^{10}$, —C(=O)—NR$^9$R$^{10}$, —C(=O)—C$_{1-6}$alkyl, —C(=O)—O—C$_{1-6}$alkyl, —C(=O)-polyhaloC$_{1-6}$alkyl or —C(=O)—O-polyhaloC$_{1-6}$alkyl; more in particular R$^{2a}$ represents cyano; aminocarbonyl; halo; C$_{1-6}$alkyl optionally substituted with cyano or aminocarbonyl; C$_{1-6}$alkyloxy; C$_{2-6}$alkenyl substituted with cyano or aminocarbonyl; or C$_{2-6}$alkynyl substituted with cyano or aminocarbonyl; even more in particular R$^{2a}$ represents cyano; aminocarbonyl; C$_{1-6}$alkyl substituted with cyano or aminocarbonyl; C$_{2-6}$alkenyl substituted with cyano or aminocarbonyl; or C$_{2-6}$alkynyl substituted with cyano or aminocarbonyl; especially cyano; aminocarbonyl; C$_{1-6}$alkyl substituted with cyano or aminocarbonyl; C$_{2-6}$alkenyl substituted with cyano or aminocarbonyl;

R$^4$ represents hydrogen; and

R$^3$ represents cyano; aminocarbonyl; C$_{1-6}$alkyl substituted with cyano or aminocarbonyl; C$_{2-6}$alkenyl substituted with cyano or aminocarbonyl; or C$_{2-6}$alkynyl substituted with cyano or aminocarbonyl; in particular cyano; aminocarbonyl; C$_{1-6}$alkyl substituted with cyano or aminocarbonyl; C$_{2-6}$alkenyl substituted with cyano or aminocarbonyl.

A twentieth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein, whenever the substituents are present, at least one of R$^2$ or R$^4$ is other than hydrogen. In particular, when R$^2$ is other than hydrogen then R$^4$ is hydrogen or when R$^4$ is other than hydrogen then R$^2$ is hydrogen.

A twenty first interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein one or wherever possible more of the following conditions apply:

a) m is 1, 2 or 3, in particular 2 or 3, more in particular 2, even more in particular m is 2 and said two R$^4$ substituents are placed in position 2 and 6 (ortho position) in respect of the X$_2$ linker;

b) m is 1 and R$^4$ is hydrogen; in particular m is 1, R$^4$ is hydrogen and R$^3$ is cyano or aminocarbonyl;

c) X$_1$ is —NR$^1$—, —O—, —C(=O)—, C$_{1-4}$alkanediyl, —CHOH—, —S(=O)$_p$— or S; in particular —NR$^1$—, O or S;

d) n is 1 and R$^2$ is hydrogen; in particular n is 1, R$^2$ is hydrogen and R$^{2a}$ is cyano or aminocarbonyl;

f) n is 1, 2 or 3, in particular 2 or 3, more in particular 2, even more in particular n is 2 and said two R$^2$ substituents are placed in position 2 and 6 (ortho position) in respect of the X$_1$ linker;

g) n is 2 and R$^{2a}$ is cyano; halo; aminocarbonyl; C$_{1-6}$alkyloxy; C$_{1-6}$alkyl optionally substituted with cyano or aminocarbonyl; or C$_{2-6}$alkenyl optionally substituted with cyano or aminocarbonyl; in particular cyano; aminocarbonyl; C$_{1-6}$alkyl optionally substituted with cyano or aminocarbonyl; or C$_{2-6}$alkenyl optionally substituted with cyano or aminocarbonyl;

h) R$^{2a}$ is cyano; aminocarbonyl; C$_{1-6}$alkyl substituted with cyano or aminocarbonyl; or C$_{2-6}$alkenyl substituted with cyano or aminocarbonyl; in particular cyano;

i) m is 2 and R$^3$ is cyano; halo; aminocarbonyl; C$_{1-6}$alkyloxy; C$_{1-6}$alkyl optionally substituted with cyano or aminocarbonyl; or C$_{2-6}$alkenyl optionally substituted with cyano or aminocarbonyl; in particular cyano; aminocarbonyl; C$_{1-6}$alkyl optionally substituted with cyano or aminocarbonyl; or C$_{2-6}$alkenyl optionally substituted with cyano or aminocarbonyl.

A twenty second interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein R$^1$ represents hydrogen or C$_{1-6}$alkyl optionally substituted with R$^5$; in particular R$^1$ represents hydrogen or C$_{1-6}$alkyl optionally substituted with cyano, aminocarbonyl or hydroxy; more in particular R$^1$ is hydrogen.

A twenty third interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein R$^2$ represents hydrogen; halo; C$_{1-6}$alkyl or C$_{1-6}$alkyloxy; in particular hydrogen; halo or C$_{1-6}$alkyl.

A twenty fourth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein R$^{2a}$ represents cyano; aminocarbonyl; halo; C$_{1-6}$alkyl optionally substituted with cyano or aminocarbonyl; C$_{1-6}$alkyloxy; or C$_{2-6}$alkenyl substituted with cyano or aminocarbonyl; in particular cyano; aminocarbonyl; halo; C$_{1-6}$alkyl; or C$_{2-6}$alkenyl substituted with cyano or aminocarbonyl; more in particular cyano; aminocarbonyl; C$_{1-6}$alkyl; or C$_{2-6}$alkenyl substituted with cyano or aminocarbonyl.

A twenty fifth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein R$^3$ represents cyano; aminocarbonyl; halo; C$_{1-6}$alkyl optionally substituted with cyano or aminocarbonyl; C$_{1-6}$alkyloxy; or C$_{2-6}$alkenyl substituted with cyano or aminocarbonyl; in particular cyano; aminocarbonyl; halo; C$_{1-6}$alkyl; or C$_{2-6}$alkenyl substituted with cyano or aminocarbonyl; more in particular cyano; aminocarbonyl; C$_{1-6}$alkyl; or C$_{2-6}$alkenyl substituted with cyano or aminocarbonyl.

A twenty sixth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein R$^4$ represents hydrogen; halo; C$_{1-6}$alkyl or C$_{1-6}$alkyloxy; in particular hydrogen; halo or C$_{1-6}$alkyl.

A twenty seventh interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein X$_1$ represents —NR$^1$—; —O—; —S—; or —S(=O)$_p$—; in particular —NR$^1$—; —O—; or —S—.

A twenty eighth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein X$_2$ represents —NR$^1$—; —O—; —S—; or —S(=O)$_p$—.

A twenty nineth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein $R^5$ represents cyano, aminocarbonyl or hydroxy.

A thirtieth interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein p is 2.

A thirty first interesting embodiment of the present invention are those compounds of formula (I), (I-1), (I-1-1), (I-1-2), (I-1-3) or any subgroup thereof as mentioned hereinabove as interesting embodiment, wherein $R^3$ is $R^7$, $NR^{13}R^{14}$, —C(=O)$R^{15}$, —CH=N—NH—C(=O)$R^{16}$, —C(=O)NHR$^{13}$, —C(=O)NR$^{13}R^{14}$, —C(=N—OR$^8$)—C$_{1-4}$alkyl, C$_{1-6}$alkyl, C$_{1-6}$alkyl substituted with cyano, C$_{1-6}$alkyl substituted twice with cyano, C$_{1-6}$alkyl substituted with NR$^9R^{10}$, C$_{1-6}$alkyl substituted with hydroxy and cyano, C$_{1-6}$alkyl substituted with hydroxy and $R^7$, C$_{1-6}$alkyloxy C$_{1-6}$alkyl, C$_{1-6}$alkyloxy C$_{1-6}$alkyl substituted with cyano, C$_{2-6}$alkenyl substituted with $R^7$, C$_{2-6}$alkenyl substituted with cyano, C$_{2-6}$alkenyl substituted twice with cyano, C$_{2-6}$alkenyl substituted with cyano and $R^7$, C$_{2-6}$alkenyl substituted with cyano and —C(=O)—C$_{1-6}$alkyl, C$_{2-6}$alkenyl substituted with cyano and halo, C$_{2-6}$alkenyl substituted with —C(=O)—NR$^9R^{10}$, C$_{2-6}$alkenyl substituted with halo, C$_{2-6}$alkenyl substituted twice with halo or C$_{2-6}$alkenyl substituted with NR$^9R^{10}$.

A thirty second interesting embodiment of the present invention are those compounds of formula (I), (I-1), (I-1-1), (I-1-2), (I-1-3), (I-2), (I-2-1), (I-2-2), (I-2-3) or any subgroup thereof as mentioned hereinabove as interesting embodiment, wherein,
ring A represents phenyl;
ring B represents phenyl;
n is 1, 2 or 3;
m is 1, 2 or 3;
$R^1$ represents hydrogen; C$_{1-6}$alkyl optionally substituted with $R^5$; in particular hydrogen or C$_{1-6}$alkyl optionally substituted with cyano, aminocarbonyl or hydroxy;
each $R^2$ independently represents hydrogen; halo; C$_{1-6}$alkyl; or C$_{1-6}$alkyloxy;
$R^{2a}$ represents cyano; aminocarbonyl; halo; C$_{1-6}$alkyl optionally substituted with cyano or aminocarbonyl; C$_{1-6}$alkyloxy optionally substituted with cyano or aminocarbonyl; or C$_{2-6}$alkenyl optionally substituted with cyano or aminocarbonyl; in particular cyano; aminocarbonyl; C$_{1-6}$alkyl or C$_{2-6}$alkenyl optionally substituted with cyano or aminocarbonyl;
$X_1$ represents —NR$^1$—; —O—; —S—; or —S(=O)$_p$—; in particular —NR$^1$—; —O—; or —S—;
$X_2$ represents —NR$^1$—; —O—; —S—; or —S(=O)$_p$—;
$R^3$ represents cyano; aminocarbonyl; halo; C$_{1-6}$alkyl optionally substituted with cyano or aminocarbonyl; C$_{1-6}$alkyloxy optionally substituted with cyano or aminocarbonyl; or C$_{2-6}$alkenyl optionally substituted with cyano or aminocarbonyl;
each $R^4$ independently represents hydrogen; halo; C$_{1-6}$alkyl; or C$_{1-6}$alkyloxy;
p is 2.

A tirty third interesting embodiment of the present invention are those compounds of formula (I) or any subgroup thereof as mentioned hereinabove as interesting embodiment, wherein n is 1 and $R^2$ is hydrogen, $R^{2a}$ is cyano, m is 2, and $R^3$ is C$_{1-6}$alkyl substituted with cyano or C$_{2-6}$alkenyl substituted with cyano, preferably cyanoethyl or cyanovinyl.

A thirty fourth interesting embodiment of the present invention are those compounds of formula (I) wherein n is 2, $R^3$ is cyano, m is 1 and $R^4$ is hydrogen, and $R^{2a}$ is C$_{1-6}$alkyl substituted with cyano or C$_{2-6}$alkenyl substituted with cyano, preferably cyanoethyl or cyanovinyl.

A thirty fifth interesting embodiment of the present invention are those compounds of formula (I) wherein $R^{2a}$ is C$_{1-6}$alkyl substituted with cyano or C$_{2-6}$alkenyl substituted with cyano, preferably cyanoethyl or cyanovinyl, more preferably cyanoethyl.

A thirty sixth interesting embodiment of the present invention are those compounds of formula (I) wherein $R^3$ is C$_{1-6}$alkyl substituted with cyano or C$_{2-6}$alkenyl substituted with cyano, preferably cyanoethyl or cyanovinyl, more preferably cyanoethyl.

Preferred compounds of the present invention are compounds 16, 17, 20, 21, 4, 23, 24, 10, 5, 11, 25, 1, 26, 27, 30, 31, 33, 8, 36, 37, 38, 39, 2, 40, 41, 42, 43, 14, 9, 15, 46, 47, 48, 49, 50, 51, 53, 3, 56, 55, 62, 69, 70, 71, 72, 73, 74, 75, 77, 78, 67 (see Table 1 hereinbelow), a N-oxide, a pharmaceutically acceptable addition salt, a quaternary amine or a stereochemically isomeric form thereof.

In general, compounds of formula (I) wherein $R^1$ represents hydrogen, said compounds being represented by formula (I-a), can be prepared by reacting an intermediate of formula (II) wherein $W_1$ represents a suitable leaving group, such as for example halogen, e.g. chloro and the like, with a suitable acid, such as for example acetic acid, optionally in the presence of sodium iodide or water.

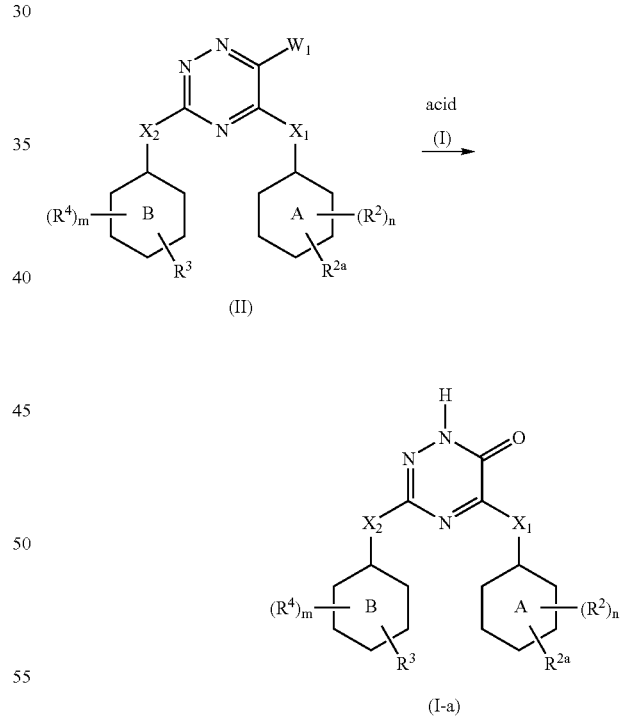

Compounds of formula (I) wherein $R^1$ represents optionally substituted C$_{1-6}$alkyl, said $R^1$ being represented by formula $R^{1a}$ and said compounds being represented by formula (I-b), can be prepared by reacting a compound of formula (I-a) with an intermediate of formula (III), wherein $W_2$ represents a suitable leaving group, such as for example halo, e.g. chloro, bromo and the like, in the presence of a suitable base, such as for example sodium hydride, and a suitable solvent, such as for example tetrahydrofuran.

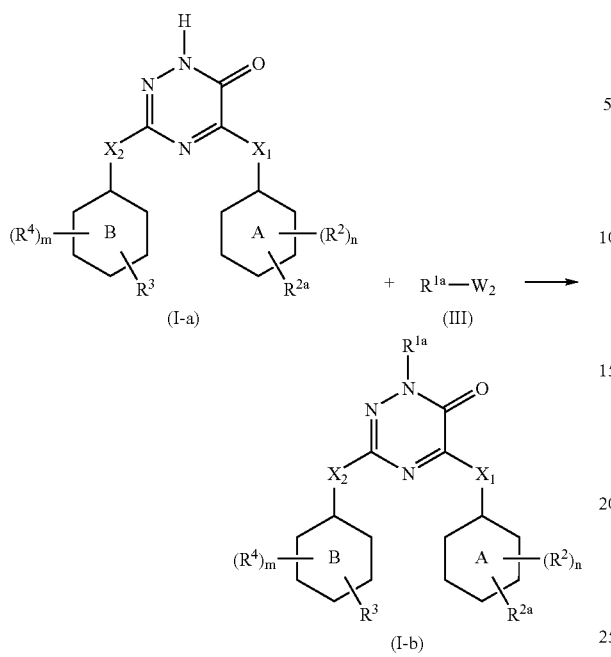

(I-a) + R¹ᵃ—W₂ ⟶ (I-b)

Compounds of formula (I-b) wherein $R^{1a}$ represents $C_{1-6}$alkyl substituted with cyano, said compounds being represented by formula (I-b-1), can be prepared by reacting a compound of formula (I-a) with CH₂=CH—CN in the presence of a suitable catalyst, such as for example Pd(OAc)₂, a suitable ligand, such as for example tri-o-tolylphosphine, a suitable base, such as for example N,N-diethylethanamine, and a suitable solvent, such as for example N,N-dimethylformamide or acetonitrile.

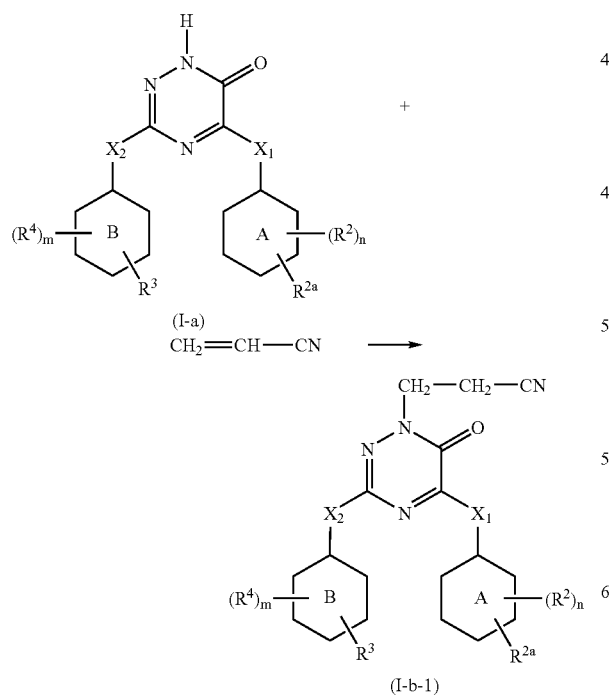

(I-a) + CH₂=CH—CN ⟶ (I-b-1)

Compounds of formula (I) wherein $X_1$ respectively $X_2$ represents S(=O)₂, said compounds being represented by formula (I-c) respectively (I-d), can be prepared by oxidizing a compound of formula (I) wherein $X_1$ respectively $X_2$ represents S, said compounds being represented by formula (I-e) respectively (I-f), in the presence of a suitable oxidizing agent, such as for example H₂O₂, in the presence of a suitable acid, such as for example acetic acid.

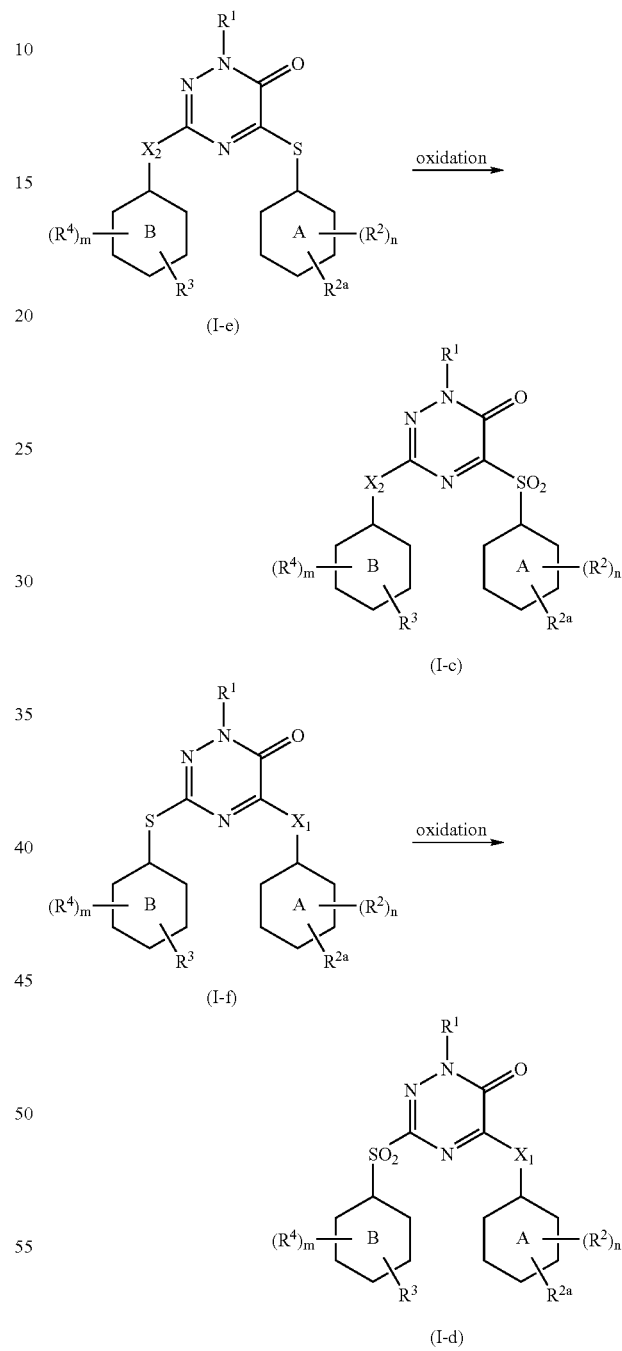

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert. butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^2$, $R^{2a}$, $R^3$ or $R^4$ is $C_{2-6}$alkenyl substituted with aminocarbonyl, can be converted into a compound of formula (I) wherein $R^2$, $R^{2a}$, $R^3$ or $R^4$ is $C_{2-6}$alkenyl substituted with cyano by reaction with $POCl_3$.

Compounds of formula (I) wherein $R^1$ represents $C_{1-6}$alkyloxycarbonyl, can be converted into a compound of formula (I) wherein $R^1$ represents hydrogen, by reaction with a suitable acid, such as for example trifluoroacetic acid.

Compounds of formula (I) wherein $R^2$, $R^{2a}$, $R^3$ or $R^4$ is $C_{2-6}$alkenyl substituted with cyano, can be converted into a compound of formula (I) wherein $R^2$, $R^{2a}$, $R^3$ or $R^4$ is $C_{2-6}$alkyl substituted with cyano by reaction with a suitable reducing agent, such as for example hydrogen, in the presence of a suitable catalyst, such as for example palladium on charcoal, and in the presence of a suitable solvent, such as for example ethanol.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures, e.g. those described in EP 834,507, WO 99/50256, WO 00/27828, WO 01/85700, WO 99/50250, WO 00/27825, WO 01/85700, WO 03/016306, WO 02/078708.

Intermediates of formula (II) wherein $X_2$ represents $NR^1$, said intermediates being represented by formula (II-a), can be prepared by reacting an intermediate of formula (IV) wherein $W_3$ represents a suitable leaving group, such as for example halo, e.g. chloro and the like, with an intermediate of formula (V) in the presence of camphorsulfonic acid (CSA), a suitable solvent, such as for example tetrahydrofuran or an alcohol, e.g. 2-propanol.

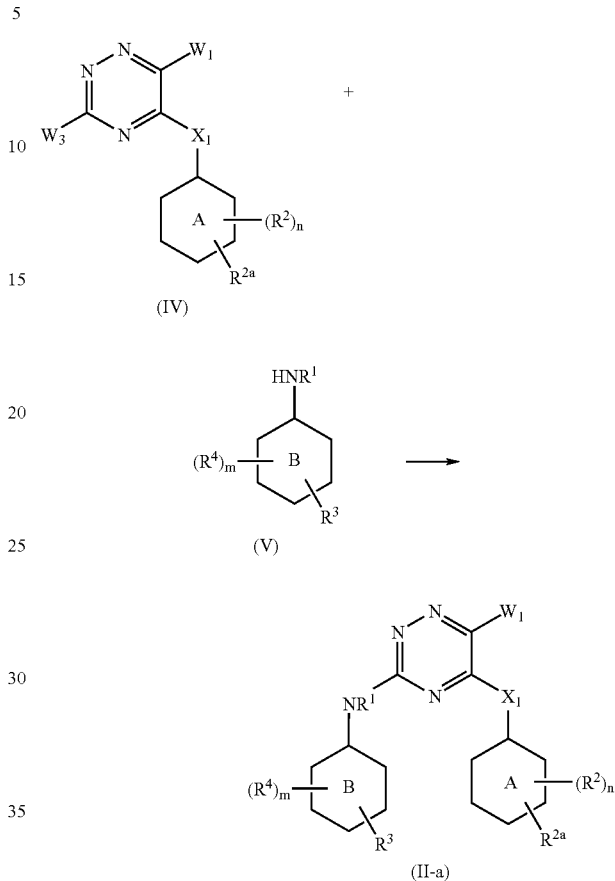

Intermediates of formula (II) wherein $X_2$ represents O, said intermediates being represented by formula (II-b), can be prepared by reacting an intermediate of formula (IV) with an intermediate of formula (VI) in the presence of a suitable base, such as for example $K_2CO_3$, and a suitable solvent, such as for example tetrahydrofuran.

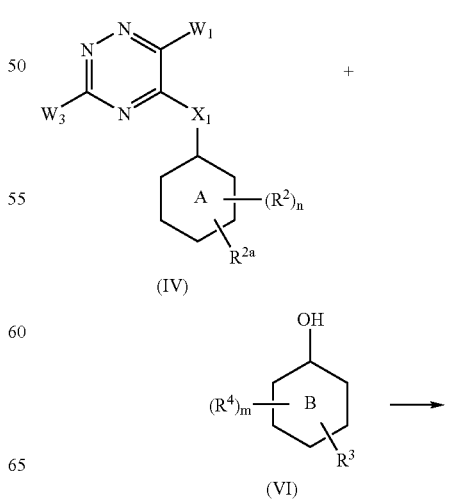

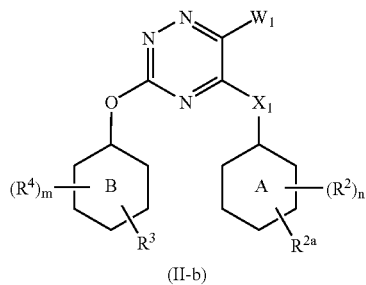

(II-b)

The same reaction procedure can be used to prepare intermediates of formula (II) wherein $X_2$ represents S.

In the above reaction, when $X_1$ represents NH, said NH linker may be protected during the reaction with a suitable protecting group, such as for example tert-butyloxycarbonyl. The protecting group may be removed after the reaction by a suitable deprotection reaction, for example by reaction with trifluoroacetic acid.

Intermediates of formula (II) may be converted into each other. For instance, intermediates of formula (II) wherein $R^4$ is hydrogen, can be converted into an intermediate of formula (II) wherein $R^4$ represents halo, by reaction with a suitable halo-introducing agent, such as for example N-chlorosuccinimide or N-bromosuccinimide, or a combination thereof, in the presence of a suitable solvent, such as for example acetic acid.

Intermediates of formula (II) wherein $R^2$ is hydrogen, can be converted into an intermediate of formula (II) wherein $R^2$ represents halo, by reaction with a suitable halo-introducing agent, such as for example N-chlorosuccinimide or N-bromosuccinimide, or a combination thereof, in the presence of a suitable solvent, such as for example acetic acid.

Intermediates of formula (II) wherein $R^3$ represents iodo, can be converted into an intermediate of formula (II) wherein $R^3$ represents optionally substituted $C_{2-6}$alkenyl, by reaction with optionally substituted $C_{2-6}$alkene in the presence of a suitable catalyst, such as for example Pd(OAc)$_2$, a suitable ligand, such as for example triphenylphospine, a suitable base, such as for example N,N-diethylethanamine, and a suitable solvent, such as for example N,N-dimethylformamide.

Intermediates of formula (II) wherein $R^{2a}$ represents iodo, can be converted into an intermediate of formula (II) wherein $R^{2a}$ represents optionally substituted $C_{2-6}$alkenyl, by reaction with optionally substituted $C_{2-6}$alkene in the presence of a suitable catalyst, such as for example Pd(OAc)$_2$, a suitable ligand, such as for example triphenylphospine, a suitable base, such as for example N,N-diethylethanamine, and a suitable solvent, such as for example N,N-dimethylformamide.

Intermediates of formula (IV) can be prepared by reacting an intermediate of formula (VII), wherein $W_4$ represents a suitable leaving group, such as for example halo, e.g. chloro and the like, with an intermediate of formula (VIII) in the presence of a suitable solvent, such as for example tetrahydrofuran or dichloromethane, and optionally in the presence of a suitable base, such as for example sodium hydride or Na$_2$CO$_3$.

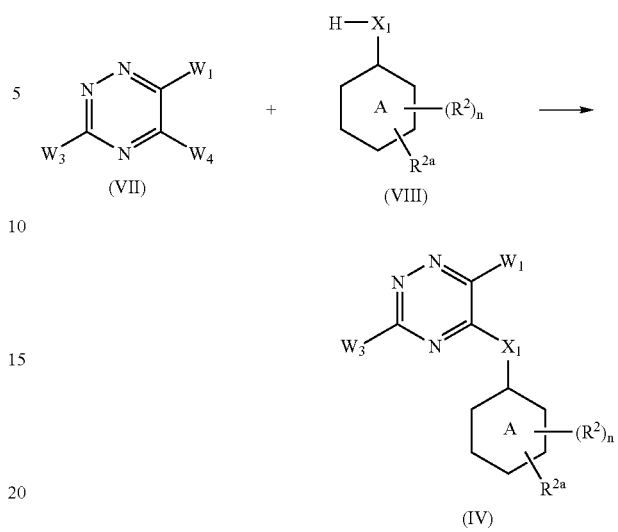

In the above reaction, when $X_1$ represents NH, said NH linker may be protected during the reaction with a suitable protecting group, such as for example tert-butyloxycarbonyl.

Intermediates of formula (VIII) wherein $X_1$—H represents NH$_2$ can be converted into an intermediate wherein $X_1$—H represents NH—C(=O)—O—C(CH$_3$)$_3$, by reaction with di-tert. butyl-dicarbonate in the presence of 4-dimethylaminopyridine.

Intermediates of formula (VII) wherein $W_1$, $W_3$ and $W_4$ represent chloro, said intermediates being represented by formula (VII-a), can be prepared by reacting an intermediate of formula (IX) with POCl$_3$ and PCl$_5$ in the presence of a suitable base, such as for example N,N-diethylaniline.

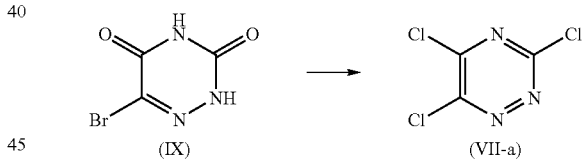

Intermediates of formula (IX) can be prepared by reacting 1,2,4-triazine-3,5 (2H,4H) dione with Br$_2$ in the presence of a suitable solvent, such as for example H$_2$O.

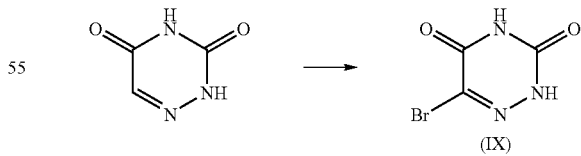

Intermediates of formula (VIII) wherein $X_1$—H represents NH$_2$, said intermediates being represented by formula (VIII-a), can be converted into an intermediate of formula (VIII) wherein $X_1$—H represents OH, said intermediate being represented by formula (VIII-b), by reaction with NaNO$_2$, in the presence of a suitable acid, such as for example HCl, and a suitable solvent, such as for example H$_2$O.

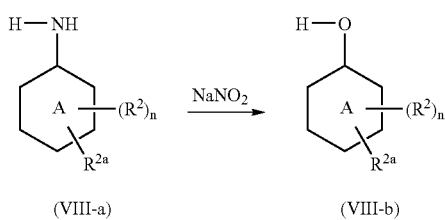

(VIII-a)  (VIII-b)

The same reaction can be used to convert an intermediate of formula (V) wherein $R^1$ is hydrogen, into an intermediate of formula (VI).

Intermediates of formula (V), (VI) or (VIII) wherein $R^3$ or $R^{2a}$ represent iodo or bromo, can be converted into an intermediate of formula (V), (VI) or (VIII) wherein $R^3$ or $R^{2a}$ represent optionally substituted $C_{2-6}$alkenyl, by reaction with optionally substituted $C_{2-6}$alkene in the presence of a suitable catalyst, such as for example $Pd(OAc)_2$, a suitable ligand, such as for example triphenylphospine or tris(2-methylphenyl)phosphine, a suitable base, such as for example N,N-diethylethanamine or N,N-dimethylethanamine, and a suitable solvent, such as for example acetonitrile or N,N-dimethylformamide.

Intermediates of formula (V), (VI) or (VIII) wherein $R^3$ or $R^{2a}$ represent bromo, can be converted into an intermediate of formula (V), (VI) or (VIII) wherein $R^3$ or $R^{2a}$ represent cyano, by reaction with CuCN in the presence of a suitable solvent, such as for example N,N-dimethylformamide.

Intermediates of formula (V), (VI) or (VIII) wherein $R^3$ or $R^{2a}$ represent optionally substituted $C_{2-6}$alkenyl, can be converted into an intermediate of formula (V), (VI) or (VIII) wherein $R^3$ or $R^{2a}$ represent optionally substituted $C_{2-6}$alkyl, by reaction with a suitable reducing agent, such as for example $H_2$, in the presence of a suitable catalyst, such as for example palladium on charcoal, in the presence of a suitable solvent, such as for example an alcohol, e.g. ethanol.

Intermediates of formula (V), (VI) or (VIII) wherein $R^3$ or $R^{2a}$ represent $C_{2-6}$alkenyl substituted with aminocarbonyl, can be converted into an intermediate of formula (V), (VI) or (VIII) wherein $R^3$ or $R^{2a}$ represent $C_{2-6}$alkenyl substituted with cyano, by reaction with $POCl_3$.

Intermediates of formula (V) or (VIII) wherein $X_1$ represents NH, wherein $R^3$ or $R^{2a}$ represent iodo, can be prepared by reacting an intermediate wherein said $R^3$ or $R^{2a}$ represent hydrogen, by reaction with a suitable halogen-introducing agent, such as for example ICl for the introduction of iodo, or $Br_2$ for the introduction of bromo, in the presence of a suitable acid, such as for example acetic acid.

Intermediates of formula (V), (VI) or (VIII) wherein $R^3$ or $R^{2a}$ represent iodo and $R^4$ or $R^2$ represent hydroxy or methoxy, said $R^4$ or $R^2$ substituent being placed in meta position compared to iodo, can be prepared by reacting 2-benzoxazolone with iodine monochloride in the presence of a suitable acid, such as for example acetic acid, followed by reacting the obtained reaction product with di-tert-butylcarbonate, N,N-diethylethanamine, 4-N,N-dimethylaminopyridine in the presence of a suitable solvent, such as for example tetrahydrofuran followed by converting the NH—C(=O)—C($CH_3)_3$ moiety in $NH_2$ by reaction with a suitable acid, such as for example trifluoroacetic acid. When $R^4$ or $R^2$ represent OH, this substituent may be converted into methoxy by reaction with methyl iodide in the presence of a suitable base, such as for example $K_2CO_3$ and a suitable solvent, such as for example tetrahydrofuran.

Intermediates of formula (V), (VI) or (VIII) wherein $R^4$ or $R^2$ represent hydrogen, can be converted into intermediates of formula (V), (VI) or (VIII) wherein $R^4$ or $R^2$ represent halo, by reaction with a suitable halo-introducing agent, such as for example N-chlorosuccinimide or N-bromosuccinimide, or a combination thereof, in the presence of a suitable solvent, such as for example acetonitrile.

Intermediates of formula (V), (VI) or (VIII) wherein $R^3$ or $R^{2a}$ represent halo can be converted into an intermediate of formula (V), (VI) or (VIII) wherein $R^3$ or $R^{2a}$ represent $CH_3$—C(=O)— by reaction with tributyl(1-ethoxyethenyl)stannane in the presence of $Pd(OAc)_2$, $P(o\text{-Tol})_3$, a suitable base, such as for example N,N-diethylethanamine, and a suitable solvent, such as for example acetonitrile.

The intermediates of formula (V), (VI) or (VIII) wherein $R^3$ or $R^{2a}$ represent $CH_3$—C(=O)— can be converted into an intermediate of formula (V), (VI) or (VIII) wherein $R^3$ or $R^{2a}$ represent —C($CH_3$)=CH—CN, by reaction with diethylcyanomethylphosphonate in the presence of a suitable base, such as for example $NaOCH_3$ or tert butylOK, and a suitable solvent, such as for example tetrahydrofuran. Intermediates of formula (V), (VI) or (VIII) wherein $R^3$ or $R^{2a}$ represent bromo, can be converted into an intermediate of formula (V), (VI) or (VIII) wherein $R^3$ or $R^{2a}$ represent $CH_3$—C(=O)—, by reaction with butyl vinyl ether in the presence of a suitable catalyst, such as for example $Pd(OAc)_2$, a suitable ligand, such as for example 1,3-bis(diphenylphosphino)propane, a suitable base, such as for example $K_2CO_3$, and a suitable solvent, such as for example water or N,N-dimethylformamide.

Intermediates of formula (V), (VI) or (VIII) wherein $R^3$ or $R^{2a}$ represent halo can be converted into an intermediate of formula (V), (VI) or (VIII) wherein $R^3$ or $R^{2a}$ represent —C(CN)—C(=O)—O—$C_{1-6}$alkyl, by reaction with CN—$CH_2$—C(=O)—O—$C_{1-6}$alkyl in the presence of $Pd_2(dba)_3$, $P(t\text{-Bu})_3$, $Na_3PO_4$ and a suitable solvent, such as for example toluene. Said intermediates may further be converted into an intermediate of formula (V), (VI) or (VIII) wherein $R^3$ or $R^{2a}$ represent —$CH_2$—CN by reaction with NaCl in the presence of a suitable solvent, such as for example $H_2O$ and dimethylsulfoxide.

Intermediates of formula (V) or (VIII) wherein $NHR^1$ respectively $X_1$—H represent $NH_2$, said intermediates being represented by formula (V-a) or (VIII-a), can be prepared by reducing an intermediate of formula (X) or (XI) with a suitable reducing agent, such as for example $H_2$ in the presence of a suitable catalyst, such as for example palladium on charcoal, in the presence of a suitable solvent, such as for example an alcohol, e.g. ethanol, or by reaction with $SnCl_2$ in the presence of a suitable solvent, such as for example an alcohol, e.g. ethanol.

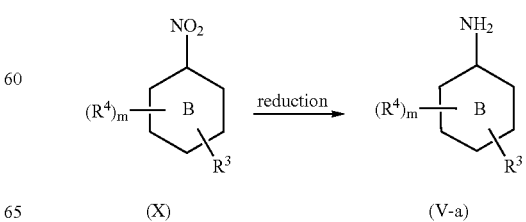

(X)  (V-a)

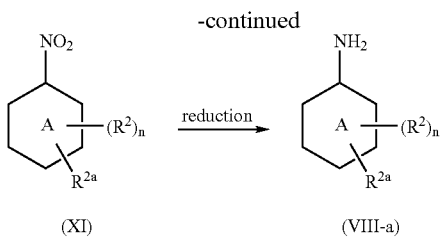

Intermediates of formula (X) or (XI) can be prepared by reacting an intermediate of formula (XII) or (XIII) with $HNO_3$ in the presence of a suitable acid, such as for example $H_2SO_4$.

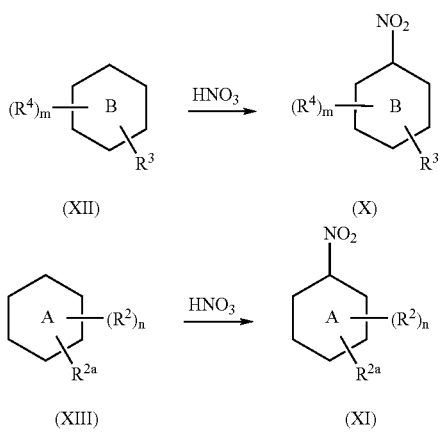

The compounds of formula (I), (I-1), (I-1-1), (I-1-2), (I-1-3), (I-2), (I-2-1), (I-2-2), (I-2-3) show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against drug or multidrug resistant HIV strains, in particular drug or multidrug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and known to the person skilled in the art, in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I) or any subgroup thereof, their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against abovementioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In view of the utility of the compounds of formula (I), there is provided a method of treating mammals, including humans, suffering from or a method of preventing mammals, including humans, to suffer from viral infections, especially HIV infections. Said method comprises the administration, preferably oral administration, of an effective amount of a compound of formula (I) or any subgroup thereof, a N-oxide form, a pharmaceutically acceptable addition salt, a quaternary amine or a possible stereoisomeric form thereof, to mammals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I) or any subgroup thereof, suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated O-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (J) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (J), or amorphous, microcrystalline or crystalline water-soluble polymer, or both, are dispersed more or less evenly in another phase comprising water-soluble polymer, or compound of formula (J), or a solid solution comprising compound of formula (J) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
 a) mixing a compound of formula (I) and an appropriate water-soluble polymer,
 b) optionally blending additives with the thus obtained mixture,
 c) heating and compounding the thus obtained blend until one obtains a homogenous melt,
 d) forcing the thus obtained melt through one or more nozzles; and
 e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 µm, preferably less than 400 µm and most preferably less than 125 µm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (J) or any subgroup thereof can be used alone or in combination with other therapeutic agents, such as anti-virals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (J) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transcriptase inhibitors such as nevirapine (11-cyclopropyl-5,11-di-hydro-4-methyl-6H-dipyrido-[3,2-b: 2',3'-e][1,4]diazepin-6-one), efavirenz, delavirdine, TMC-120, TMC-125, 4-[[4-[[4-(2-cyanoethenyl)-2,6-dimethylphenyl]-amino]-2-pyrimidinyl]amino] benzonitrile (E) and the like; phosphonate reverse transcriptase inhibitors, e.g. tenofovir and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; nucleotide-like reverse transcriptase inhibitors, e.g. tenofovir and the like; ribonucleotide reductase inhibitors, e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses which depend on similar reverse transcriptases for obligatory events in their life cycle.

The following examples are intended to illustrate the present invention.

EXPERIMENTAL PART

Hereinafter, "TFA" is defined as trifluoroacetic acid, "DMF" is defined as N,N-dimethylformamide, "THF" is defined as tetrahydrofuran, [M+H$^+$] is the mass of the protonated compound, "CI-MS" stands for Chemical Ionisation Mass Spectrum.

A. Preparation of the Intermediates

Example A1 a) Preparation of Intermediate 1

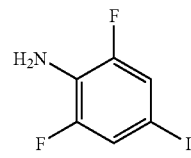

2,6-difluorobenzeneamine (3.0 g, 22.56 mmoles) was dissolved in acetic acid (10 ml). Iodine monochloride (3.581 g, 22.56 mmoles) was added to the solution. The mixture was stirred for 15 minutes at room temperature. After evaporation of the solvent, the residue was treated with an aqueous solution of sodium carbonate. The aqueous solution was extracted with dichloromethane. The organic extract was dried over MgSO₄ and was evaporated. Yield: 95% of intermediate 1.

b) Preparation of Intermediate 2

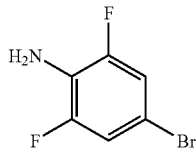

2,6-difluorobenzeneamine (3.0 g, 22.56 mmoles) was dissolved in acetic acid (10 ml). Bromine (1.2 ml) was added to the solution. The mixture was stirred for 15 minutes at room temperature. After evaporation of the solvent, the residue was treated with an aqueous solution of sodium carbonate. The aqueous solution was extracted with dichloromethane. The organic extract was dried over MgSO₄ and was evaporated. Yield: 92% of intermediate 2.

Example A2 a) Preparation of Intermediate 3

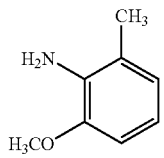

1-methoxy-3-methyl-2-nitro-benzene (25 g, 149.7 mmoles) was dissolved in EtOH (100 ml). 10% Pd/C (2.5 g) was added and the mixture was hydrogenated for 24 hours at room temperature after which period it was filtered on celite. The mixture was evaporated. Yield: 20.02 g (97%) of intermediate 3 (CI-MS: 138 ([M+H]⁺).

b) Preparation of Intermediate 4

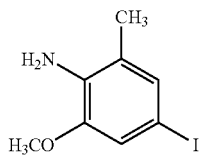

3.3 g of intermediate 3 (24.1 mmoles) were dissolved in acetic acid (15 ml). Iodine monochloride (5.87 g, 36 mmoles) was added. The mixture was stirred at room temperature for 30 minutes and was evaporated. The residue was suspended in an aqueous solution of Na₂CO₃ and was extracted with dichloromethane. After drying the dichloromethane extract on MgSO₄, it was evaporated and the residue was purified on a silica gel column using dichloromethane as eluent. Yield: 0.758 g (13%) of intermediate 4 (CI-MS: 264 [M+H]⁺).

Example A3 a) Preparation of Intermediate 5

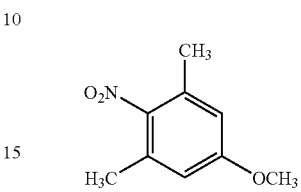

1-methoxy-3,5-dimethylbenzene (4.12 g, 30 mmoles) was dissolved in acetic acid (20 ml). To this solution was added dropwise a mixture of nitric acid fuming (1.26 ml, 30 mmoles) and concentrated sulfuric acid (1.9 ml, 35 mmoles). The mixture was heated at 70° C. for 15 minutes. After cooling, water was added and the mixture was extracted with dichloromethane. The organic extract was dried and evaporated. The resulting residue was purified by column chromatography (30% heptane in CH₂Cl₂). Yield: 1.91 g (35%) of intermediate 5 (CI-MS: 182 [M+H]⁺).

b) Preparation of Intermediate 6

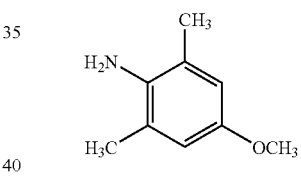

To a solution of intermediate 5 (1.81 g, 10 mmoles) in ethanol (20 ml) was added tin (II) chloride dihydrate (11.51 g, 50 mmoles) and the mixture was refluxed overnight. Upon cooling, ice was added to the reaction mixture followed by basification with 2N NaOH. The mixture was filtered and the filtrate was concentrated under reduced pressure. The aqueous solution was extracted with dichloromethane (4×30 ml). The organic layers were combined and dried over anhydrous MgSO₄ and the solvent was removed under reduced pressure. The residue was purified on a silica gel column chromatography (CH₂Cl₂ as eluent). Yield: 118 g (78%) of intermediate 6 (CI-MS 152 [M+H]⁺).

Example A4 a) Preparation of Intermediate 7 and 8

Intermediate 7

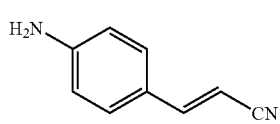

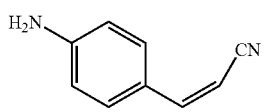

Intermediate 8

To a DMF (20 ml) solution of 4-iodobenzenamine (10 g, 45.20 mmoles) were added acrylonitrile (10 ml), triethylamine (8 ml), palladium acetate (0.540 g, 1.13 mmoles) and triphenylphosphine (0.598 g, 2.26 mmoles). After degassing the reaction mixture, it was flushed with nitrogen and the flask was stopped with a septum. It was then stirred overnight at 100° C. After cooling, the reaction mixture was diluted with dichloromethane. The $CH_2Cl_2$ solution was washed with water (3 times) and was dried over $MgSO_4$ before evaporation. After evaporation, the residue was purified by column chromatography on a silica gel column eluting with $CH_2Cl_2$. Yield: 2.50 g (38%) of intermediate 7 (CI-MS: 145 [M+H]$^+$) and yielding intermediate 8.

b) Preparation of Intermediate 9

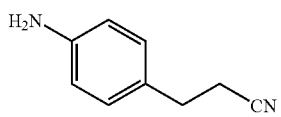

1.58 g of intermediate 7 was dissolved in EtOH (15 ml). 10% Pd/C (100 mg) was added and the mixture was hydrogenated for 24 hours at room temperature after which period it was filtered on celite. The solvent was evaporated: Yield: 1.56 g (97%) of intermediate 9 (CI-MS: 147 ([M+H]$^+$).

c) Preparation of Intermediate 10

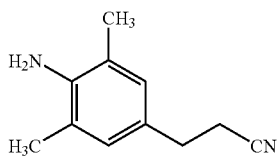

3-(4-amino-3,5-dimethylphenyl)-2-propenenitrile (3.44 g, 20 mmoles) was dissolved in EtOH (20 ml). 10% Pd/C (0.300 g) was added and the mixture was hydrogenated for 24 hours at room temperature after which period it was filtered on celite. The solvent was evaporated. Yield: 3.21 g (92%) of intermediate 10 (CI-MS: 175 ([M+H]$^+$).

d) Preparation of Intermediates 39 and 40

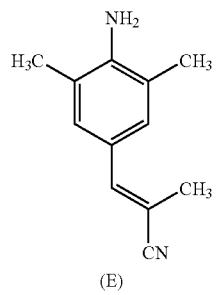

Intermediate 39

(E)

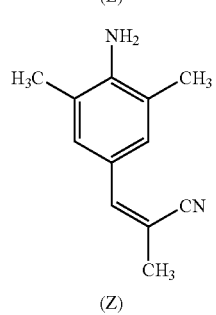

Intermediate 40

(Z)

To a solution of 4-bromo-2,6-dimethylaniline (2.00 g, 10 mmole) in acetonitrile (20 ml) were added methacrylonitrile (2.6 ml, 30 mmole), triethylamine (2.20 ml, 15 mmole), $Pd(OAc)_2$ (0.478 g (47%), 1 mmole), and (o-tol)$_3$P (0.614 g, 2 mmole). After degassing the mixture, it was stirred overnight at 80° C. After cooling, the reaction mixture was diluted with $CH_2Cl_2$ and was washed with an aqueous solution of potassium carbonate. The organic solution was evaporated and the residue was purified by column chromatography (20% EtOAc in heptanes). Yield: 0.384 g of a 1:1 mixture of intermediate 39 and 40 (CI-MS: 187 [M+H]$^+$) and 1.420 g of 4-bromo-2,6-dimethylaniline was recovered.

Example A4A a) Preparation of Intermediate 41

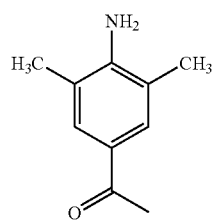

To a solution of 4-bromo-2,6-dimethylaniline (4.00 g, 20 mmole) in DMF (25 ml) and $H_2O$ (3 ml) were added butyl vinyl ether (6.7 ml, 50 mmole), $Pd(OAc)_2$ (0.286 g, 0.60 mmole), 1,3-bis(diphenylphosphino)propane (DPPP, 0.561 g, 1.32 mmole) and $K_2CO_3$. The mixture was degassed for a few minutes before heating overnight. After cooling, $H_2O$ (50 ml) was added to the reaction mixture and then extracted with $CH_2Cl_2$ (3×100 ml). The organic layer was evaporated and the residue dissolved in THF (20 ml). Concentrated HCl (1 ml) was added and the mixture was stirred for 1 hour. The mixture was made alkaline by addition of an aqueous solution of $K_2CO_3$ and was then extracted with $CH_2Cl_2$. After evaporation of the organic layer, the resulting residue was purified by column chromatography (3% EtOAc in $CH_2Cl_2$). Yield: 0.650 g (20%) of intermediate 41 (CI-MS: 164 [M+H]$^+$).

b) Preparation of Intermediates 42 and 43

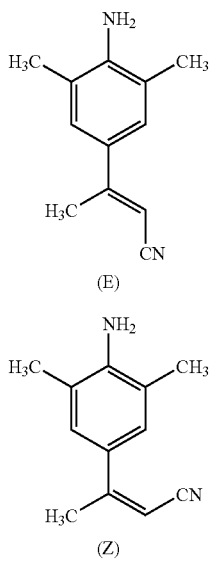

To a solution of diethyl cyanomethylphosphonate (1.470 g, 8.28 mmole) in THF (10 ml) was added t-BuOK (0.947 g, 8.28 mmole) at 5° C. The mixture was allowed to reach room temperature and stirred for 30 minutes. To this mixture was added drop wise a solution of intermediate 41 (0.900 g, 5.52 mmole) in THF (10 ml). The mixture was stirred for 7 days and was evaporated. The residue was partitioned between $H_2O$ and $CH_2Cl_2$. The organic layer was evaporated and the residue purified by column chromatography (20% EtOAc in heptanes). Yield: 0.565 g (55%) of intermediate 42 (CI-MS: 187 [M+H]$^+$) and 0.154 g (15%) of the mixture of intermediates 42 and 43.

Example A4B a) Preparation of Intermediate 44

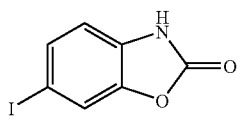

To a solution of 2-benzoxazolone (4.05 g, 30 mmole) in acetic acid (30 ml) was added iodine monochloride (8.71 g, 33.99 mmole). The mixture was stirred for 48 hours. After evaporation, the residue was dissolved in ethyl acetate and the resulting solution was washed with an aqueous solution of potassium carbonate. The organic solution was dried over $MgSO_4$ and was evaporated. Yield: 7.42 g (95%) of intermediate 44 (CI-MS: 262 [M+H]$^+$).

b) Preparation of Intermediate 45

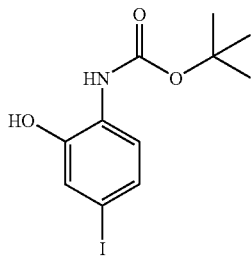

To a THF (100 ml) solution of intermediate 44 (7.42 g, 28.50 mmole) were added triethylamine (4.8 ml, 34.2 mmole), 4-N,N-dimethylaminopyridine (0.704 g, 5.7 mmole) and di-tert-butyldicarbonate (8.11 g, 37.2 mmole). The mixture was stirred for 3 hours before evaporation. The resulting residue was dissolved in methanol (100 ml) and potassium carbonate (4 g, 28.98 mmole) was added to this solution. The mixture was stirred overnight. Acetic acid (4 ml) was added followed by the evaporation. The residue was partitioned between methylene chloride and water. The organic solution was dried over $MgSO_4$ and was evaporated. Yield: 8.46 g of intermediate 45 (CI-MS 336 [M+H]$^+$) which was used further without further purification.

c) Preparation of Intermediate 46

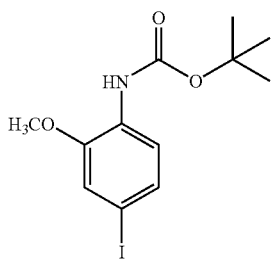

Potassium carbonate (6.67 g, 50.50 mmole) and methyl iodide (10.90 g, 75.75 mmole) were added to a solution of intermediate 45 (8.46 g, 25.5 mmole) in THF (30 ml). The mixture was stirred overnight. After evaporation, the residue was dissolved in $CH_2Cl_2$ and the solution was washed with water. The organic solution was evaporated. The obtained intermediate 46 (CI-MS: 350 [M+H]⁺) was used further without further purification.

d) Preparation of Intermediate 47

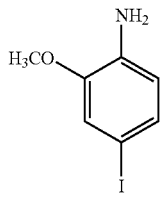

Intermediate 46 obtained under c) dissolved in trifluoroacetic acid (10 ml). After 10 minutes, the mixture was evaporated. The residue was dissolved in CH$_2$Cl$_2$ and the solution was washed with an aqueous solution of potassium carbonate. The organic layer was evaporated and the residue was purified by column chromatography (30% heptanes in CH$_2$Cl$_2$). Yield: 3.87 g of intermediate 47 (CI-MS: 250 [M+H]⁺).

e) Preparation of Intermediate 48

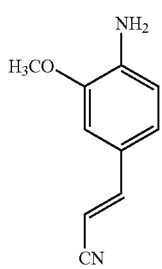

(E)

To a solution of intermediate 47 (8.40 g, 33.73 mmole) in acetonitrile (20 ml) were added acrylonitrile (5.37 g, 101.20 mmole), triethylamine (7.70 ml, 101.50 mmole), dimethylacetamide (4.5 ml), Pd(OAc)$_2$ (0.806 g, 1.69 mmole), and (o-tol)$_3$P (1.027 g, 3.38 mmole). After degassing the mixture, it was stirred overnight at 80° C. After cooling, the reaction mixture was diluted with CH$_2$Cl$_2$ and was washed with an aqueous solution of potassium carbonate. The organic solution was evaporated and the residue was purified by column chromatography (CH$_2$Cl$_2$). Yield: 4.77 g (85%) of intermediate 48 (CI-MS: 175 [M+H]⁺).

f) Preparation of Intermediate 49

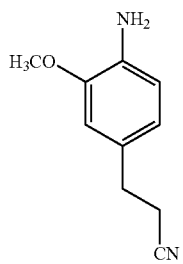

Intermediate 48 (4.63 g, 26.61 mmole) was dissolved in EtOH (50 ml). 10% Pd(C) (1.00 g) was added and the mixture was hydrogenated for 24 hours at room temperature after which period it was filtered on celite. The solvent was evaporated. Yield: 4.55 g (97%) of intermediate 49 (CI-MS: 177 [M+H]⁺).

g) Preparation of Intermediates 50 and 51

Intermediate 50

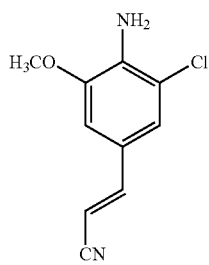

Intermediate 51

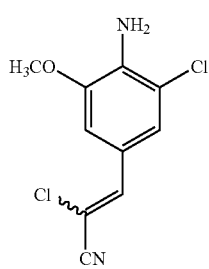

To a solution of intermediate 48 (2.4 g, 13.79 mmole) in acetonitrile (30 ml) was added N-chlorosuccinimide (3.683 g, 27.59 mmole). The mixture was heated at 50° C. for 2 hours and was evaporated. The residue was partitioned between water and CH$_2$Cl$_2$. The organic layer was evaporated and the residue was purified by column chromatography (CH$_2$Cl$_2$).

Yield: 0.420 g (15%) of intermediate 50 (CI-MS: 209 [M+H]$^+$) and 0.840 g (25%) of intermediate 51 (CI-MS: 243 [M+H]$^+$).

h) Preparation of Intermediate 52

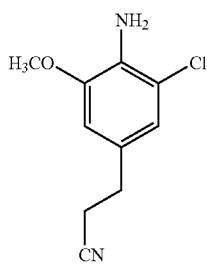

Intermediate 51 (0.840 g, 3.45 mmole) was dissolved in EtOH (10 ml). 10% Pd(C) (0.100 g) was added and the mixture was hydrogenated for 3 hours at room temperature after which period it was filtered on celite. The solvent was evaporated. Yield: 0.280 g (38%) of intermediate 52 (CI-MS: 213 [M+H]$^+$).

Example A5 a) Preparation of Intermediate 11

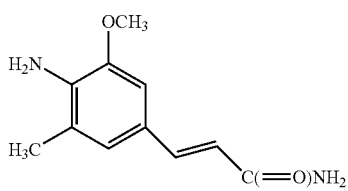

4-Bromo-6-methoxy-2-methylaniline, prepared according to A1b, (7.06 g, 32.4 mmol) was dissolved in 30 ml of acetonitrile. To this solution were added acrylamide (3.45 g, 48.6 mmol), 47% Pd(OAc)$_2$ (0.726 g, 3.24 mol), tris(2-methylphenyl)phosphine (1.9 g, 6.48 mmol), N,N-dimethylethanamine (4.3 ml) and triethylamine (7.5 ml). The mixture was purged with nitrogen for 10 minutes and stirred overnight. The mixture was diluted with 200 ml of dichloromethane, washed three times with 75 ml of water. Aqueous layers were combined and extracted 5 times with 150 ml of ethyl acetate. The dichloromethane and ethylacetate were combined, dried (MgSO$_4$) and filtered. The solvent was evaporated and the residue was stirred in diisopropyl ether followed by filtration. Yield: 5.51 g (83%) of intermediate 11 (CI-MS: 207 [M+H]$^+$).

b) Preparation of Intermediate 12

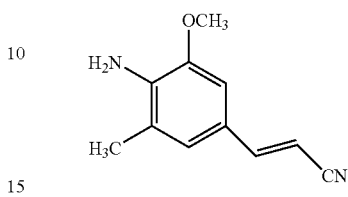

POCl$_3$ (15 ml) was cooled to 0° C. and added in an ice bath to 5.50 g (26.7 mmol) of intermediate 11. The reaction mixture was allowed to reach room temperature and stirred overnight at this temperature. The mixture was added dropwise to 250 ml of diisopropylether while stirring vigorously. The precipitate was filtered and washed with diisopropyl ether. The residue (7.1 g) was added to 150 ml of dichloromethane. An aqueous solution of K$_2$CO$_3$ was added and the dichloromethane layer was separated and evaporated. The residue was purified on a silica gel column (eluent: CH$_2$Cl$_2$). Yield: 3.21 g (64%) of intermediate 12 (CI-MS: 189 [M+H]$^+$).

c) Preparation of Intermediate 13

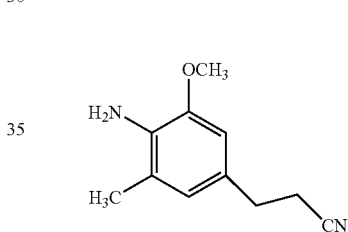

Intermediate 12 (1.70 g, 9.04 mmoles) was dissolved in EtOH (20 ml). 10% Pd/C (0.300 g) was added and the mixture was hydrogenated for 24 hours at room temperature after which period it was filtered on celite. The solvent was evaporated. Yield: 1.57 g (91%) of intermediate 13 (CI-MS: 191 [M+H]$^+$).

Example A6 a) Preparation of Intermediate 14

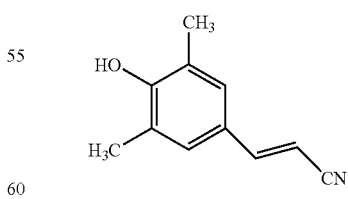

3-(4-amino-3,5-dimethylphenyl)-2-propenenitrile as a hydrochloride salt (4.16 g, 20 mmol) was suspended in 10 ml of water. Concentrated HCl (5 g) followed by 10 g of crushed ice were added. The resulting mixture was cooled to 0° C. and diazotized by adding dropwise a solution of NaNO$_2$ (1.40 g, 20 mmol). After 25 minutes of stirring, the reaction mixture was added dropwise to a solution of 1 ml of concentrated HCl in 20 ml of H₂O at 50° C. and stirred for 30 minutes. Dichloromethane (50 ml) was added and the organic layer was separated. The solvent was evaporated and the residue purified on a silica gel column eluting with dichloromethane. Yield: 1.59 g (48%) of intermediate 14 (CI-MS: 174 [M+H]⁺).

b) Preparation of Intermediate 15

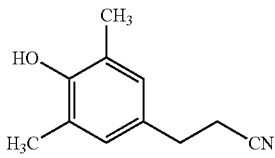

1.2 g (6.9 mmol) of intermediate 14 was dissolved in EtOH (20 ml). 10% Pd/C (0.250 g) was added and the mixture was hydrogenated overnight. After filtration on celite, the solvent was evaporated. Yield: 1.15 g (95%) of intermediate 15 (CI-MS 176 [M+H]⁺).

Example A7 a) Preparation of Intermediate 16

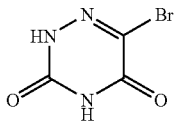

A mixture of 25 g (217 mmoles) of 6-azauracil, bromine (25 ml) and water (250 ml) was stirred at room temperature for 30 hours. The crystalline product was filtered. The filtrate was concentrated and the second precipitate was collected by filtration. The two precipitate fractions were combined and dried. Yield: 38.3 g (92%) of intermediate 16 (5-bromo-6-azauracil) (mp. 231-234° C.).

b) Preparation of Intermediate 17

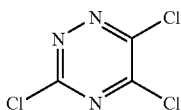

To 18 g (93.75 mmoles) of 5-bromo-6-azauracil (intermediate 16) in 150 ml of phosphorus oxychloride were added 39.2 g (188 mmoles) of phosphorus pentachloride and 38 ml (240 mmoles) of N,N-diethylaniline. The mixture was stirred at 120° C. for 5 hours after which period the excess of solvent was evaporated. The residue was several times extracted with carbon tetrachloride. After evaporation of the solvent, the remaining oily residue was put in the refrigerator where it solidified. Yield: 13 g (78%) of intermediate 17 (3,5,6-trichloro[1,2,4]triazine) (mp. 57-60° C.).

Example A8 a) Preparation of Intermediate 18

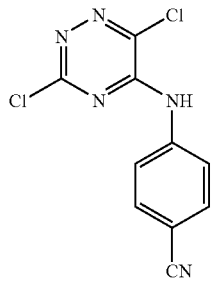

Intermediate 16 (7.68 g, 40 mmoles) was dissolved in phosphorous oxychloride (40 ml). The solution was cooled in an ice bath. Triethylamine (8 ml) was added dropwise. After addition, the bath was removed and the mixture was heated at 70° C. for 30 minutes. A second portion of triethylamine (2 ml) was added. Heating was continued for 30 minutes before the evaporation of the excess of solvent. The residue was dissolved in dry CH₂Cl₂ (60 ml). The resulting solution was cooled in an ice bath. A solution of 4-aminobenzonitrile (4.34 g, 36 mmoles) in dry CH₂Cl₂ (40 ml) was added. After 5 minutes of stirring, the ice bath was removed. A precipitate appeared after 15 minutes of stirring. Triethylamine (ca 3 ml) was added dropwise until the complete dissolution of the precipitate. Ice was added to the solution and the precipitate formed was eliminated by filtration. The filtrate was washed with an aqueous solution of Na₂CO₃. The organic solution was dried over MgSO₄, and was evaporated. Yield: 4.885 g (51%) of intermediate 18 (CI-MS: 266 [M+H]⁺).

b-1) To a solution of 4-aminobenzonitrile (10 g, 84.6 mmoles) in dry THF (80 ml) were added di-tert-butyl-dicarbonate (27.1 g, 127 mmoles) and 4-dimethylaminopyridine (500 mg). The mixture was refluxed for 3 hours. After evaporation, the residue was chromatographed on a silica gel column using CH₂Cl₂ as eluent. After recrystallisation in a mixture of methanol and water, the intermediate was isolated. Yield: 42% of 4-cyanophenylcarbamic acid-1,1-dimethylethylester (CI-MS: 219 [M+H⁺]).

b-2) Preparation of Intermediate 19

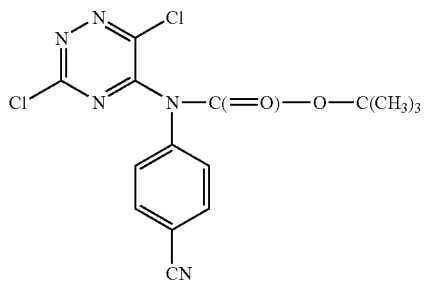

To a solution of 4-cyanophenylcarbamic acid-1,1-dimethylethylester (1.18 g, 5.42 mmoles) in dry THF (20 ml) at 0° C.

was added NaH (0.22 g, 5.42 mmoles). After 5 minutes of stirring at this temperature, a solution of intermediate 17 (1 g, 5.42 mmoles) in THF (10 ml) was added. The mixture was stirred overnight at 50° C. After evaporation of the solvent, water was added and extraction was done with a solution of 7% methanol in dichloromethane. The extract was dried over MgSO$_4$ and was evaporated. The crude intermediate 19 was used further without further purification.

c) Preparation of Intermediate 20

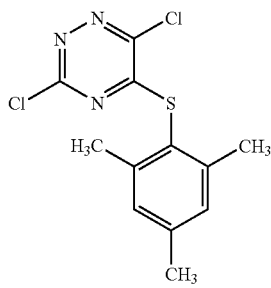

To a solution of intermediate 17 (0.560 g, 3 mmoles) in dry THF (30 ml) at −78° C. under nitrogen atmosphere were added 2,4,6-trimethylthiophenol (3 mmoles) and sodium carbonate (0.318 g, 3 mmoles). The reaction mixture was allowed to reach room temperature and was further stirred overnight at this temperature. The solvent was evaporated. The resulting residue was suspended in water and extracted with dichloromethane. The dichloromethane solution was dried over MgSO$_4$ and evaporated. The residue was chromatographed on a silica gel column using 30% heptane in dichloromethane as eluent. Yield: 68% of intermediate 20 (CI-MS: 300 [M+H]$^+$).

Intermediates with a oxygen linker instead of a sulfur linker were prepared analogously.

d) Preparation of Intermediate 21

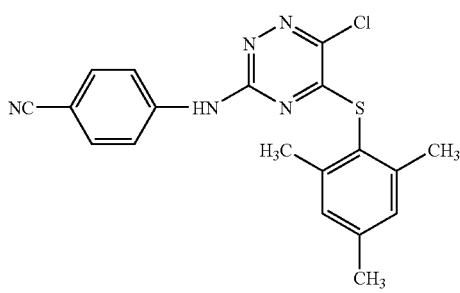

A mixture of intermediate 20 (1 equiv.), 4-aminobenzonitrile (1.5 equiv.), and camphorsulfonic acid (CSA) (0.7 equiv.) was refluxed for 48 hours in THF. After evaporation of the solvent, the residue was suspended in a aqueous solution of Na$_2$CO$_3$ and extracted with CH$_2$Cl$_2$. The dichloromethane solution was dried over MgSO$_4$ and evaporated. The resulting residue was purified by column chromatography using 5% ethyl acetate in dichloromethane as eluent. Yield: 46% of intermediate 21 (mp. 295-296° C.).

Example A9 a) Preparation of Intermediate 22

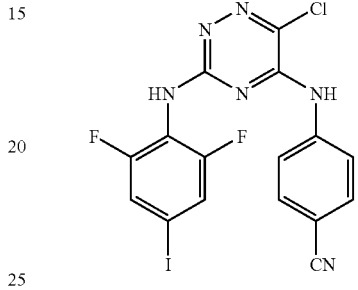

A mixture of intermediate 18 (1 equiv.), 2,6-difluoro-4-iodo-benzeneamine (1.5 equiv.), and camphorsulfonic acid (0.7 equiv.) was refluxed for 20-48 hours in 2-propanol (oil bath 120° C.). The precipitate formed was collected by filtration and was successively washed on the filter with an aqueous solution of Na$_2$CO$_3$, water, and dichloromethane, yielding intermediate 22. In order to increase the yield or to have analytical samples, the 2-propanol and CH$_2$Cl$_2$ filtrate were combined and evaporated. The residue was suspended in an aqueous solution of Na$_2$CO$_3$ and was extracted with CH$_2$Cl$_2$. After drying over MgSO$_4$ and evaporation of the dichloromethane extract, the residue was purified by column chromatography using 10% ethyl acetate in dichloromethane as eluent yielding intermediate 22. Total yield: 49% (CI-MS: 485 [M+H]$^+$).

b) Preparation of Intermediate 24

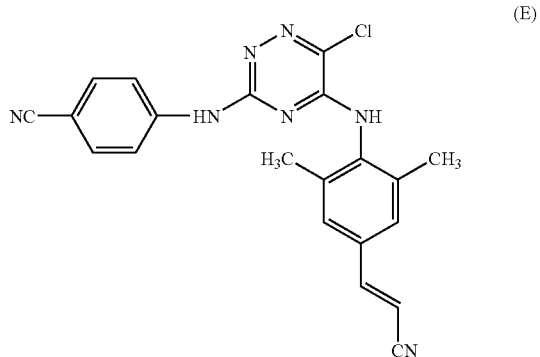

(E)

To a solution of

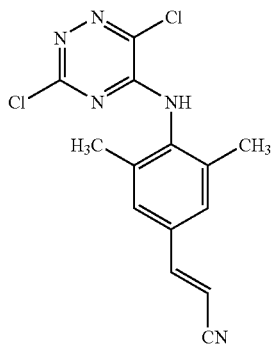

(intermediate 23; prepared according to example A8a) (1 equiv.) in 2-propanol were added 4-aminobenzonitrile (1.5 equiv.) and camphorsulfonic acid (CSA, 0.7 equiv.). The mixture was refluxed for 24 hours at 120° C. After evaporation of the solvent, the residue was suspended in an aqueous solution of $Na_2CO_3$ and extracted with $CH_2Cl_2$. The dichloromethane solution was dried over $MgSO_4$ and evaporated. The resulting residue was purified by column chromatography using 10% ethyl acetate in dichloromethane as eluent. Yield: 65% of intermediate 24 (mp. 281-282° C.).

The above reaction can also be performed in THF as solvent, in that case the reaction mixture was refluxed for 48 hours.

c) Preparation of Intermediate 53

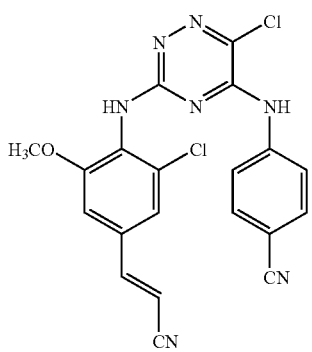

To a solution of the mixture of intermediates 39 and 40 (E+Z isomers, 0.380 g, 2.04 mmole) in THF (20 ml) were added intermediate 18 (0.707 g, 2.66 mmole) and camphorsulfonic acid (0.331 g, 1.43 mmole). The mixture was refluxed overnight in 20 ml of THF (oil bath 130° C.) and was then evaporated. After cooling, the formed precipitate was collected by filtration and then washed successively with an aqueous solution of $K_2CO_3$ (3×), water, $CH_2Cl_2$, and $Et_2O$— Yield: intermediate 53. The supernatant was evaporated and the residue was suspended in an aqueous solution of $K_2CO_3$, and extracted (3 times) with dichloromethane. After evaporation of the dichloromethane extract, the residue was purified by column chromatography (10% ethyl acetate in dichloromethane) to give another amount of intermediate 53. Yield: 0.315 g (27%) of intermediate 53 (CI-MS: 416 [M+H]⁺).

d) Preparation of Intermediate 54

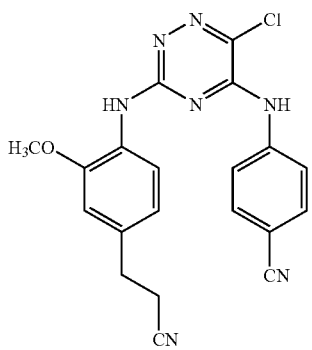

A mixture of intermediate 18 (0.638, 2.398 mmole), intermediate 50 (0.250 g, 1.20 mmole), and camphorsulfonic acid (0.194 g, 0.83 mmole) was refluxed overnight in 10 ml of THF (oil bath 130° C.) and was then evaporated. The residue was suspended in an aqueous solution of $K_2CO_3$, and extracted (3 times) with dichloromethane. After evaporation of the dichloromethane extract, the residue was purified by column chromatography (10% ethyl acetate in dichloromethane). Yield: 0.110 g (19%) of intermediate 54 (CI-MS: 438 [M+H]⁺).

e) Preparation of Intermediate 55

A mixture of intermediate 18 (2.75 g, 10.33 mmole), intermediate 49 (2.182 g, 12.4 mmole), and camphorsulfonic acid (1.624 g, 7.0 mmole) was refluxed overnight in 60 ml of THF (oil bath 130° C.) and was then evaporated. After cooling, the formed precipitate (=intermediate 55.HCl) was collected by filtration and then washed successively with an aqueous solution of K$_2$CO$_3$ (3×), water, CH$_2$Cl$_2$, and Et$_2$O—Yield: 3.40 g (81%) of intermediate 55 (CI-MS: 406 [M+H]$^+$).

Example A10 a) Preparation of Intermediate 25

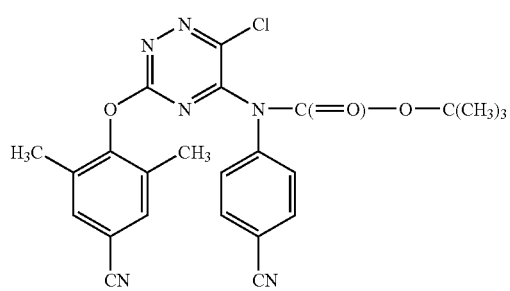

To a solution of intermediate 19 (1 equiv.) in THF were added 4-hydroxy-3,5-dimethylbenzonitrile (1 equiv.) and K$_2$CO$_3$ (1 equiv.). The mixture was heated for 15-30 minutes at 100° C. After evaporation, the residue was dissolved in dichloromethane. The dichloromethane solution was washed with water followed by drying over MgSO$_4$ and evaporation. Yield: intermediate 25 used in the next step.

b) Preparation of Intermediate 26

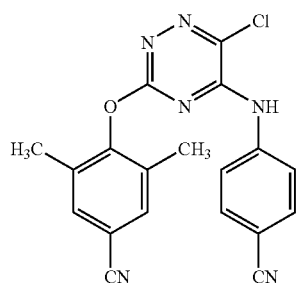

The residue obtained under a) was treated with trifluoroacetic acid (TFA) for 5 minutes. After evaporation of TFA, the residue was dissolved in dichloromethane and triethylamine (5 equiv.) was added. The evaporation of the solvent left a residue which was purified on a silica gel column using 10% EtOAc/90% CH$_2$Cl$_2$ as eluent. Yield: 43% of intermediate 26 (mp. 262-264° C.).

Example A11

Preparation of Intermediate 27

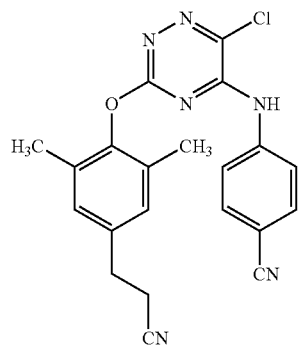

To a solution of intermediate 18 (0.585 g, 2.2 mmol) in THF (10 ml) were added 3-(4-hydroxy-3,5-dimethylphenyl)propanenitrile (0.580 g, 3.3 mmol) and K$_2$CO$_3$ (0.910 g, 6.6 mmol). The mixture was heated at 135° C. for 48 hours and evaporated. Dichloromethane (50 ml) and water (20 ml) were added to the residue. The layers were separated. The organic solution was evaporated and the residue purified by column chromatography (silica, 10% EtOAc in CH$_2$Cl$_2$). Yield: 0.232 g (26%) of intermediate 27 (CI-MS: 405 [M+H]$^+$).

Example A12 a) Preparation of Intermediate 29

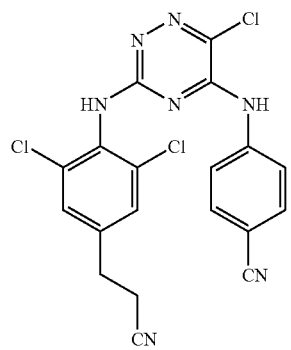

In a two necked flask protected with an aluminium foil and equipped with a condenser was dissolved

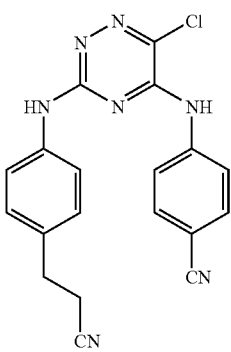

(intermediate 28; prepared according to example A9a), (0.200 g, 0.53 mmole) in acetic acid (5 ml). N-chlorosuccinimide (NCS, 0.212 g, 1.60 mmole) was added. The mixture was degassed, and was heated at 110° C. for 15-30 minutes. After evaporation, the residue was dissolved in ethyl acetate. The solution was washed successively with an aqueous solution of $Na_2CO_3$ and water before drying over $MgSO_4$ and evaporation. The residue was chromatographed on a silica gel column (10% EtOAc in $CH_2Cl_2$). Yield: 17% of intermediate 29 (mp. 254-257° C.).

b) Preparation of Intermediates 30 and 31

Intermediate 30

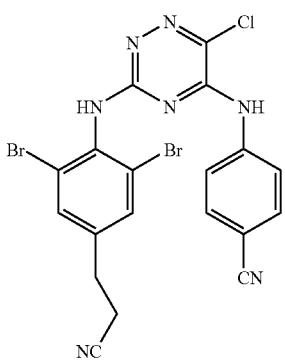

Intermediate 31

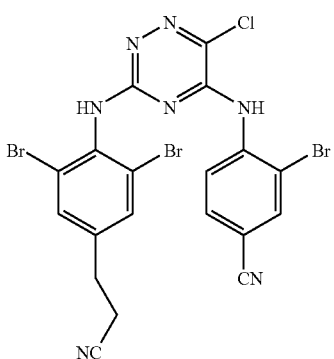

In a two necked flask protected with an aluminium foil and equipped with a condenser was dissolved intermediate 28 (1.502 g, 4 mmol) in acetic acid (15 ml). N-bromosuccinimde (2.140 g, 12 mmol) was added. The mixture was degassed, and was heated at 120° C. for 30 minutes. It was then poured in 250 ml of water. The precipitate collected by filtration was dissolved in 150 ml of ethyl acetate. The resulting solution was washed successively with an aqueous solution of $Na_2CO_3$ and water before drying over $MgSO_4$ and evaporation. The residue was chromatographed on a silica gel column (5% and 10% EtOAc in $CH_2Cl_2$). Yield: 0.491 g (23%) of intermediate 30 (mp. 256-257° C.) and 0.123 g (5%) of intermediate 31 (mp. 273-275° C.).

c) Preparation of Intermediate 32

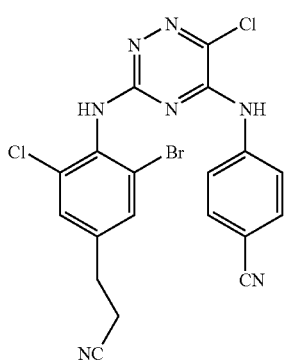

In a two necked flask protected with an aluminium foil and equipped with a condenser was dissolved intermediate 28 (0.207 g, 0.55 mmole) in acetic acid. N-bromosuccinimide (0.198 g, 1.1 mmole) was added. The mixture was degassed, and was heated at 110° C. for 15 minutes. After evaporation, the residue was dissolved in ethyl acetate. The solution was washed successively with an aqueous solution of $Na_2CO_3$ and water before drying over $MgSO_4$ and evaporation. The residue was dissolved in acetic acid in a two necked flask protected with an aluminium foil and equipped with a condenser as above. N-chlorosuccinimide (0.111 g, 0.83 mmole) was added. The mixture was degassed, and was heated at 110° C. for 15 minutes. After evaporation, the residue was dissolved in ethyl acetate. The solution was washed successively with an aqueous solution of $Na_2CO_3$ and water before drying over $MgSO_4$ and evaporation. The residue was purified by chromatography on a silica gel column (10% EtOAc in $CH_2Cl_2$). Yield: 0.110 g (41%) of intermediate 32 (mp. 252-254° C.).

d) Preparation of Intermediate 56

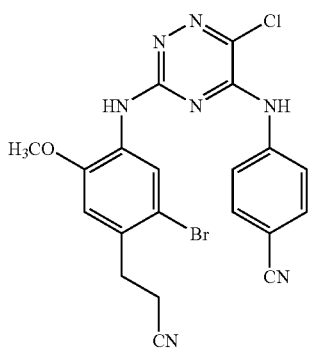

To a solution of intermediate 55.HCl (0.550 g, 1.25 mmole) in acetic acid (10 ml) was added N-bromosuccinimide (0.338 g, 1.88 mmole). The mixture was heated for 2 hours at 120° C. and was then evaporated. Water (20 ml) was added to the residue and the mixture was extracted with ethyl acetate (3×50 ml). The organic layer was dried over MgSO$_4$ and was evaporated. The residue was purified by column chromatography (10% ethyl acetate in CH$_2$Cl$_2$). Yield: 0.109 g (18%) of intermediate 56 (CI-MS: 484 [M+H]$^+$).

e) Preparation of Intermediates 57 and 58

Intermediate 57

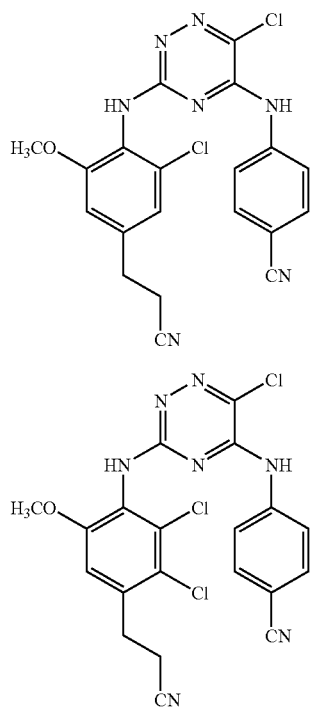

Intermediate 58

To a solution of intermediate 55 (0.500 g, 1.23 mmole) in acetic acid (10 ml) was added N-chlorosuccinimide (0.248 g, 1.85 mmole). The mixture was heated for 1 hour at 120° C. and was then evaporated. Water (20 ml) was added to the residue and the mixture was extracted with ethyl acetate (3×50 ml). The organic layer was dried over MgSO$_4$ and was evaporated. The residue was purified by column chromatography (10% ethyl acetate in CH$_2$Cl$_2$). Yield: 0.200 g of the mixture of intermediates 57 and 58 (CI-MS: 474 [M+H]$^+$).

Example A13 a) Preparation of Intermediate 34

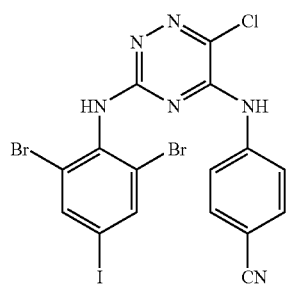

In a two necked flask protected with an aluminium foil and equipped with a condenser was dissolved

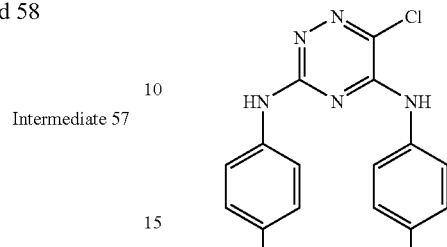

(intermediate 33; prepared according to example A9a) (1 g, 2.23 mmoles) in acetic acid (10 ml). N-bromosuccinimide (NBS, 1.603 g, 8.92 mmoles) was added. The mixture was degassed, and was heated at 120° C. for 15 minutes. After evaporation, the residue was dissolved in ethyl acetate. The solution was washed successively with an aqueous solution of Na$_2$CO$_3$ and water before drying over MgSO$_4$ and evaporation. Yield: Intermediate 34 used in the next step.

b) Preparation of Intermediate 35

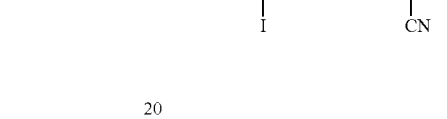

(E+Z)

To a DMF solution of intermediate 34 as obtained in a) were added acrylonitrile (0.12 ml, 1.856 mmole), triethylamine (0.26 ml, 1.856 mmole), palladium acetate (0.0111 g, 0.023 mmole) and triphenylphosphine (0.0123 g, 0.046 mmole). After degassing the reaction mixture, it was flushed with nitrogen and the flask was stopped with a septum. It was then stirred overnight at 100° C. After cooling, the reaction mixture was diluted with dichloromethane. The CH$_2$Cl$_2$ solution was washed with water (3 times) and was dried over MgSO$_4$ before evaporation. After evaporation, the residue was purified by column chromatography on a silica gel column (10% EtOAc in $CH_2Cl_2$). Yield: 6% (from intermediate 33) of intermediate 35 (E+Z) (CI-MS: 530 ([M+H]$^+$).

Example 14 a) Preparation of Intermediate 36

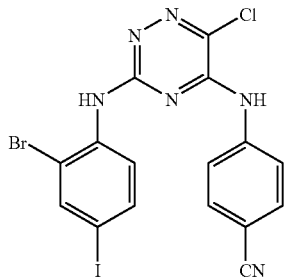

In a two necked flask protected with an aluminium foil and equipped with a condenser was dissolved intermediate 33 (1 g, 2.23 mmoles) in acetic acid. N-bromosuccinimide (0.601 g, 3.345 mmoles) was added. The mixture was degassed, and was heated at 110° C. for 15 minutes. After evaporation, the residue was dissolved in ethyl acetate. The solution was washed successively with an aqueous solution of $Na_2CO_3$, and water before drying over $MgSO_4$ and evaporation. Yield: intermediate 36 used in the next step.

b) Preparation of Intermediate 37

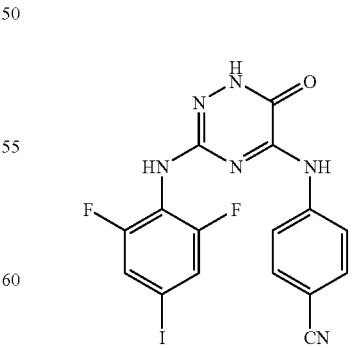

Intermediate 36 as obtained under a) was dissolved in acetic acid in a two necked flask protected with an aluminium foil and equipped with a condenser as above. N-Chlorosuccinimide (0.447 g, 3.345 mmoles) was added. The mixture was degassed, and was heated at 110° C. for 15 minutes. After evaporation, the residue was dissolved in ethyl acetate. The solution was washed successively with an aqueous solution of $Na_2CO_3$ and water before drying over $MgSO_4$ and evaporation. Yield: intermediate 37 used in the next step.

c) Preparation of Intermediate 38

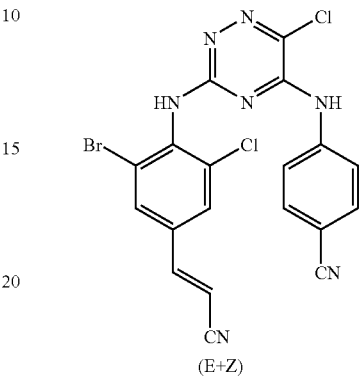

(E+Z)

Intermediate 37 as obtained under b) was dissolved in DMF and acrylonitrile (0.12 ml, 1.856 mmole), triethylamine (0.26 ml, 1.856 mmole), palladium acetate (0.0111 g, 0.023 mmole) and triphenylphosphine (0.0123 g, 0.046 mmole) were added. After degassing the reaction mixture, it was flushed with nitrogen and the flask was stopped with a septum. It was then stirred overnight at 100° C. After cooling, the reaction mixture was diluted with dichloromethane. The $CH_2Cl_2$ solution was washed with water (3 times) and was dried over $MgSO_4$ before evaporation. After evaporation, the residue was purified by column chromatography on a silica gel column (10% EtOAc in $CH_2Cl_2$). Yield: 9% (from intermediate 33) of intermediate 38 (E/Z) (CI-MS: 486 ([M+H$^+$]).

B. Preparation of the Final Compounds

Example B1 a) Preparation of Compound 1

Intermediate 22 (1 equiv.) was dissolved in acetic acid. Sodium iodide (3 equiv.) was added. The mixture was heated at 100-120° C. for 6-48 hours. After evaporation, the residue was purified by column chromatography using 20% EtOAc in CH$_2$Cl$_2$ as eluent. Yield: 18% of compound 1 (mp. 287-290° C.).

b-1) Preparation of Compound 2

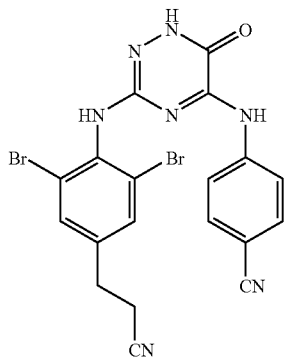

Intermediate 30 (1 equiv.) was dissolved in 95% aqueous acetic acid. The mixture was heated at 120°-150° C. for 6-48 hours. After evaporation, the residue was treated with Et$_3$N in CH$_2$Cl$_2$, and the resulting mixture was then evaporated. The residue was purified by column chromatography on silica gel (7% MeOH in CH$_2$Cl$_2$). Yield: 31% of compound 2 (CI-MS: 514 ([M+H$^+$]; m.p. 339-340° C.).

b-2) Preparation of Compound 3

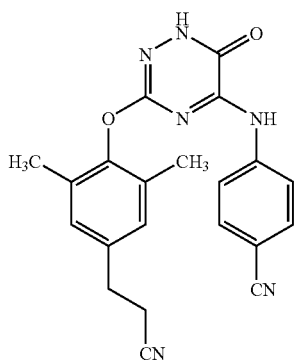

Intermediate 27 was heated for 3 hours at 150° C. in 80% aqueous acetic acid. After evaporation, the residue was treated with Et$_3$N in CH$_2$Cl$_2$ and the mixture evaporated. The residue was treated with CH$_2$Cl$_2$ and the precipitate collected by filtration. The filtrate was washed with CH$_2$Cl$_2$ and a small volume of 7% MeOH in CH$_2$Cl$_2$. Another amount of compound was obtained by evaporation of the supernatant followed by column chromatography of the resulting residue on a silica gel column (20% EtOAc in CH$_2$Cl$_2$). Yield: 55% of compound 3 (mp. 351-352° C.).

b-3) Preparation of Compound 71

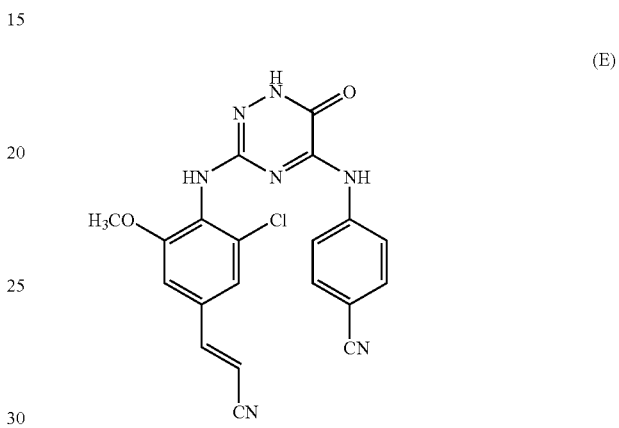

(E)

Intermediate 54 (0.140 g) was dissolved in 80% aqueous acetic acid. The mixture was heated overnight at 150° C. After evaporation, the residue was treated with Et$_3$N in CH$_2$Cl$_2$ and the mixture evaporated. The residue was purified by column chromatography (20% EtOAc in CH$_2$Cl$_2$). Yield: 0.037 g of compound 71 (CI-MS: 420 [M+H]$^+$).

Example B2

Preparation of Compound 5

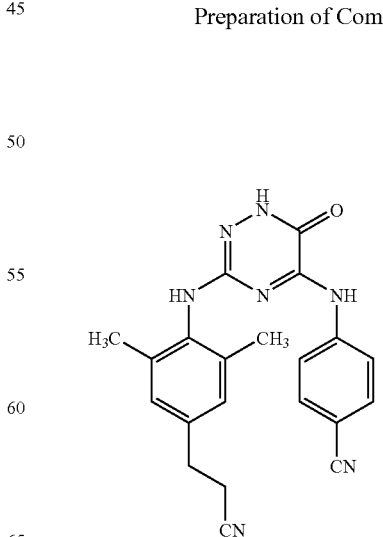

Compound 4 (prepared according to Ex.B1b-1))

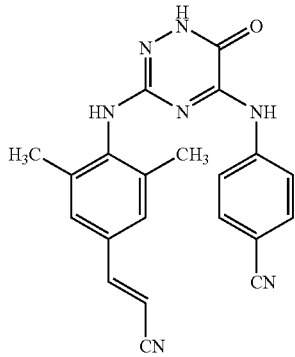

(0.042 g, 0.11 mmole) was dissolved in EtOH. 10% Pd/C was added and the mixture was hydrogenated for 24 hours at room temperature after which period it was filtered on celite. After evaporation of the solvent, the residue was purified on a silica gel column (7% MeOH in CH$_2$Cl$_2$). Yield: 43% of compound 5 (mp. 336-337° C.).

Example B3

Preparation of Compound 7

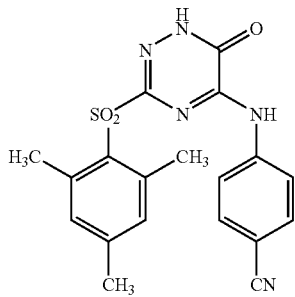

Compound 6 (prepared according to Ex. B1b-1))

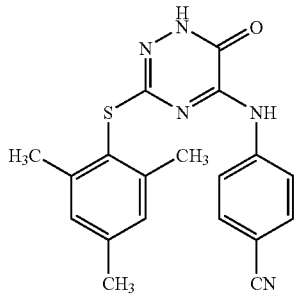

(0.080 g, 0.22 mmole) was dissolved in a solution of 30% hydrogen peroxide in acetic acid (5 ml). The mixture was heated at 100° C. for 3 hours and was evaporated. The residue was purified by column chromatography (20% EtOAc in CH$_2$Cl$_2$). Yield: 0.042 g (48%) of compound 7 (mp. 303-304° C.).

Example B4 a) Preparation of Compound 8

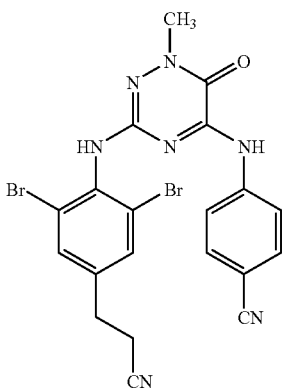

Compound 2 (1 equiv.) was dissolved in dry THF. The mixture was cooled in an ice bath. Sodium hydride (1 equiv.) was added and the mixture was stirred for 5 minutes before addition of an excess of methyl iodide (ca 3 equiv.). The cooling bath was removed and the reaction mixture was allowed to react for 6-24 hours. After completion of the reaction THF was evaporated. The residue was dissolved in CH$_2$Cl$_2$ and the resulting solution was washed with water, dried over MgSO$_4$, and evaporated. The resulting residue was purified by column chromatography using as eluent 10% EtOAc in dichloromethane. Yield: 19% of compound 8 (CI-MS: 528 ([M+H$^+$]).

b) Preparation of Compound 9

Compound 5 was dissolved in dry THF. The solution was cooled in an ice bath. Sodium hydride (1.1 equiv.) was added. The mixture was stirred for 5 minutes before addition of methyl iodide (3 equiv.). The ice bath was removed and after 5 hours of stirring, the mixture was evaporated. The residue was purified on a silica gel column using a solution of 10% EtOAc in CH$_2$Cl$_2$. Yield: compound 9 (mp. 317-320° C.).

c) Preparation of Compound 78

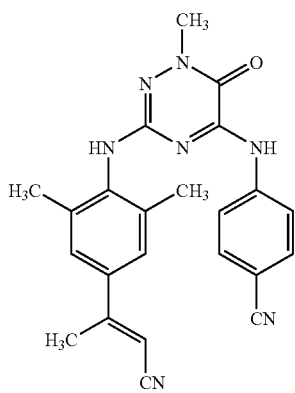

Compound 77 (0.040 g, 0.100 mmole) was dissolved in dry THF (3 ml). The solution was cooled in an ice bath. Sodium hydride (60% dispersed in a mineral oil, 0.004 g, 0.111 mmole) was added. The mixture was stirred for 5 minutes before addition of an excess of methyl iodide (0.5 ml). The ice bath was removed and after 5 hours of stirring, the mixture was evaporated. The residue was purified by preparative thin layer chromatography on silica (10% EtOAc in CH$_2$Cl$_2$). Yield: 0.015 g of compound 78 (CI-MS: 412 [M+H]$^+$)

Example B5

Preparation of Compound 11

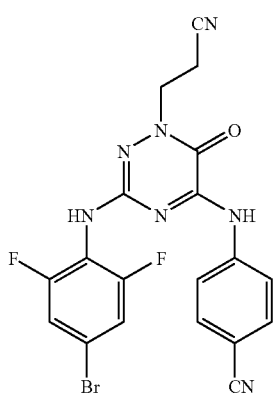

To a DMF (3 ml) solution of (E)

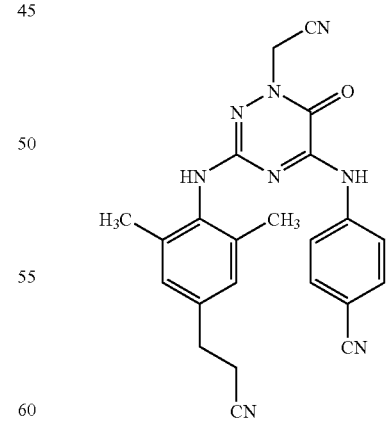

(compound 10; prepared according to example B1a)) (0.111 g, 0.265 mmoles) were added acrylonitrile (0.05 ml), triethylamine (0.04 ml, 0.291 mmole), palladium acetate (0.0128 g, 0.0026 mmole) and tri-o-tolylphosphine (0.0164 g, 0.0052 moles). After degassing the reaction mixture, it was flushed with nitrogen and the flask was stopped with a septum. It was then stirred for 4 days at 120° C. After cooling, the reaction mixture was diluted with dichloromethane. The CH$_2$Cl$_2$ solution was washed with water (3 times) and was dried over MgSO$_4$ before evaporation. After evaporation, the residue was purified by column chromatography on a silica gel column (10% EtOAc in CH$_2$Cl$_2$). Yield: 0.067 g (53%) of compound 11 (mp. 246-247° C.).

Example B6 a-1) Preparation of Compound 12

Compound 5 was dissolved in dry THF. The solution was cooled in an ice bath. Sodium hydride (1.1 equiv.) was added. The mixture was stirred for 5 minutes before addition of Br—CH$_2$—CN (3 equiv.). The ice bath was removed and after 5 hours of stirring, the mixture was evaporated. The residue was purified on a silica gel column using a solution of 10% EtOAc in $CH_2Cl_2$ as eluent Yield: compound 12 (mp. 243-246° C.).

a-2) Preparation of Compound 75

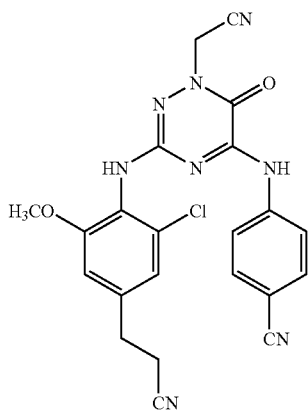

Compound 63 (0.050 g, 0.118 mmole) was dissolved in dry THF (3 ml). The solution was cooled in an ice bath. Sodium hydride (60% dispersed in a mineral oil, 0.006 g, 0.131 mmole) was added. The mixture was stirred for 5 minutes before addition of an excess of Br—$CH_2$—CN (0.5 ml). The ice bath was removed and after 5 hours of stirring, the mixture was evaporated. The residue was purified by preparative thin layer chromatography on silica (10% EtOAc in $CH_2Cl_2$). Yield: 0.030 g of compound 75 (CI-MS: 461 [M+H]$^+$). Compound 60 was prepared accordingly. Compound 57 was prepared accordingly starting from compound 45. The obtained residue was purified by preparative thin layer chromatography on silica (50% EtOAc in heptane). Yield: 0.026 g of compound 57 (m.p. 276-277° C.). This procedure was also used to prepare compound 55 (Yield: 0.027 g; CI-MS: 426 [M+H]$^+$)

b-1) Preparation of Compound 13

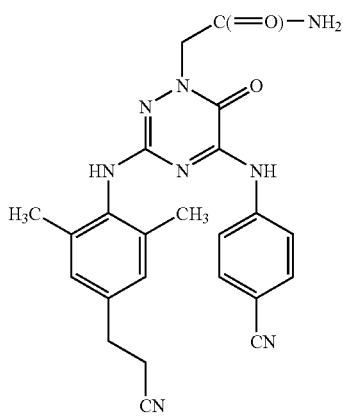

Compound 5 was dissolved in dry THF. The solution was cooled in an ice bath. Sodium hydride (1.1 equiv.) was added. The mixture was stirred for 5 minutes before addition of I—$CH_2$—C(=O)$NH_2$ (3 equiv.). The ice bath was removed and after 5 hours of stirring, the mixture was evaporated. The residue was purified on a silica gel column using a solution of 80% EtOAc in $CH_2Cl_2$ as eluent Yield: compound 13 (mp. 289-291° C.).

b-2) Preparation of Compound 76

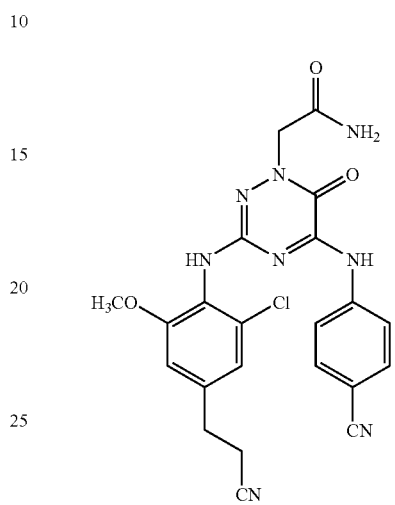

Compound 63 (0.050 g, 0.118 mmole) was dissolved in dry THF (3 ml). The solution was cooled in an ice bath. Sodium hydride (60% dispersed in a mineral oil, 0.006 g, 0.131 mmole) was added. The mixture was stirred for 5 minutes before addition of I—$CH_2$—C(=O)—$NH_2$ (0.044 g, 0.237 mmole). The ice bath was removed and after 5 hours of stirring, the mixture was evaporated. The residue was treated with 7% MeOH in $CH_2Cl_2$. The precipitate was collected by filtration and was washed successively with $H_2O$, and 7% MeOH in $CH_2Cl_2$. Yield: 0.013 g of compound 76 (CI-MS: 479 [M+H]$^+$).

c-1) Preparation of Compound 14

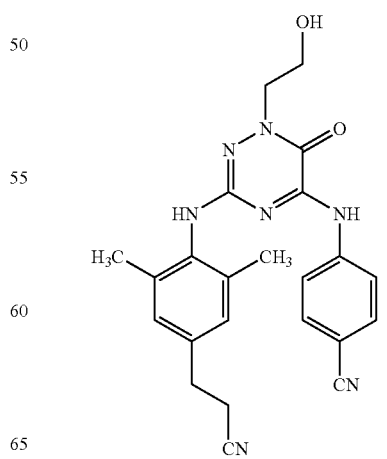

Compound 5 was dissolved in dry THF. The solution was cooled in an ice bath. Sodium hydride (6 equiv.) was added. The mixture was stirred for 5 minutes before addition of an excess of iodoethanol. The ice bath was removed and after 5 hours of stirring, the mixture was evaporated. The residue was purified on a silica gel column using a solution of 60% EtOAc in $CH_2Cl_2$ as eluent. Yield: compound 14 (CI-MS 430 ([M+H$^+$]).

c-2) Preparation of Compound 74

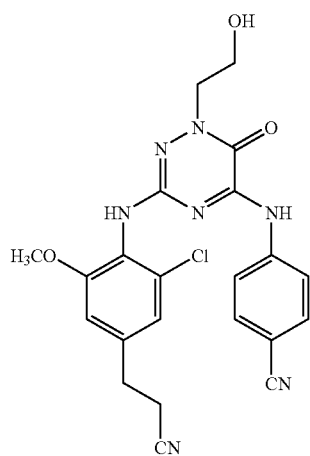

Compound 63 (0.050 g, 0.118 mmole) was dissolved in dry THF (3 ml). The solution was cooled in an ice bath. Sodium hydride (60% dispersed in a mineral oil, 0.006 g, 0.131 mmole) was added. The mixture was stirred for 5 minutes before addition of an excess of 2-iodoethanol (0.5 ml) and another amount of sodium hydride (0.030 g, 0.655 mmole). The ice bath was removed and after 5 hours of stirring, the mixture was evaporated. The residue was purified by preparative thin layer chromatography on silica (60% EtOAc in $CH_2Cl_2$). Yield: 0.029 g of compound 74 (CI-MS: 466 [M+H]$^+$).

Compound 70 was prepared accordingly starting from compound 3. The obtained residue was purified by preparative thin layer chromatography on silica (45% EtOAc in $CH_2Cl_2$). Yield: 0.012 g of compound 70 (CI-MS: 431 [M+H]$^+$). This procedure was also used to prepare compound 61 (Yield: 0.012 g; CI-MS: 429 [M+H]$^+$)

d-1) Preparation of Compound 15

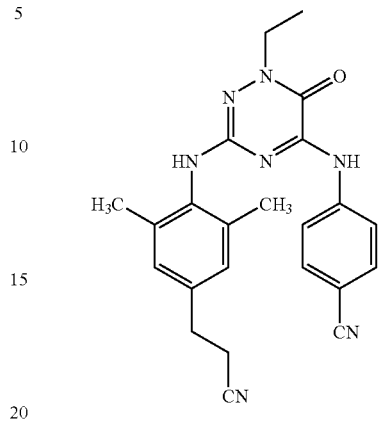

Compound 5 was dissolved in dry THF. The solution was cooled in an ice bath. Sodium hydride (1.1 equiv.) was added. The mixture was stirred for 5 minutes before addition of I—$CH_2$—$CH_3$ (3 equiv.). The ice bath was removed and after 5 hours of stirring, the mixture was evaporated. The residue was purified on a silica gel column using a solution of 10% EtOAc in $CH_2Cl_2$ as eluent. Yield: compound 15 (mp. 243-245° C.).

d-2) Preparation of Compound 73

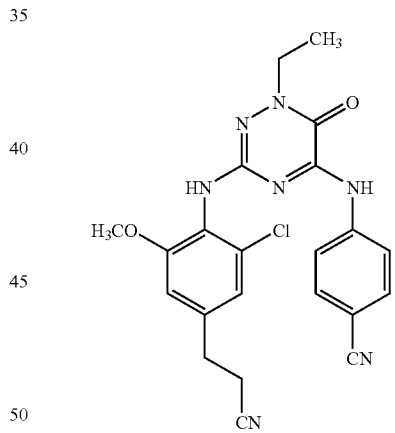

Compound 63 (0.050 g, 0.118 mmole) was dissolved in dry THF (3 ml). The solution was cooled in an ice bath. Sodium hydride (60% dispersed in a mineral oil, 0.006 g, 0.131 mmole) was added. The mixture was stirred for 5 minutes before addition of an excess of ethyl iodide (0.5 ml). The ice bath was removed and after 5 hours of stirring, the mixture was evaporated. The residue was purified by preparative thin layer chromatography on silica (10% EtOAc in $CH_2Cl_2$). Yield: 0.013 g of compound 73 (CI-MS: 450 [M+H]$^+$) as a solid.

Table 1 lists the compounds (Co. No.) that were prepared according to one of the above Examples (Ex.). The compounds were characterized by their melting point (mp.) or protonated mass ([M+H$^+$]).

TABLE 1
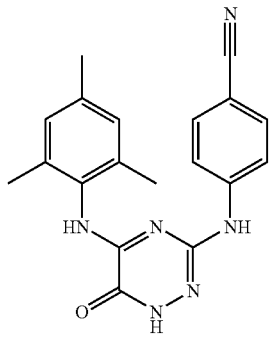
Co. No. 16; Ex. B1a); 347[M + H⁺]
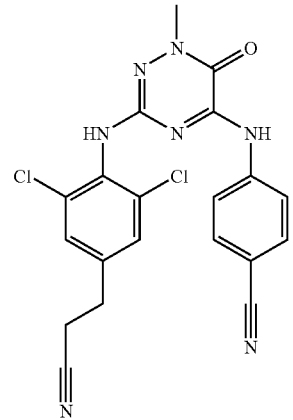
Co. No. 37; Ex. B4a); 440[M + H⁺]
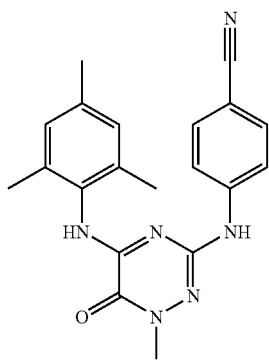
Co. No. 17; Ex. B4a); 301[M + H⁺]
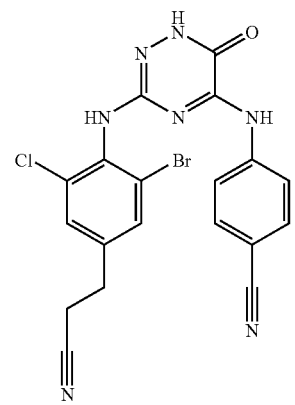
Co. No. 38; Ex. B1b-1); mp. 327-328° C.
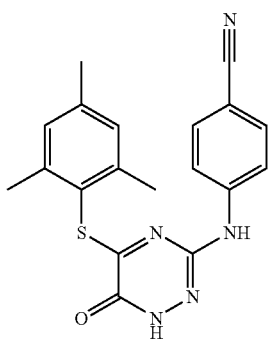
Co. No. 18; Ex. B1a); 262-263° C.
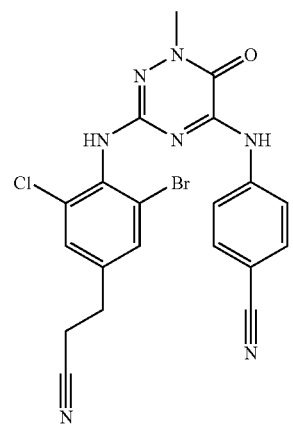
Co. No. 39; Ex. B4a); 484[M + H⁺]

TABLE 1-continued
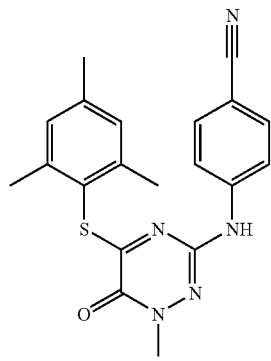
Co. No. 19; Ex. B4a); 378[M + H⁺]
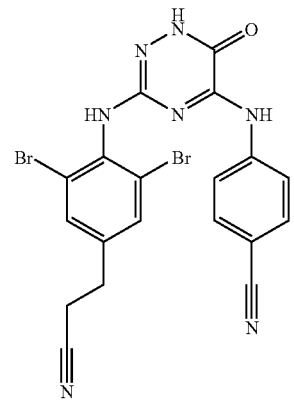
Co. No. 2; Ex. B1b-1); mp. 339-340° C.
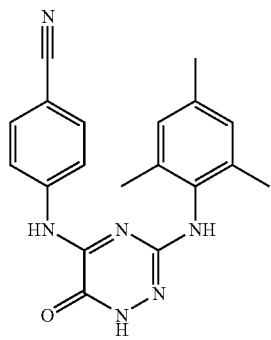
Co. No. 20; Ex. B1a); mp. 338-339° C.
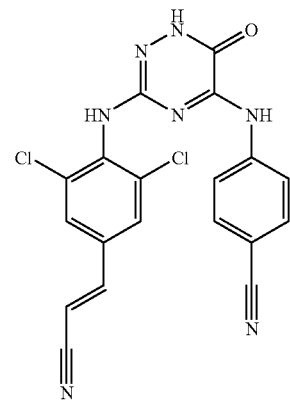
Co. No. 40; Ex. B1b-1); (E + Z); 424[M + H⁺]
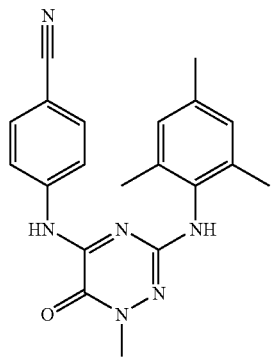
Co. No. 21; Ex. B4a); 361[M + H⁺]
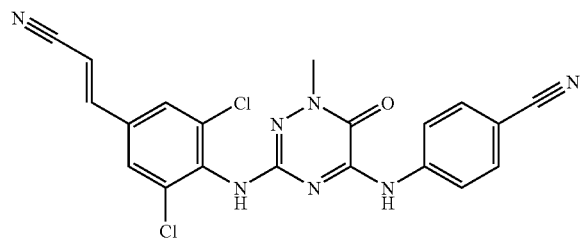
Co. No. 41; Ex. B4a); (E + Z); 438[M + H⁺]
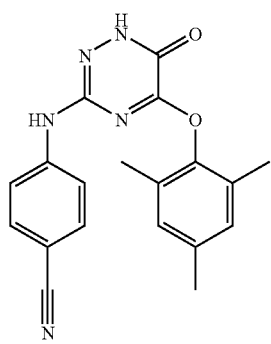
Co. No. 22; Ex. B1a); 348[M + H⁺]
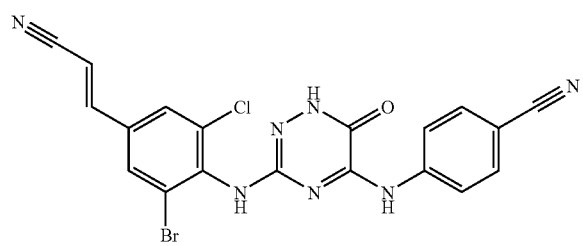
Co. No. 42; Ex. B1b-1); (E + Z); 468[M + H⁺]

TABLE 1-continued
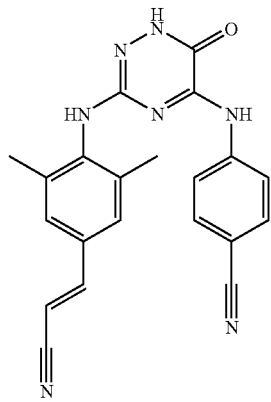
Co. No. 4; Ex. B1b-1); (E); mp. 374-375° C.
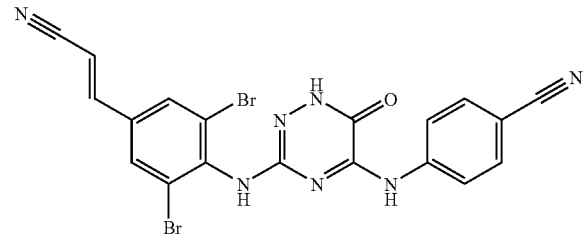
Co. No. 43; Ex. B1b-1); (E + Z); 512[M + H⁺]
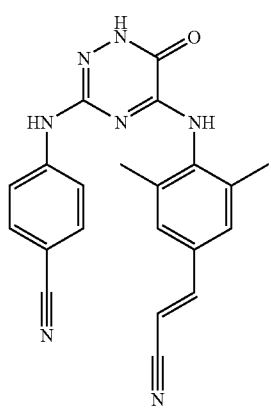
Co. No. 23; Ex. B1b-1); 384[M + H⁺]
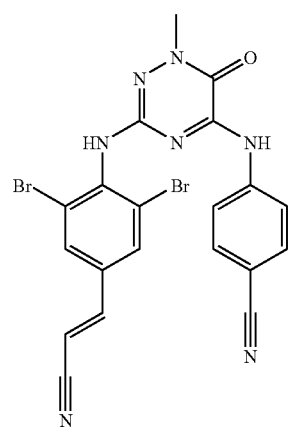
Co. No. 44; Ex. B4b)
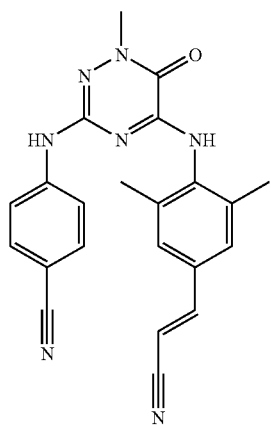
Co. No. 24; Ex. B4a); (E); 398[M + H⁺]
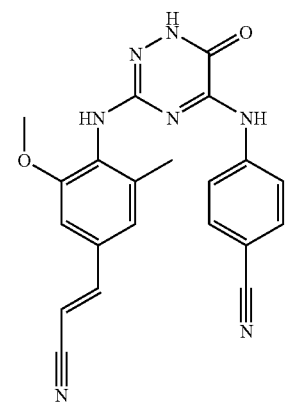
Co. No. 45; Ex. B1b-1)/B1b-2); (E); mp. 333-336° C.

TABLE 1-continued
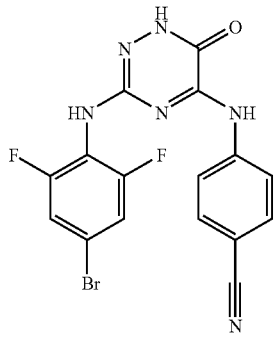
Co. No. 10; Ex. B1a); mp. 308-310° C.
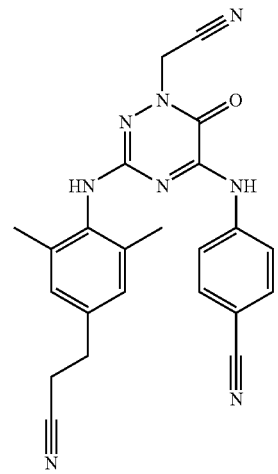
Co. No. 12; Ex. B6a-1); mp. 243-246° C.
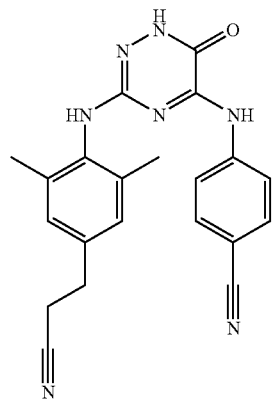
Co. No. 5; Ex. B2/B1b); mp. 336-337° C.
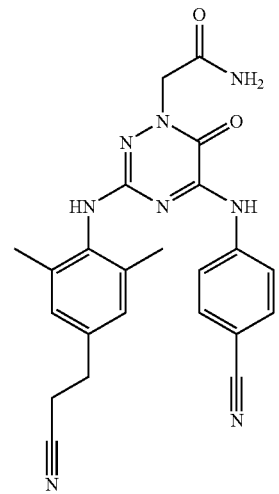
Co. No. 13; Ex. B6b-1); mp. 289-291° C.
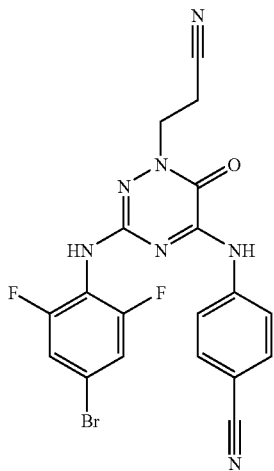
Co. No. 11; Ex. B5; mp. 246-247° C.
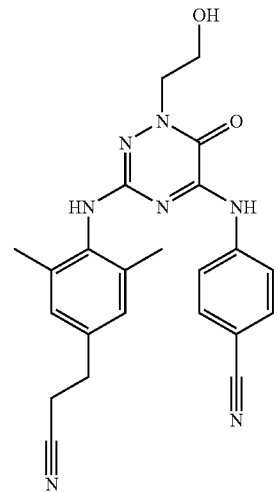
Co. No. 14; Ex. B6c-1); 430[M + H$^+$]

TABLE 1-continued
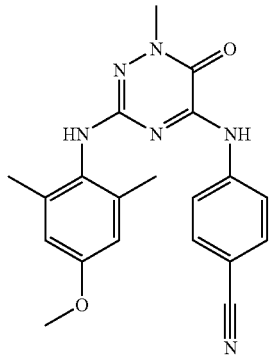
Co. No. 25; Ex. B4a); 377[M + H⁺]
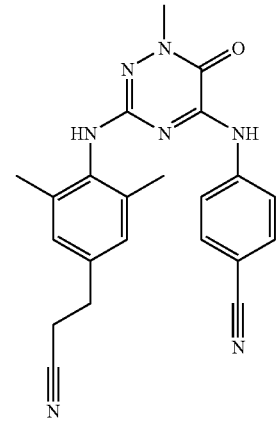
Co. No. 9; Ex. B4b); mp. 317-320° C.
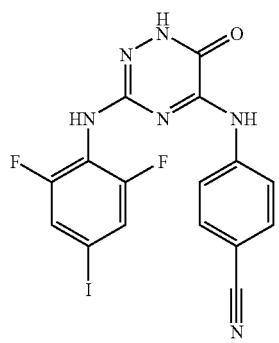
Co. No. 1; Ex. B1a); mp. 287-290° C.
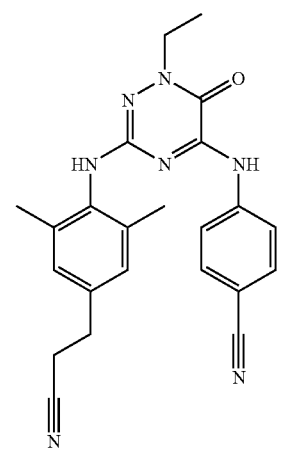
Co. No. 15; Ex. B6d-1); mp. 243-245° C.
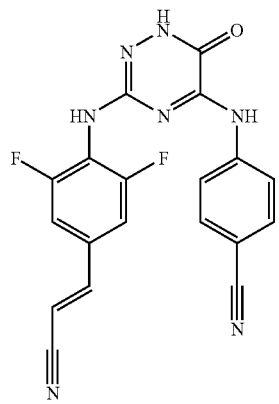
Co. No. 26; Ex. B1b-1); (E); mp. 300-303° C.
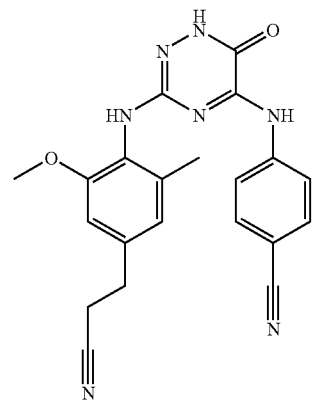
Co. No. 46; Ex. B1b-2); mp. 303-304° C.

TABLE 1-continued
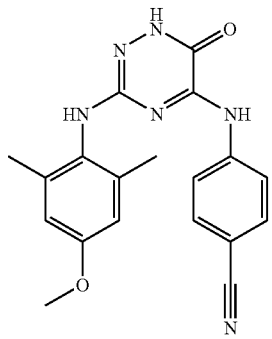
Co. No. 27; Ex. B1b-1); mp. 312-314° C.
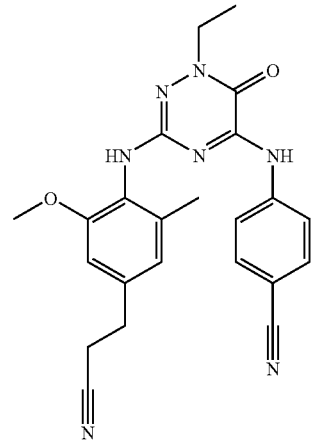
Co. No. 47; Ex. B6d-1); (E); mp. 273-274° C.
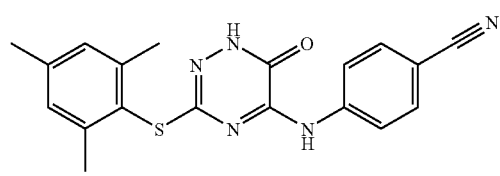
Co. No. 6; Ex. B1b-1); mp. 332-333° C.
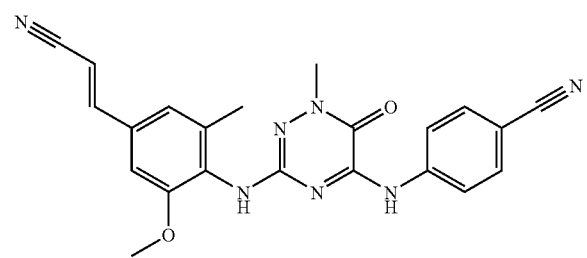
Co. No. 48; Ex. B4b); (E); mp. 325-326° C.
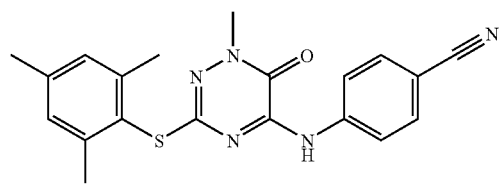
Co. No. 28; Ex. B4a); mp. 299-301° C.
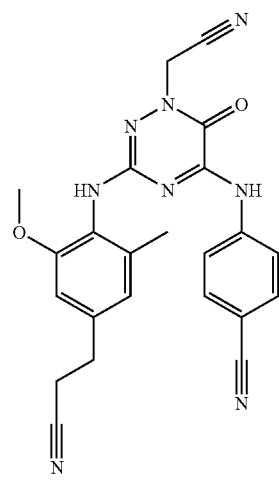
Co. No. 49; Ex. B6a-1); 441[M + H$^+$]

TABLE 1-continued
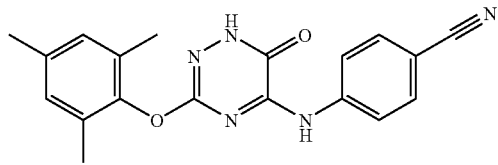
Co. No. 29; Ex. B1b-1); mp. 375-377° C.
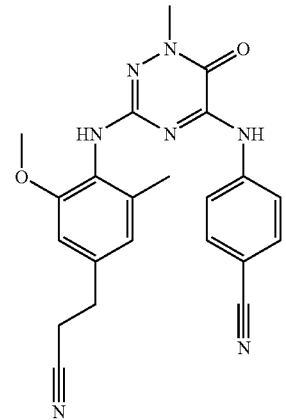
Co. No. 50; Ex. B4b); mp. 284-286° C.
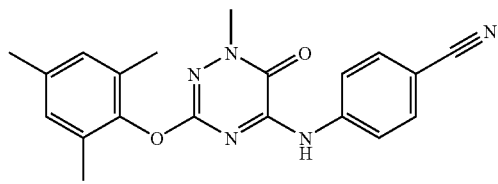
Co. No. 30; Ex; B4a); mp. 273-275° C.
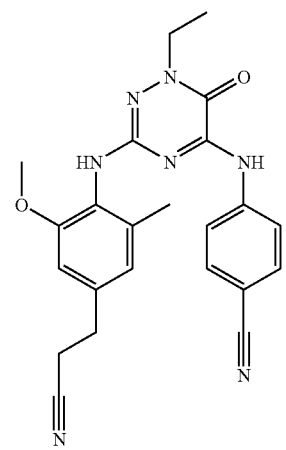
Co. No. 51; Ex; B6d-1); mp. 263-264° C.
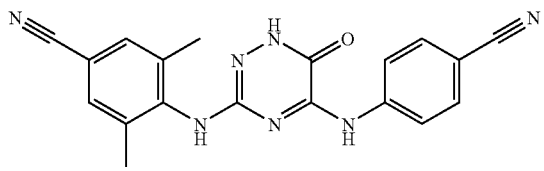
Co. No. 31; Ex. B1b-1); mp. 377-378° C.
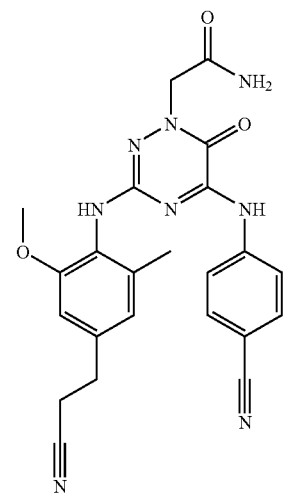
Co. No. 52; Ex. B6b-1); mp. 292-293° C.

TABLE 1-continued
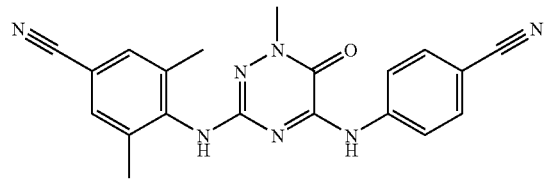
Co. No. 32; Ex. B4a); mp. 370-373° C.
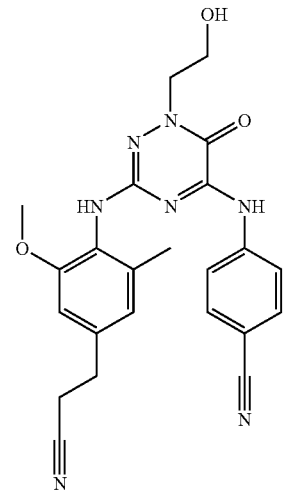
Co. No. 53; Ex. B6c-1); 426[M + H⁺]
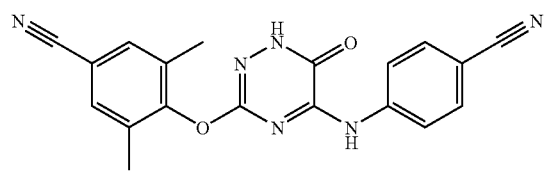
Co. No. 33; Ex. B1b-1); mp. 392-393° C.
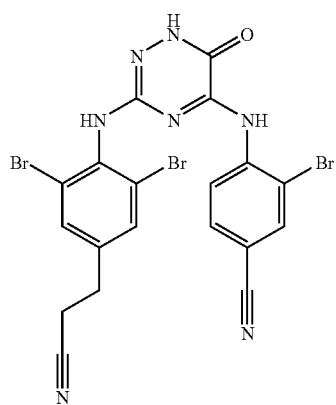
Co. No. 54; Ex. B1b-2); mp. 335-336° C.
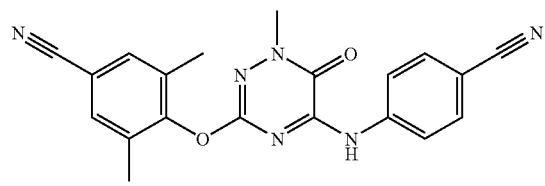
Co. No. 34; Ex. B4a); mp. 306-308° C.
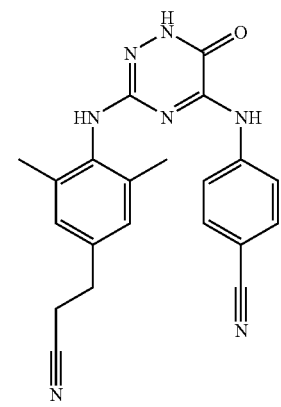
Co. No. 3; Ex. B1b-2); mp. 351-352° C.

TABLE 1-continued
Co. No. 7; Ex. B3; mp. 303-304° C.
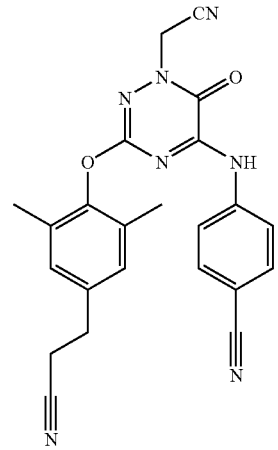
Co. No. 55; Ex. B6a-2; 426[M + H+]
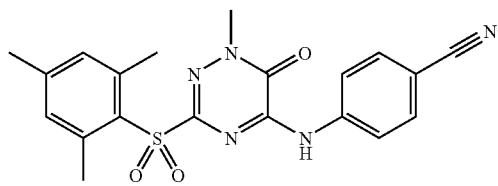
Co. No. 35; Ex. B4a; mp. 308-310° C.
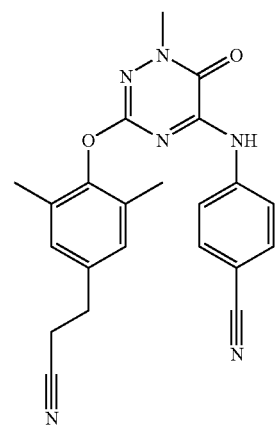
Co. No. 56; Ex. B4b; 401[M + H+]
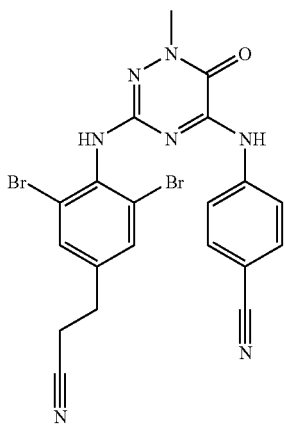
Co. No. 8; Ex. B4a); 528[M + H+]
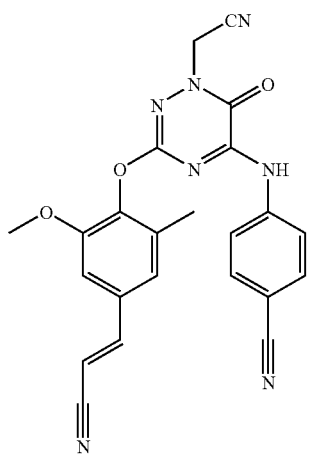
Co. No. 57; Ex. B6a-2; (E); mp. 276-277° C.

TABLE 1-continued
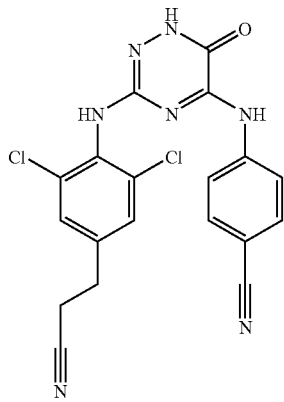
Co. No. 36; B1b-1); mp. 306-308° C.
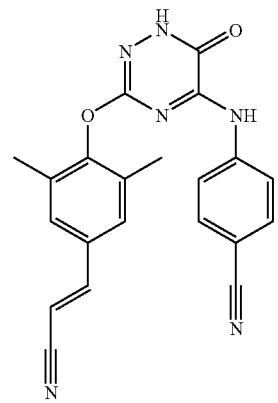
Co. No. 58; B1b-2); 385[M + H⁺]
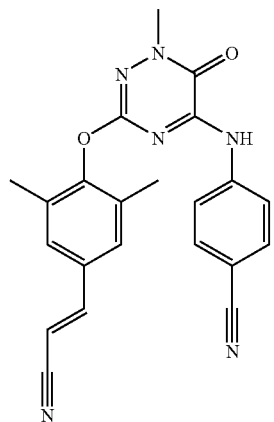
Co. No. 59; Ex. B4c); 399[M + H⁺]
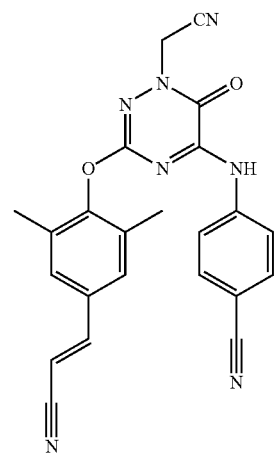
Co. No. 60; Ex. B6a-2); 424[M + H⁺]
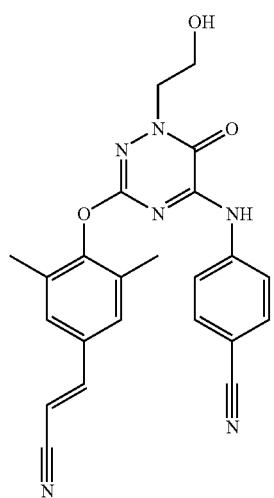
Co. No. 61; Ex. B6c-2); 429[M + H⁺]
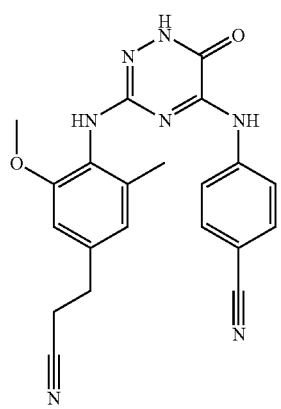
Co. No. 62; Ex. B1b-3); 385[M + H⁺]

TABLE 1-continued
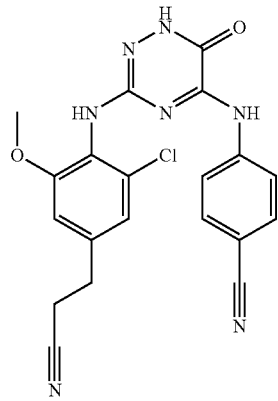
Co. No. 63; Ex. B1b-2); 422[M + H⁺]
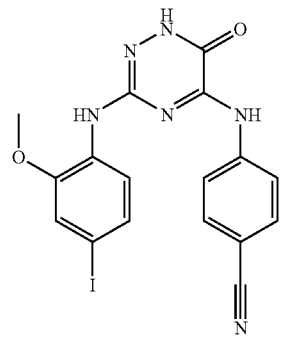
Co. No. 64; Ex. B1b-3); 461[M + H⁺]
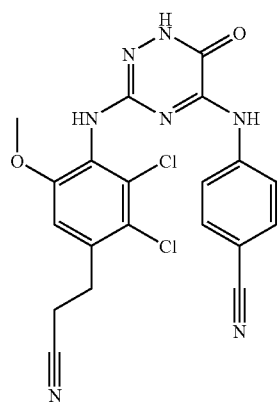
Co. No. 65; Ex. B1b-3); 456[M + H⁺]
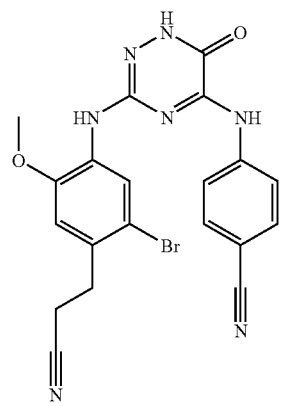
Co. No. 66; Ex. B1b-3); 466[M + H⁺]
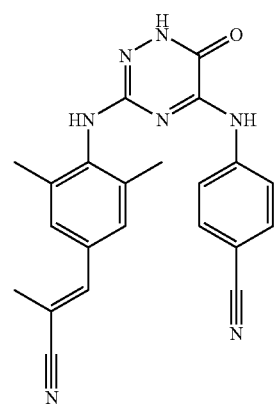
Co. No. 67; Ex. B1b-2); 398[M + H⁺]
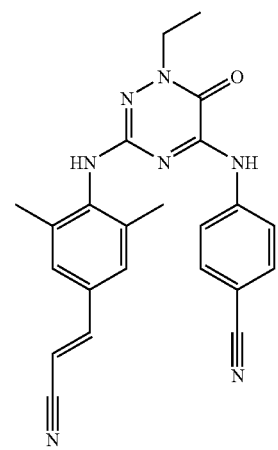
Co. No. 68; Ex. B6d-2); 413[M + H⁺]

TABLE 1-continued
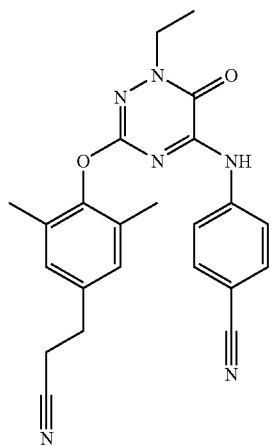
Co. No. 69; Ex. B6d-2); 415[M + H⁺]
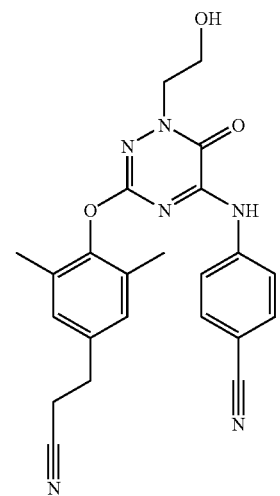
Co. No. 70; Ex. B6c-2); 466[M + H⁺]
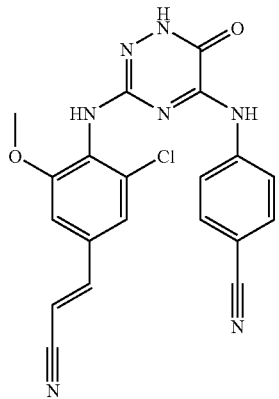
Co. No. 71; Ex. B1b-3); 420[M + H⁺]
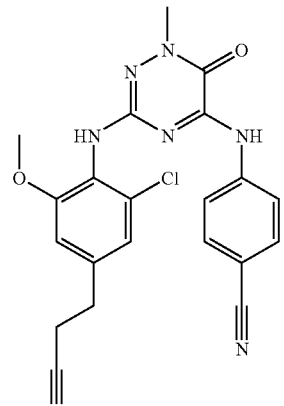
Co. No. 72; Ex. B4c; 436[M + H⁺]
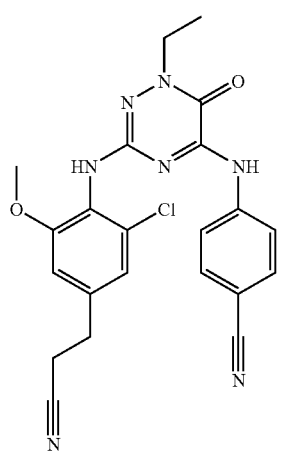
Co. No. 73; Ex. B6d-2; 560[M + H⁺]
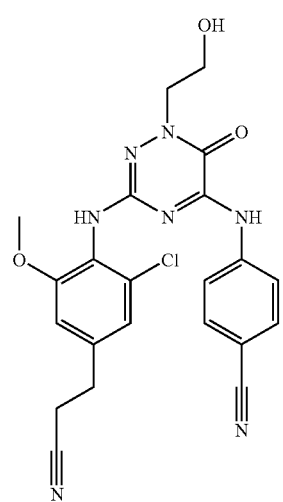
Co. No. 74; Ex. B6c-2); 466[M + H⁺]

TABLE 1-continued

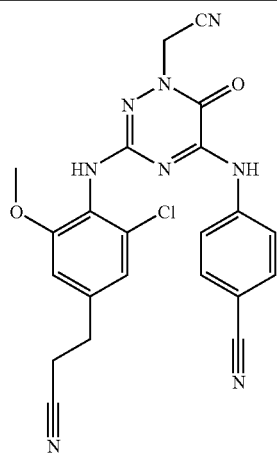

Co. No. 75; Ex. B6a-2); 461[M + H⁺]

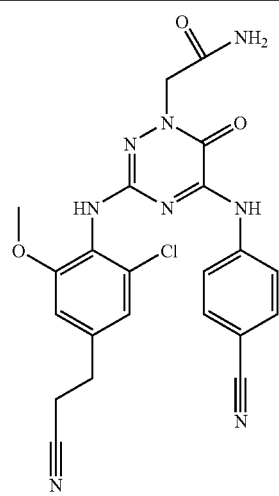

Co. No. 76; Ex. B6b-2); 479[M + H⁺]

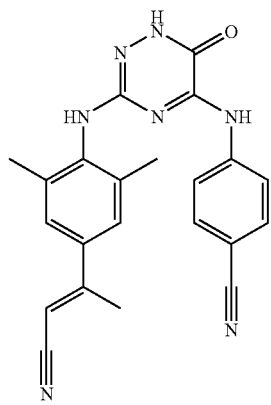

Co. No. 77; Ex. B4b-2); 398[M + H⁺]

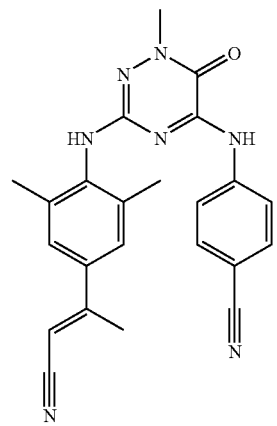

Co. No. 78; Ex. B4c); 412[M + H⁺]

[M + H⁺] is the mass of the protonated compound (Chemical Ionisation Mass Spectrum)

C. Pharmacological Example

The pharmacological activity of the present compounds was examined using the following test.

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445-451, 1985) to be highly susceptible to and permissive for HIV infection, served as the target cell line. In these cells, engineered with GFP (and an HIV-specific promotor), ongoing HIV-infection was measured fluorometrically. Cytotoxicity is measured in the same cells, but engineered with GFP under a constitutional promotor. The infection (or inhibition thereof) of HIV infected cells and the fluorescence of mock-infected cells is assessed by the fluorescent GFP signal generated by the two above mentioned cell lines.

The 50% effective concentration ($EC_{50}$ in IM) was defined as the concentration of compound that reduced the fluorescence of HIV-infected cells by 50%. The 50% cytotoxic concentration ($CC_{50}$ in μM) was defined as the concentration of compound that reduced fluorescence of the mock-infected cells by 50%.

The compounds of formula (I) were shown to inhibit HIV-1 effectively. Particular $pEC_{50}$ ($-logEC_{50}$) values are listed in Table 2 hereinbelow. For example, a compound with a $EC_{50}$ value of $10^{-9}$M has a $pEC_{50}=9$

TABLE 2

| Co. No. | $pEC_{50}$ |
|---------|-----------|
| 16 | 9.0 |
| 17 | 9.0 |
| 18 | 7.9 |
| 19 | 8.2 |
| 20 | 9.2 |
| 21 | 9.0 |
| 22 | 7.8 |
| 4 | 9.2 |
| 23 | 9.1 |
| 24 | 9.2 |
| 10 | 9.5 |
| 5 | 9.6 |
| 11 | 9.1 |
| 25 | 9.2 |
| 1 | 9.5 |
| 26 | 9.2 |
| 27 | 9.7 |
| 6 | 7.8 |
| 28 | 8.4 |
| 29 | 6.5 |
| 30 | 9.2 |

TABLE 2-continued

| Co. No. | pEC$_{50}$ |
|---|---|
| 31 | 9.5 |
| 32 | 8.9 |
| 33 | 9.2 |
| 34 | 8.5 |
| 7 | 7.7 |
| 35 | 8.0 |
| 8 | 10.0 |
| 36 | 9.9 |
| 37 | 9.9 |
| 38 | 9.9 |
| 39 | 10.0 |
| 2 | 10.0 |
| 40 | 9.5 |
| 41 | 9.7 |
| 42 | 9.4 |
| 43 | 9.5 |
| 13 | 8.6 |
| 14 | 9.5 |
| 9 | 9.3 |
| 15 | 9.7 |
| 46 | 9.6 |
| 47 | 9.1 |
| 48 | 9.4 |
| 49 | 9.5 |
| 50 | 9.8 |
| 51 | 9.6 |
| 52 | 8.8 |
| 53 | 9.4 |
| 3 | 9.2 |
| 56 | 9.2 |
| 55 | 9 |
| 58 | 8.5 |
| 59 | 8.9 |
| 60 | 8.6 |
| 61 | 8.9 |
| 62 | 9.5 |
| 67 | 8.82 |
| 68 | 8.92 |
| 54 | 7.12 |
| 69 | 9.05 |
| 70 | 9.1 |
| 71 | 9.1 |
| 72 | 9.2 |
| 73 | 9.2 |
| 74 | 9.1 |
| 75 | 9.1 |
| 77 | 9.1 |
| 78 | 9.1 |
| 67 | 9.0 |

The invention claimed is:

1. A compound of formula

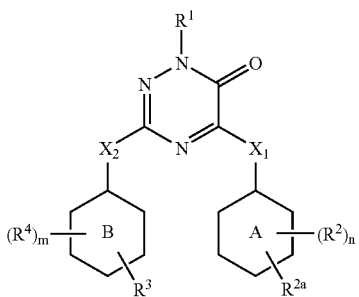

(I)

a N-oxide, a pharmaceutically acceptable acid addition salt, or a stereochemically isomeric form thereof, wherein ring A represents phenyl;
ring B represents phenyl;
n is 1, 2, 3 or 4;
m is 1, 2, 3 or 4;
$R^1$ represents hydrogen; aryl; formyl; $C_{1-6}$alkylcarbonyl; $C_{1-6}$alkyloxycarbonyl; $C_{1-6}$alkyl optionally substituted with $R^5$; or $C_{1-6}$alkyloxy$C_{1-6}$alkylcarbonyl substituted with $C_{1-6}$alkyloxycarbonyl;
each $R^2$ independently represents hydrogen; hydroxy; halo; $C_{1-6}$alkyl optionally substituted with one or more substituents each independently selected from halo, cyano, hydroxy or —C(=O)$R^6$; $C_{2-6}$alkenyl optionally substituted with one or more substituents each independently selected from halo, cyano, hydroxy or —C(=O)$R^6$; $C_{2-6}$alkynyl optionally substituted with one or more substituents each independently selected from halo, cyano, hydroxy or —C(=O)$R^6$; $C_{3-7}$cycloalkyl; $C_{1-6}$alkyloxy; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; —S(=O)$_p$$R^6$; —NH—S(=O)$_p$$R^6$; —C(=O)$R^6$; —NHC(=O)H; —C(=O)NHNH$_2$; NHC(=O)$R^6$; C(=NH)$R^6$; or $R^7$;
$R^{2a}$ represents cyano; aminocarbonyl; amino; halo; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; $C_{1-6}$alkyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkynyl optionally substituted with one or more substituents each independently selected from halo, cyano, hydroxy, NR$^9$R$^{10}$, —C(=O)—NR$^9$R$^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; —C(=N—O—$R^8$)—$C_{1-4}$alkyl; $R^7$ or —X$_3$—$R^7$;
X$_1$ represents —NR$^1$—; —NH—NH—; —N=N—; —O—; —C(=O)—; —$C_{1-4}$alkanediyl-; —CHOH—; —S—; —S(=O)$_p$—; —X$_4$—$C_{1-4}$alkanediyl-; —$C_{1-4}$alkanediyl-X$_4$—; or —$C_{1-4}$alkanediyl-X$_4$—$C_{1-4}$alkanediyl-;
X$_2$ represents —NR$^1$—; —NH—NH—; —N=N—; —O—; —C(=O)—; —$C_{1-4}$alkanediyl-; —CHOH—; —S—; —S(=O)$_p$—; —X$_4$—$C_{1-4}$alkanediyl-; —$C_{1-4}$alkanediyl-X$_4$—; or —$C_{1-4}$alkanediyl-X$_4$—$C_{1-4}$alkanediyl-;

$X_3$ represents $-NR^1-$; $-NH-NH-$; $-N=N-$; $-O-$; $-C(=O)-$; $-S-$; $-S(=O)_p-$; $-X_{4a}-C_{1-4}$alkanediyl-; $-C_{1-4}$alkanediyl-$X_{4b}-$; $-C_{1-4}$alkanediyl-$X_{4a}-C_{1-4}$alkanediyl-; or $-C(=N-OR^8)-C_{1-4}$alkanediyl-;

$X_4$ represents $-NR^1-$; $-NH-NH-$; $-N=N-$; $-O-$; $-C(=O)-$; $-CHOH-$; $-S-$; or $-S(=O)_p-$;

$X_{4a}$ represents $-NR^1-$; $-NH-NH-$; $-N=N-$; $-C(=O)-$; $-S-$; or $-S(=O)_p-$;

$X_{4b}$ represents $-NH-NH-$; $-N=N-$; $-O-$; $-C(=O)-$; $-S-$; or $-S(=O)_p-$;

$R^3$ represents cyano; aminocarbonyl; amino; halo; $NHR^{13}$; $NR^{13}R^{14}$; $-C(=O)-NHR^{13}$; $-C(=O)-NR^{13}R^{14}$; $-C(=O)-R^{15}$; $-CH=N-NH-C(=O)-R^{16}$; $C_{1-6}$alkyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $C_{1-6}$alkyloxy optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $C_{1-6}$alkyloxy$C_{1-6}$alkyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $C_{2-6}$alkenyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $C_{2-6}$alkynyl optionally substituted with one or more substituents each independently selected from halo, cyano, hydroxy, $NR^9R^{10}$, $-C(=O)-NR^9R^{10}$, $-C(=O)-C_{1-6}$alkyl, $-C(=O)-O-C_{1-6}$alkyl, $-C(=O)$-polyhalo$C_{1-6}$alkyl, $-C(=O)-O$-polyhalo$C_{1-6}$alkyl or $R^7$; $-C(=N-O-R^8)-C_{1-4}$alkyl; $R^7$ or $-X_3-R^7$;

each $R^4$ independently represents hydrogen; hydroxy; halo; $C_{1-6}$alkyl optionally substituted with one or more substituents each independently selected from halo, cyano, hydroxy or $-C(=O)R^6$; $C_{2-6}$alkenyl optionally substituted with one or more substituents each independently selected from halo, cyano, hydroxy or $-C(=O)R^6$;

$C_{2-6}$alkynyl optionally substituted with one or more substituents each independently selected from halo, cyano, hydroxy or $-C(=O)R^6$; $C_{3-7}$cycloalkyl; $C_{1-6}$alkyloxy; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-4}$alkyl; polyhalo$C_{1-4}$alkyloxy; polyhalo$C_{1-4}$alkylthio; $-S(=O)_pR^6$; $-NH-S(=O)_pR^6$; $-C(=O)R^6$; $-NHC(=O)H$; $-C(=O)NHNH_2$; $NHC(=O)R^6$; $C(=NH)R^6$; or $R^7$;

$R^5$ represents formyl, cyano, aminocarbonyl, mono- or di($C_{1-4}$alkyl)aminocarbonyl, hydroxy, $C_{1-6}$alkylcarbonyl, $C_{1-6}$alkyloxycarbonyl or $C_{1-6}$alkylcarbonyloxy;

$R^6$ represents $C_{1-4}$alkyl, amino, mono- or di($C_{1-4}$alkyl)amino or polyhalo$C_{1-4}$alkyl;

$R^7$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may, whenever possible, optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $-CH(=N-O-R^8)$, $R^{7a}$, $-X_3-R^{7a}$ or $R^{7a}-C_{1-4}$alkanediyl-;

$R^{7a}$ represents a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; or a monocyclic, bicyclic or tricyclic aromatic heterocycle; wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $-CH(=N-O-R^8)$;

$R^8$ represents hydrogen, $C_{1-4}$alkyl optionally substituted with aryl, or aryl;

$R^9$ and $R^{10}$ each independently represent hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl; $-CH(=NR^{11})$ or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$, or $R^7$; or $R^9$ and $R^{10}$ may be taken together to form a bivalent radical of formula

| | |
|---|---|
| $-CH_2-CH_2-CH_2-CH_2-$ | (d-1) |
| $-CH_2-CH_2-CH_2-CH_2-CH_2-$ | (d-2) |
| $-CH_2-CH_2-O-CH_2-CH_2-$ | (d-3) |
| $-CH_2-CH_2-S-CH_2-CH_2-$ | (d-4) |
| $-CH_2-CH_2-NR^{12}-CH_2-CH_2-$ | (d-5) |
| $-CH_2-CH=CH-CH_2-$ | (d-6) |

$R^{11}$ represents cyano; $C_{1-4}$alkyl optionally substituted with $C_{1-4}$alkyloxy, cyano, amino, mono- or di($C_{1-4}$alkyl)amino or aminocarbonyl; $C_{1-4}$alkylcarbonyl;

$C_{1-4}$alkyloxycarbonyl; aminocarbonyl; mono- or di($C_{1-4}$alkyl)aminocarbonyl;

$R^{12}$ represents hydrogen or $C_{1-4}$alkyl;

$R^{13}$ and $R^{14}$ each independently represent $C_{1-6}$alkyl optionally substituted with cyano or aminocarbonyl or mono- or di($C_{1-4}$alkyl)aminocarbonyl, $C_{2-6}$alkenyl optionally substituted with cyano or aminocarbonyl or mono- or di($C_{1-4}$alkyl)aminocarbonyl, $C_{2-6}$alkynyl optionally substituted with cyano or aminocarbonyl or mono- or di($C_{1-4}$alkyl)aminocarbonyl;

$R^{15}$ represents $C_{1-6}$alkyl optionally substituted with cyano or aminocarbonyl or mono- or di($C_{1-4}$alkyl)aminocarbonyl;

$R^{16}$ represents $C_{1-6}$alkyl optionally substituted with cyano or aminocarbonyl or mono- or di($C_{1-4}$alkyl)aminocarbonyl, or $R^7$;

p is 1 or 2;

aryl represents phenyl or phenyl substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $R^7$ or —$X_3$—$R^7$.

2. A compound according to claim 1 wherein $R^{13}$ and $R^{14}$ each independently represent $C_{1-6}$alkyl optionally substituted with cyano or aminocarbonyl, $C_{2-6}$alkenyl optionally substituted with cyano or aminocarbonyl, $C_{2-6}$alkynyl optionally substituted with cyano or aminocarbonyl;

$R^{15}$ represents $C_{1-6}$alkyl optionally substituted with cyano or aminocarbonyl;

$R^{16}$ represents $C_{1-6}$alkyl optionally substituted with cyano or aminocarbonyl, or $R^7$.

3. A compound according to claim 1 wherein the compound has the formula

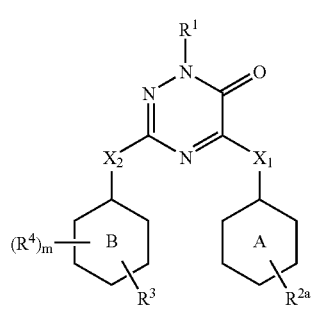

(I-1)

wherein $R^1$, $R^{2a}$, $R^3$, $R^4$, m, $X_1$, $X_2$, ring A and ring B are as defined in claim 1.

4. A compound according to claim 3 wherein the compound has the formula

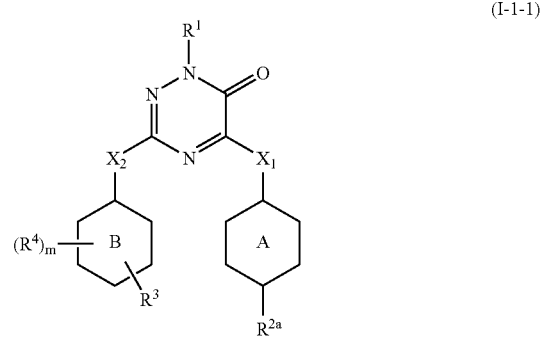

(I-1-1)

wherein $R^1$, $R^{2a}$, $R^3$, $R^4$, m, $X_1$, $X_2$, ring A and ring B are as defined therein.

5. A compound according to claim 4 wherein the compound has the formula

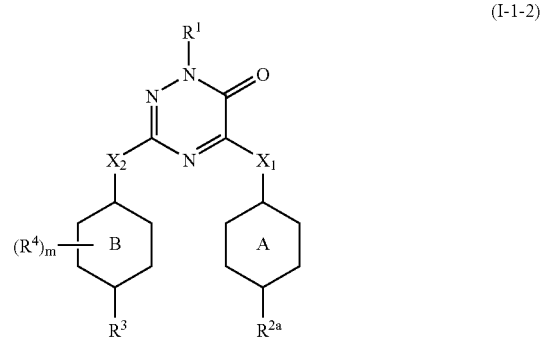

(I-1-2)

wherein $R^1$, $R^{2a}$, $R^3$, $R^4$, m, $X_1$, $X_2$, ring A and ring B are as defined therein.

6. A compound according to claim 5 wherein the compound has the formula

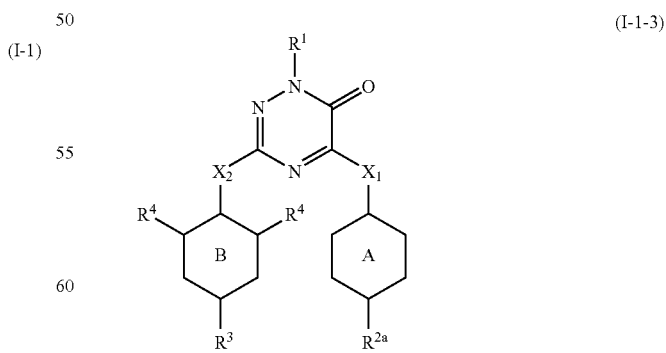

(I-1-3)

wherein $R^1$, $R^{2a}$, $R^3$, $R^4$, $X_1$, $X_2$, ring A and ring B are as defined therein with the proviso that $R^4$ is other than hydrogen.

7. A compound according to claim 1 wherein the compound has the formula

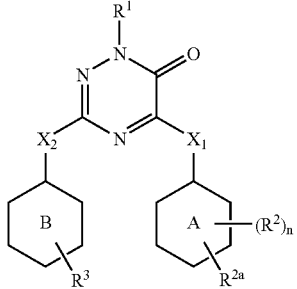
(I-2)

wherein $R^1$, $R^{2a}$, $R^2$, $R^3$, $X_1$, $X_2$, n, ring A and ring B are as defined therein.

8. A compound according to claim 7 wherein the compound has the formula

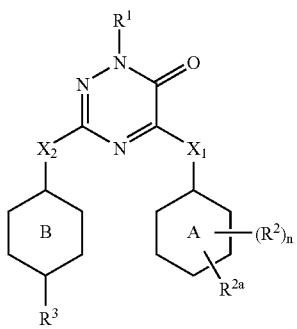
(I-2-1)

wherein $R^1$, $R^{2a}$, $R^2$, $R^3$, $X_1$, $X_2$, n, ring A and ring B are as defined therein.

9. A compound according to claim 8 wherein the compound has the formula

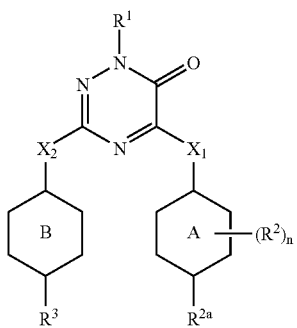
(I-2-2)

wherein $R^1$, $R^{2a}$, $R^2$, $R^3$, $X_1$, $X_2$, n, ring A and ring B are as defined therein.

10. A compound according to claim 9 wherein the compound has the formula

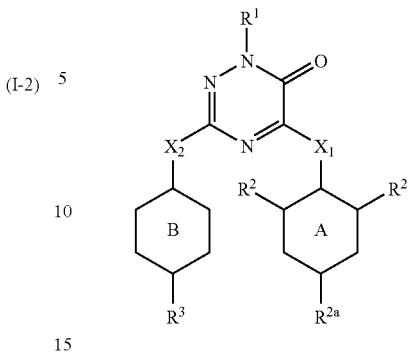
(I-2-3)

wherein $R^1$, $R^{2a}$, $R^2$, $R^3$, $X_1$, $X_2$, ring A and ring B are as defined therein with the proviso that $R^2$ is other than hydrogen.

11. A compound according to claim 1 wherein
m is 1 or 2;
$R^4$ represents halo; $C_{1-6}$alkyl; $C_{1-6}$alkyloxy; and
$R^3$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)-β-polyhalo$C_{1-6}$alkyl or $R^7$; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$.

12. A compound according to claim 11 wherein $R^3$ represents cyano; aminocarbonyl; $C_{1-6}$alkyl substituted with cyano or aminocarbonyl; $C_{2-6}$alkenyl substituted with cyano or aminocarbonyl; or $C_{2-6}$alkynyl substituted with cyano or aminocarbonyl.

13. A compound according to claim 1 wherein
n is 1 or 2;
$R^2$ represents halo; $C_{1-6}$alkyl; $C_{1-6}$alkyloxy; and
$R^{2a}$ represents cyano; aminocarbonyl; amino; halo; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{1-6}$alkyloxy$C_{1-6}$alkyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$; $C_{2-6}$alkenyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)-β-polyhalo$C_{1-6}$alkyl or $R^7$; $C_{2-6}$alkynyl optionally substituted with one or more substituents each independently selected from halo, cyano, hydroxy, $NR^9R^{10}$, —C(=O)—$NR^9R^{10}$, —C(=O)—$C_{1-6}$alkyl, —C(=O)—O—$C_{1-6}$alkyl, —C(=O)-polyhalo$C_{1-6}$alkyl, —C(=O)—O-polyhalo$C_{1-6}$alkyl or $R^7$.

14. A compound according to claim 13 wherein $R^{2a}$ represents cyano; aminocarbonyl; $C_{1-6}$alkyl substituted with cyano or aminocarbonyl; $C_{2-6}$alkenyl substituted with cyano or aminocarbonyl; or $C_{2-6}$alkynyl substituted with cyano or aminocarbonyl.

15. A compound according to claim 1 wherein $R^{2a}$ is cyano, aminocarbonyl, $C_{1-6}$alkyl substituted with cyano or aminocarbonyl, or $C_{2-6}$alkenyl substituted with cyano or aminocarbonyl.

16. A compound according to claim 1 wherein $R^3$ is cyano, aminocarbonyl, $C_{1-6}$alkyl substituted with cyano or aminocarbonyl, or $C_{2-6}$alkenyl substituted with cyano or aminocarbonyl.

17. A compound as claimed in claim 1 wherein
n is 1, 2 or 3;
m is 1, 2 or 3;
$R^1$ represents hydrogen; $C_{1-6}$alkyl optionally substituted with cyano, aminocarbonyl or hydroxy;
each $R^2$ independently represents hydrogen; halo; $C_{1-6}$alkyl; or $C_{1-6}$alkyloxy;
$R^{2a}$ represents cyano; aminocarbonyl; halo; $C_{1-6}$alkyl optionally substituted with cyano or aminocarbonyl; $C_{1-6}$alkyloxy optionally substituted with cyano or aminocarbonyl; or $C_{2-6}$alkenyl optionally substituted with cyano or aminocarbonyl;
$X_1$ represents —$NR^1$—; —O—; —S—; or —$S(=O)_p$—;
$X_2$ represents —$NR^1$—; —O—; —S—; or —$S(=O)_p$—;
$R^3$ represents cyano; aminocarbonyl; halo; $C_{1-6}$alkyl optionally substituted with cyano or aminocarbonyl; $C_{1-6}$alkyloxy optionally substituted with cyano or aminocarbonyl; or $C_{2-6}$alkenyl optionally substituted with cyano or aminocarbonyl;
each $R^4$ independently represents hydrogen; halo; $C_{1-6}$alkyl; or $C_{1-6}$alkyloxy;
p is 2.

18. A compound according to claim 1 wherein $R^1$ represents hydrogen or $C_{1-6}$alkyl optionally substituted with $R^5$.

19. A compound according to claim 1 wherein $X_1$ represents —$NR^1$—; —O—; —S—; or —$S(=O)_p$—.

20. A compound according to claim 1 wherein $X_2$ represents —$NR^1$—; —O—; —S—; or —$S(=O)_p$—.

21. A compound according to claim 1 wherein $R^5$ represents cyano, aminocarbonyl or hydroxy.

22. The method of treating HIV infection comprising administering a therapeutically effective amount of a compound as claimed in claim 1 to a human in need of such treatment.

23. The method of treating drug or multidrug resistant HIV infection comprising administering a therapeutically effective amount of a compound as claimed in claim 1 to a human in need of such treatment.

24. A pharmaceutical composition comprising a pharmaceutically acceptable carrier and as active ingredient a therapeutically effective amount of a compound as claimed in claim 1.

25. A process for preparing a pharmaceutical composition according to claim 24 characterized in that a therapeutically effective amount of a compound as claimed therein is intimately mixed with a pharmaceutically acceptable carrier.

* * * * *